US012763206B2

(12) United States Patent
Sheikh et al.

(10) Patent No.: US 12,763,206 B2
(45) Date of Patent: Oct. 13, 2026

(54) INTELLIGENT CONTROL OF PAIRED APPLICATIONS

(71) Applicant: Oracle International Corporation, Redwood Shores, CA (US)

(72) Inventors: Salman Saleem Sheikh, Sanford, FL (US); Eugene Florintsev, Austin, TX (US)

(73) Assignee: Oracle International Corporation, Redwood Shores, CA (US)

( * ) Notice: Subject to any disclaimer, the term of this patent is extended or adjusted under 35 U.S.C. 154(b) by 120 days.

(21) Appl. No.: 18/882,504

(22) Filed: Sep. 11, 2024

(65) Prior Publication Data

US 2025/0097292 A1 Mar. 20, 2025

Related U.S. Application Data

(60) Provisional application No. 63/583,214, filed on Sep. 15, 2023.

(51) Int. Cl.
*G16H 40/67* (2018.01)
*G10L 15/18* (2013.01)
(Continued)

(52) U.S. Cl.
CPC ............ *G16H 40/67* (2018.01); *G10L 15/18* (2013.01); *G10L 15/22* (2013.01); *G16H 10/60* (2018.01);
(Continued)

(58) Field of Classification Search
CPC ..... G10L 15/18; G10L 15/1815; G10L 15/22; G10L 2015/223; G16H 10/60;
(Continued)

(56) References Cited

U.S. PATENT DOCUMENTS

2021/0343415 A1 11/2021 Allen et al.
2022/0084508 A1 3/2022 Kuo et al.
(Continued)

FOREIGN PATENT DOCUMENTS

CN 113223506 A 8/2021
EP 4068279 A1 10/2022
(Continued)

OTHER PUBLICATIONS

"Real-time updates with Turbo Streams", hotrails.dev. Published Feb. 2, 2022. Accessed Mar. 6, 2026. < https://www.hotrails.dev/turbo-rails/turbo-streams>. (Year: 2022).*
(Continued)

*Primary Examiner* — Christopher Biagini
(74) *Attorney, Agent, or Firm* — Kilpatrick Townsend & Stockton LLP

(57) ABSTRACT

Techniques are disclosed for assisting healthcare providers with common clinical tasks by way of a clinical software application that can be installed on and utilized from various client computing devices. The clinical software application (s) can enable a healthcare provider to record conversations with patients, dictate in natural language, generate patient notes, populate patient records, schedule tasks and generate task notifications, and perform numerous other clinical functions. Applications executing on a mobile computing device and a desktop computing device and concurrently associated with a same user session with a cloud service provider platform, can be paired with one another so that the mobile client application and the desktop client application can operate in concert, under the control of the cloud service provider platform, to provide an end user with a single seamless experience when the end user switches between client devices while performing a task.

20 Claims, 18 Drawing Sheets

(51) Int. Cl.
*G10L 15/22* (2006.01)
*G16H 10/60* (2018.01)
*G16H 40/20* (2018.01)
*H04L 67/1095* (2022.01)
*H04L 67/142* (2022.01)

(52) U.S. Cl.
CPC ......... *G16H 40/20* (2018.01); *H04L 67/1095* (2013.01); *H04L 67/142* (2013.01); *G10L 2015/223* (2013.01)

(58) Field of Classification Search
CPC ........ G16H 40/20; G16H 40/67; G16H 50/20; G16H 80/00; H04L 51/02; H04L 51/18; H04L 51/52; H04L 67/10; H04L 67/1095; H04L 67/142; H04L 67/306
See application file for complete search history.

(56) References Cited

U.S. PATENT DOCUMENTS

| | | | |
|---|---|---|---|
| 2022/0093107 | A1 | 3/2022 | Grancharov et al. |
| 2022/0344038 | A1 | 10/2022 | Gallopyn et al. |
| 2023/0135179 | A1 | 5/2023 | Mielke et al. |
| 2023/0186919 | A1 | 6/2023 | Ye et al. |
| 2023/0197057 | A1 | 6/2023 | Chen et al. |
| 2023/0352127 | A1 | 11/2023 | Sivan et al. |
| 2024/0029901 | A1 | 1/2024 | Ezhov et al. |

FOREIGN PATENT DOCUMENTS

| | | | |
|---|---|---|---|
| KR | 102505927 | B1 | 3/2023 |
| WO | 2023215105 | A1 | 11/2023 |

OTHER PUBLICATIONS

Asyrofi , et al., "CrossASR Efficient Differential Testing of Automatic Speech Recognition via Text-To-Speech", 2020 Institute of Electrical and Electronics Engineers International Conference on Software Maintenance and Evolution (ICSME), Available online at: https://ieeexplore.ieee.org/document/9240600, Sep. 28, 2020, pp. 640-650.
Bender, et al., "Improving Multi-Domain Learning by Balancing Batches With Domain Information", WebMedia '23: Proceedings of the 29th Brazilian Symposium on Multimedia and the Web, Available online at: https://dl.acm.org/doi/10.1145/3617023.3617037, Oct. 23, 2023, 2 pages.
Budzianowski, et al., "Enhancing Phone Customer Service with ASR Customization", Available Online at: https://resources.nvidia.com/en-us-speech-ai-content/telecom-with-nvidia-customized-speech-ai, Jan. 9, 2024, pp. 1-7.
Chen , et al., "Enhancing Automatic Speech Recognition Performance Through Multi-Speaker Text-to-Speech", Available online at: https://homepage.iis.sinica.edu.tw/papers/whm/26003-F.pdf, Dec. 13, 2021, 6 pages.
Ferri Molla, "Exploring Multimodal Foundation Models to Improve Interaction for People with Speech Impairments", Available online at: https://riunet.upv.es/bitstream/handle/10251/197532/Ferri%20-%20Exploring%20multimodal%20foundation%20models%20to%20improve%20interaction%20for%20people%20with%20speech%20impa....pdf?sequence=1&isAllowed=y, 2023, 64 pages.
Gao, et al., "Real-time Context-Aware Multimodal Network for Activity and Activity-Stage Recognition from Team Communication in Dynamic Clinical Settings", Proceedings of the ACM on Interactive, Mobile, Wearable and Ubiquitous Technologies, vol. 7, No. 1, Mar. 28, 2023, pp. 1-28.
Ghorbani , et al., "Domain Expansion for End-to-End Speech Recognition: Applications for Accent/Dialect Speech", Institute of Electrical and Electronics Engineers/Association for Computing Machinery Transactions on Audio, Speech, and Language Processing, vol. 31, Available online at: https://ieeexplore.ieee.org/abstract/document/10003977, Dec. 30, 2022, pp. 762-774.
Hono, et al., "An Integration of Pre-Trained Speech and Language Models for End-to-End Speech Recognition", Available Online at: https://arxiv.org/pdf/2312.03668v1, Dec. 6, 2003, 6 pages.
Hu, et al., "REDAT: Accent-Invariant Representation for End-to-End ASR by Domain Adversarial Training with Relabeling", Audio and Speech Processing, Available online at: https://arxiv.org/pdf/2012.07353.pdf, Feb. 12, 2021, 5 pages.
Jia, et al., "Federated Domain Adaptation for ASR with Full Self-Supervision", Available online at: https://arxiv.org/pdf/2203.15966.pdf, Apr. 5, 2022, 5 pages.
Joshi, et al., "A Simple Baseline for Domain Adaptation in End to End ASR Systems Using Synthetic Data", Audio and Speech Processing, Available online at: https://arxiv.org/pdf/2206.13240.pdf, Jun. 22, 2022, 6 pages.
Laptev, et al., "You Do Not Need More Data: Improving End-To-End Speech Recognition by Text-To-Speech Data Augmentation", Audio and Speech Processing, Available online at: https://arxiv.org/pdf/2005.07157.pdf, Jul. 30, 2020, 6 pages.
Li, et al., "ChatDoctor: A Medical Chat Model Fine-Tuned on a Large Language Model Meta-AI (LLaMA) Using Medical Domain Knowledge", Cureus, vol. 15, No. 6, Jun. 24, 2023, pp. 1-17.
Li, et al., "Multi-task Learning of Spoken Language Understanding by Integrating N-Best Hypotheses with Hierarchical Attention", Proceedings of the 28th International Conference on Computational Linguistics: Industry Track, Available online at: https://aclanthology.org/2020.coling-industry.11.pdf, Dec. 12, 2020, pp. 113-123.
Liang, et al., "Improving Code-Switching and Named Entity Recognition in ASR with Speech Editing based Data Augmentation", Computation and Language, Available online at: https://arxiv.org/pdf/2306.08588.pdf, Jun. 14, 2023, 5 pages.
Liu, et al., "Leveraging Large Language Models for Generating Responses to Patient Messages—a Subjective Analysis", Journal of the American Medical Informatics Association, vol. 31, No. 6, Jun. 1, 2024, pp. 1367-1379.
Masumura, et al., "Hierarchical Transformer-based Large-Context End-to-end ASR with Large-Context Knowledge Distillation", Computation and Language, Available online at: https://arxiv.org/pdf/2102.07935.pdf, Feb. 16, 2021, 5 pages.
Park , et al., "SpecAugment A Simple Data Augmentation Method for Automatic Speech Recognition", Audio and Speech Processing, Available online at: https://arxiv.org/pdf/1904.08779.pdf, Dec. 3, 2019, 6 pages.
Rasmy, et al., "Med-BERT: Pretrained Contextualized Embeddings on Large-scale Structured Electronic Health Records for Disease Prediction", Natural Partner Journal Digital Medicine, vol. 86, No. 1, 2021, pp. 1-13.
Sahraeian, et al., "Using Weighted Model Averaging in Distributed Multilingual DNNs to Improve Low Resource ASR", Procedia Computer Science, vol. 81, Available online at: https://www.sciencedirect.com/science/article/pii/S1877050916300576, May 9-12, 2016, pp. 152-158.
Salazar, "Text-To-Speech Data Augmentation for Low Resource Speech Recognition", Universitat Pompeu Fabra Barcelona, Available online at: https://arxiv.org/ftp/arxiv/papers/2204/2204.00291.pdf, Jun. 27, 2021, 48 pages.
Soldo, et al., "Template-based ASR Using Posterior Features and Synthetic References Comparing Different TTS Systems", Available online at: https://publications.idiap.ch/downloads/papers/2012/Soldo_SAPA-SCALE_2012.pdf, Jul. 10, 2012, 6 pages.
Tsunoo, et al., "Data Augmentation Methods for End-to-end Speech Recognition on Distant-Talk Scenarios", Audio and Speech Processing, Available online at: https://arxiv.org/abs/2106.03419, Jun. 7, 2021, 5 pages.
Ueno, "Data Augmentation Approaches for Automatic Speech Recognition Using Text-to-Speech", Available online at: https://repository.kulib.kyoto-u.ac.jp/dspace/bitstream/2433/275349/1/djohk00783.pdf, Mar. 3, 2022, 114 pages.
Ueno, et al., "Data Augmentation for ASR Using TTS via a Discrete Representation", Available online at: http://sap.ist.i.kyoto-u.ac.jp/EN/bib/intl/UEN-ASRU21.pdf, Dec. 13, 2021, pp. 68-75.

(56) References Cited

OTHER PUBLICATIONS

Zaiem, et al., "Fine-tuning Strategies for Faster Inference using Speech Self-Supervised Models: A Comparative Study", Audio and Speech Processing, Available online at: https://arxiv.org/pdf/2303.06740.pdf, Mar. 12, 2023, 5 pages.

* cited by examiner

INTELLIGENT CONTROL OF PAIRED APPLICATIONS

CROSS-REFERENCE TO RELATED APPLICATIONS

The present application claims the benefit of and priority to U.S. Provisional Application No. 63/583,214, filed Sep. 15, 2023, the entire contents of which are incorporated herein by reference for all purposes.

BACKGROUND

Clinical environments such as healthcare facilities often include different healthcare providers working together and communicating with one another to treat patients. Documenting patient encounters, capturing information conveyed during those encounters and/or pertaining to events occurring before and/or after the encounters, populating patient records such as electronic health records, and healthcare practice management are integral parts of the practice of many healthcare providers and important to ensuring high-quality healthcare. Traditional means for performing tasks associated with providing healthcare often involve several different disconnected devices such as listening devices, portable electronic devices, workstations, and the like and end users who are equipped with the training, knowledge, experience, and skills to properly utilize these devices and participate in the healthcare process. Relying on separate devices and qualified end users to perform clinical tasks is cumbersome, time and resource intensive, costly, and reduces efficiencies, which may lead to lower-quality healthcare.

BRIEF SUMMARY

Techniques are disclosed herein for improving the efficiency of and reducing the computing resources required to perform various healthcare services in a clinical environment. In certain embodiments, techniques are disclosed for equipping a healthcare provider end user with a clinical software application that can be placed on and utilized from one or both of a mobile computing device and a desktop computing device to facilitate performance of the various tasks typically rendered by a healthcare provider as part of providing healthcare services to patients. In some embodiments, the mobile computing application and the desktop computing application can be paired and subsequently controlled remotely by a cloud service provider platform, such that the effect of user interactions with an application on one of the mobile computing device or the desktop computing device will automatically be applied to the application on the other of the mobile computing device and the desktop computing device. This can allow an end user to seamlessly transition back-and-forth between the mobile computing device and the desktop computing device when interacting with a cloud service provider platform. For example, the end user can begin a task on one of the mobile computing device or the desktop computing device and complete the task on the other of the mobile computing device and the desktop computing device. When making the transition from the initially used computing device to the subsequently used computing device, the view presented on the subsequently used computing device will allow the end user to pick up the task exactly where the end user left off on the initially used computing device.

In some embodiments, a method includes receiving a first registration request message from a first client application executing on a first client device. The first registration request message includes information that at least identifies the first client device and capabilities of the first client device. The method also comprises receiving a second registration request message from a second client application executing on a second client device. The second registration request message includes information that at least identifies the second client device and capabilities of the second client device. The first client application is paired with the second client application upon registering the first client device and the second client device with a computing resource. The method additionally includes receiving, from the first client device in response to an end user interaction with the first client application, an identification of a state of the first client application and a task request message corresponding to a task to be performed by the computing resource. The method further comprises synchronizing a state of the second client application with the state of the first client application, determining a context associated with the task request message, and routing, based at least in part on the context associated with the task request message, the task request message to a selected task flow of a plurality of task flows associated with the computing resource. A response message is thereafter received from the computing resource. The response message is generated by the computing resource in response to the task being executed by processing steps of the task by the selected task flow. The response message has a payload content including a set of configuration parameters that define a layout of the payload content. The response message is then provided to one or both of the first client device and the second client device. Providing the response message to one or both of the first client device and the second client device causes the payload content of the response message to be displayed on one or both of a first client device display and a second client device display according to the configuration parameters and the capabilities of the first client device and the second client device.

In some embodiments, the payload content of the response message is simultaneously displayed on the first client device display and the second client device display, and a change in the state of the first client application or the second application resulting from an interaction of the end user with the payload content is also applied to the other of the first application and the second application.

In some embodiments, the first client device and the second client device each subscribe to receive notifications from the computing resource, and the computing resource publishes a notification to the first client device and the second client device any time a client device is registered with or unregistered from the computing resource.

In some embodiments, the first client device is a handheld mobile computing device, the first client application is a mobile client application, the second client device is a desktop computing device, and the second client application is a desktop client application.

In some embodiments, the first registration request message received from the mobile computing device is generated in response to scanning, with a camera of the mobile computing device, a barcode or a quick response code displayed on the display of the desktop computing device.

In some embodiments, the end user interaction with the mobile client application initiates a dictation operation during which speech of the end user is captured by a microphone of the mobile computing device, the selected task flow receives the speech and transcribes the speech into text, and the text is included in the payload content of the response message.

In some embodiments, the end user interaction with the mobile client application includes a natural language utterance requesting medical information for a patient. The selected task flow is associated with a generative artificial intelligence model that receives the natural language utterance, interprets the natural language utterance using one or more natural language processing techniques, and resultantly causes the selected task flow to retrieve the medical information. The response message is then generated by the generative artificial intelligence model, and the medical information is included in the payload content of the response message.

In some embodiments, the end user interaction with the mobile client application initiates an ambient recording operation during which the selected task flow of the computing resource is caused to listen to a conversation between the end user and a medical patient using a microphone of the mobile computing device. The selected task flow generates a medical note based on the conversation, and the medical note is included in the payload content of the response message.

Some embodiments include a system that includes one or more processing systems and one or more computer-readable media storing instructions which, when executed by the one or more processing systems, cause the system to perform part or all of the operations and/or methods disclosed herein.

Some embodiments include one or more non-transitory computer-readable media storing instructions which, when executed by one or more processing systems, cause a system to perform part or all of the operations and/or methods disclosed herein.

The techniques described above and below may be implemented in a number of ways and in a number of contexts. Several example implementations and contexts are provided with reference to the following figures, as described below in more detail. However, the following implementations and contexts are but a few of many.

BRIEF DESCRIPTION OF THE DRAWINGS

Features, embodiments, and advantages of the present disclosure are better understood when the following Detailed Description is read with reference to the accompanying drawings.

DETAILED DESCRIPTION

Figure 1:
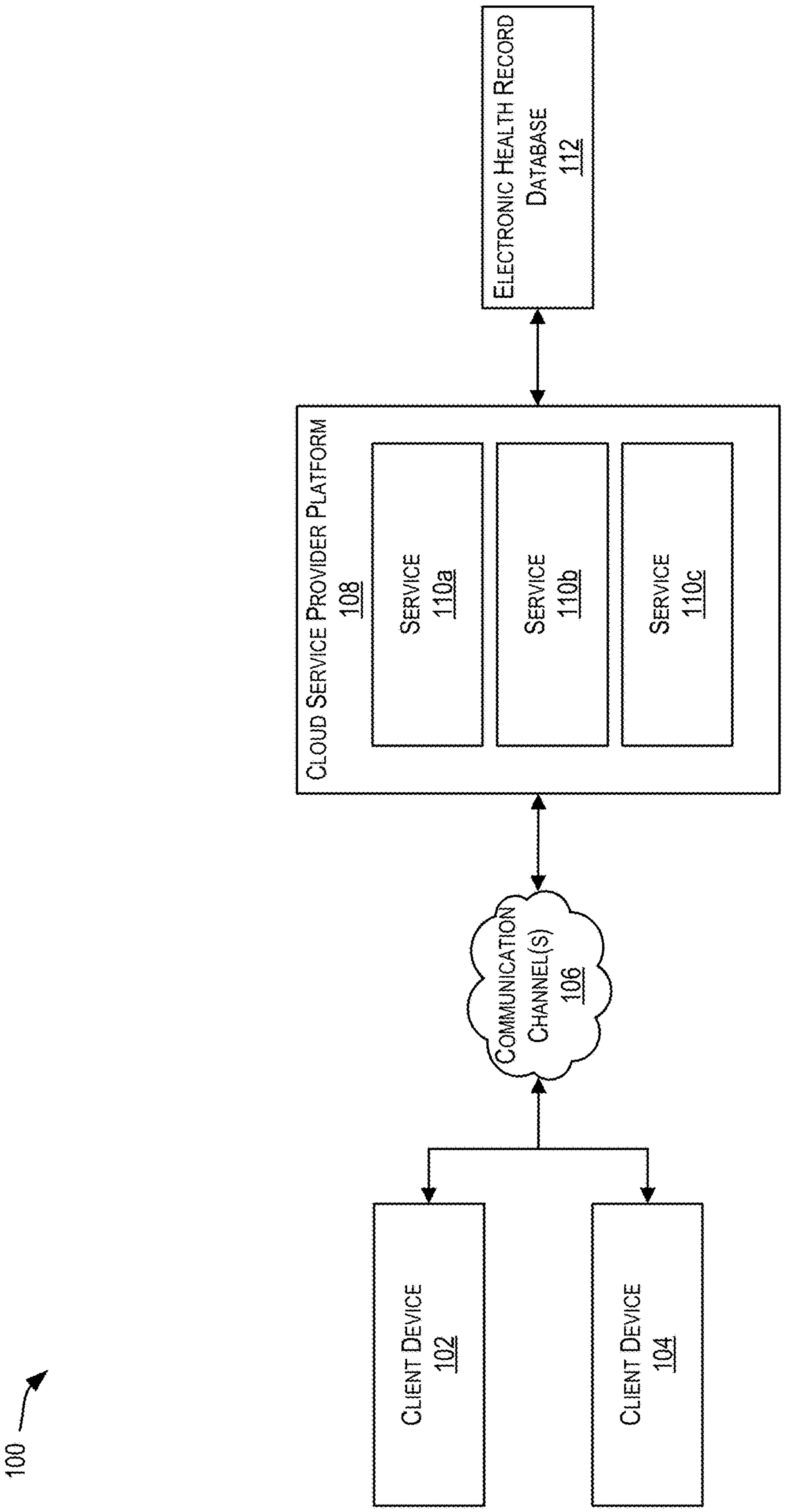
FIG. 1 is an example of a healthcare environment that includes capabilities for providing various services to healthcare providers to facilitate care and management of their patient populations, according to certain embodiments.

In the following description, for the purposes of explanation, specific details are set forth in order to provide a thorough understanding of certain embodiments. However, it will be apparent that various embodiments may be practiced without these specific details. The figures and description are not intended to be restrictive. The word "exemplary" is used herein to mean "serving as an example, instance, or illustration." Any embodiment or design described herein as "exemplary" is not necessarily to be construed as preferred or advantageous over other embodiments or designs.

Providing healthcare to patients typically requires a healthcare provider to repeat a number of common tasks for each patient. For example, regardless of the specific reason for an interaction between a healthcare provider and a patient, or the condition of a given patient, the healthcare provider must typically document the patient interaction. For example, the healthcare provider may record the patient interaction in a subjective, objective, assessment, and plan (SOAP) note, or may enter information gained during the patient interaction into a patient record. The healthcare provider may also engage in various other tasks directly or indirectly related to administering healthcare to the patient, such as requesting additional patient information in the form of charts or images, calling in patient prescriptions, and calendaring future tasks, events, and associated reminders.

Performing such healthcare tasks according to known and commonly used methods can be time consuming. In fact, given the typically high volumes of patient encounters, healthcare providers often spend a considerable portion of their workday documenting patient interactions and associated medical information, which reduces the amount of time available to the healthcare provider to administer actual patient care or perform other more critical tasks. For example, healthcare providers may spend considerable time on a daily basis typing or manually entering patient information into electronic health record (EHR) systems. In addition to being time consuming, this process can be, tedious, and prone to errors such as but not limited to typographical errors, which can result in inaccuracies and inconsistencies in patient records, and can potentially compromise patient safety and the quality of care provided. Traditional EHR systems can also have complex interfaces any may be difficult to navigate, which can increase the time required for healthcare providers to complete such repetitive tasks and generally frustrate the process Traditional EHR system devices may also be cumbersome to operate, and a lack of intercommunication between such devices prevents a healthcare provider from switching between devices while in the process of performing a task even if doing so would be more efficient. These issues may negatively affect patients as well as healthcare providers. For example, patient information may often be retrieved for review or discussion during a patient interaction or recorded during a patient interaction to ensure accuracy. When the process for retrieving or recording such information is inefficient, as is often the case when performed using traditional systems and methods, it can disrupt the natural flow of the patient interaction and may result in a less seamless and less fulfilling experience for the patient. The tedium and time requirements associated with repetitively performing these tasks can also contribute to healthcare provider burnout.

The developed approach described herein addresses these challenges and others by providing techniques for assisting healthcare providers with necessary but time consuming and sometimes tedious tasks. Techniques are disclosed herein for improving the efficiency of and reducing the computing resources required to perform various healthcare services in a clinical environment. In certain embodiments, techniques are disclosed for equipping a healthcare provider end user with a clinical software application that can be installed on and utilized from one or both of a mobile computing device and a desktop computing device to facilitate performance of the various tasks typically rendered by a healthcare provider as part of providing healthcare services to patients. For example, embodiments of the application may enable an end user to easily record conversations with patients, dictate in natural language, generate patient notes, populate patient records, request and receive patient information, fill prescriptions, create or have automatically created task and event reminders, and receive associated notifications. In some embodiments, the mobile computing application and the desktop computing application can be paired and subsequently controlled remotely by a cloud service provider platform, such that the effect of user interactions with an application on one of the mobile computing device or the desktop computing device will automatically be applied to the application on the other of the mobile computing device and the desktop computing device. This can allow an end user to seamlessly transition back-and-forth between the mobile computing device and the desktop computing device when interacting with a cloud service provider platform while performing a task. For example, the end user can begin a task on the mobile computing device, pick up the task on the desktop computing device from the exact location where the end user left the task on the mobile computing device, and then complete the task on the desktop computing device. All state and other updates to the mobile client application and the desktop client application to facilitate such a seamless transition between computing devices is managed by the cloud service provider platform.

Introduction

FIG. 1 is an example of a healthcare environment 100 that includes capabilities for providing various services to healthcare providers to facilitate care and management of their patient populations, according to certain embodiments. The term healthcare provider generally refers to healthcare practitioners and professionals including, but not limited to: physicians (e.g., general practitioners, specialists, surgeons, etc.); nurse professionals (e.g., nurse practitioners, physician assistants, nursing staff, registered nurses, licensed practical nurses, etc.); other professionals (e.g., pharmacists, therapists, technicians, technologists, pathologists, dietitians, nutritionists, emergency medical technicians, psychiatrists, psychologists, counselors, dentists, orthodontists, hygienists, etc.).

The healthcare environment 100 includes a cloud service provider platform 108 that includes capabilities for providing various services to subscribers (e.g., end-users) of the cloud service provider platform 108. The end-users (e.g., clinicians such as doctors and nurses) may utilize the various services provided by the cloud service provider platform 108 to perform various functions involving the treatment, care, observation, and so on of patients. For instance, in the healthcare environment 100, the end-users can utilize the functionality provided by the services to view, edit, or manage a patient's electronic health record, perform administrative tasks such as scheduling appointments, manage patient populations, provide customer service to facilitate operation of the healthcare environment 100, and so on.

The services provided by the cloud service provider platform 108 may include, but are not limited to, digital assistant services, authentication services, user management services, frontend services (e.g., entry point (façade) to all services), and other management services. The various services may be implemented on one or more servers of the cloud service provider platform 108 and may be provided to end-users who subscribe to the cloud services provided by the platform 108. In a certain implementation, the services provided by the cloud service provider platform 108 may represent digital assistant services that may be provided to healthcare providers such as doctors, nurses, technicians, clinicians, medical personnel, and the like. For instance, the service 110*a* may represent an ambient service, which is an AI-powered, voice-enabled service that automatically documents patient encounters accurately and efficiently at the point of care and provides quick action suggestions. The service 110*b* may represent a dictation service 110*b* that allows doctors to generate medical records from voice (e.g., using a Large Language Model (LLM) or pre-seeded templates). The service 110*c* may represent a clinical automation service where healthcare providers can interact with the digital assistant, and the digital assistant can provide the end user with support for various clinical functional tasks.

Various end-users may interact with the cloud service provider platform 108 using one or more client devices (e.g., 102, 104) that may be communicatively coupled to one or more servers implemented by the services (e.g., 110*a*, 110*b*,

110*c*), via one or more communication channels 106. The client devices (102, 104) may be of various types, including but not limited to, a mobile phone, a tablet, a desktop computer, and the like. The users can interact with the various services via a user interface (UI) of an application installed on the client devices (102, 104) to obtain information about a patient such as medical information from an electronic health record for the patient stored in the electronic health record database 210, collect information relevant to the observation, care, treatment, and/or management of a patient, and so on.

In certain embodiments, the applications installed on the client devices 102, 104 can support multimodal communications between an end user and the client devices 102, 104. For example, the end user can communicate with and utilize the functionality provided by services (110*a*, 110*b* and 110*c*) via audio, voice (natural language), text, or rich user interface controls. For instance, an end user may utilize one or more voice interfaces provided by an application installed on one of the client devices 102, 104 to interact with the services 110*a*, 110*b* and 110*c*. In another example, the end user can interact with the application based on touch input (e.g., tapping, swiping, pinching) and voice input captured by the client device to obtain information about a patient. Voice interactions can be initiated via a wake word or by tapping a dedicated button on screen. The application can interface with the various services which can generate conversational-type responses to the voice-based interactions. In some implementations, the responses can be natural language responses and/or graphical responses. As part of a conversation with the digital assistant, an end user may provide a voice input (e.g., a natural language utterance) to one of the services 110*a*, 100*b*, 110*c*. The platform 108 may include the capability to transcribe the voice input into text using various speech-to-text processing techniques. Components of the platform 108 may then process and determine the meaning of the text by applying natural language understanding (NLU) and/or natural language processing (NLP) techniques thereto, and subsequently provide a response to the user which may be or may include a textual or audible natural language response. In one example, a user may utilize the clinical automation service (110*c*) to perform various clinical tasks via natural language-based conversations therewith.

The healthcare environment 100 additionally includes an electronic health record database 112. The database 112 may be a storage device managed by a healthcare provider and/or stored remotely such as in a cloud-based server or remote database managed by the cloud service provider platform 108. The database 112 may be configured to store electronic health information related to patients. Each electronic health record associated with a patient can be linked to other electronic health records associated with the patient. For example, one healthcare provider such as a family physician may generate an electronic health record for a patient and store that electronic health record in a local database and another healthcare provider such as a hospital may generate an electronic health record for the patient and store that electronic health record in a cloud-based database. The two electronic health records for the patient can be linked to the patient using an identifier for the patient such as a portion of the patient's personally identifiable information.

The healthcare environment 100 depicted in FIG. 1 is merely an example and is not intended to unduly limit the scope of claimed embodiments. One of ordinary skill in the art would recognize many possible variations, alternatives, and modifications. For example, in some implementations, the healthcare environment 100 can be implemented using more or fewer services than those shown in FIG. 1, may combine two or more services, or may have a different configuration or arrangement of services.

In various embodiments, a method includes receiving a first registration request message from a first client application executing on a first client device. The first registration request message includes information that at least identifies the first client device and capabilities of the first client device. The method also comprises receiving a second registration request message from a second client application executing on a second client device. The second registration request message includes information that at least identifies the second client device and capabilities of the second client device. The first client application is paired with the second client application upon registering the first client device and the second client device with a computing resource. The method additionally includes receiving, from the first client device in response to an end user interaction with the first client application, an identification of a state of the first client application and a task request message corresponding to a task to be performed by the computing resource.; The method further comprises synchronizing a state of the second client application with the state of the first client application, determining a context associated with the task request message, and routing, based at least in part on the context associated with the task request message, the task request message to a selected task flow of a plurality of task flows associated with the computing resource. A response message is thereafter received from the computing resource. The response message is generated by the computing resource in response to the task being executed by processing steps of the task by the selected task flow. The response message has a payload content including a set of configuration parameters that define a layout of the payload content. The response message is then provided to one or both of the first client device and the second client device. Providing the response message to one or both of the first client device and the second client device causes the payload content of the response message to be displayed on one or both of a first client device display and a second client device display according to the configuration parameters and the capabilities of the first client device and the second client device.

As used herein, when an action is "based on" something, this means the action is based at least in part on at least a part of the something. As used herein, the terms "similarly," "substantially," "approximately" and "about" are defined as being largely but not necessarily wholly what is specified (and include wholly what is specified) as understood by one of ordinary skill in the art. In any disclosed embodiment, the term "similarly," "substantially," "approximately," or "about" may be substituted with "within [a percentage] of" what is specified, where the percentage includes 0.1, 1, 5, and 10 percent.

Cloud Service Provider Platform and Clinical Digital Assistant

Figure 2:
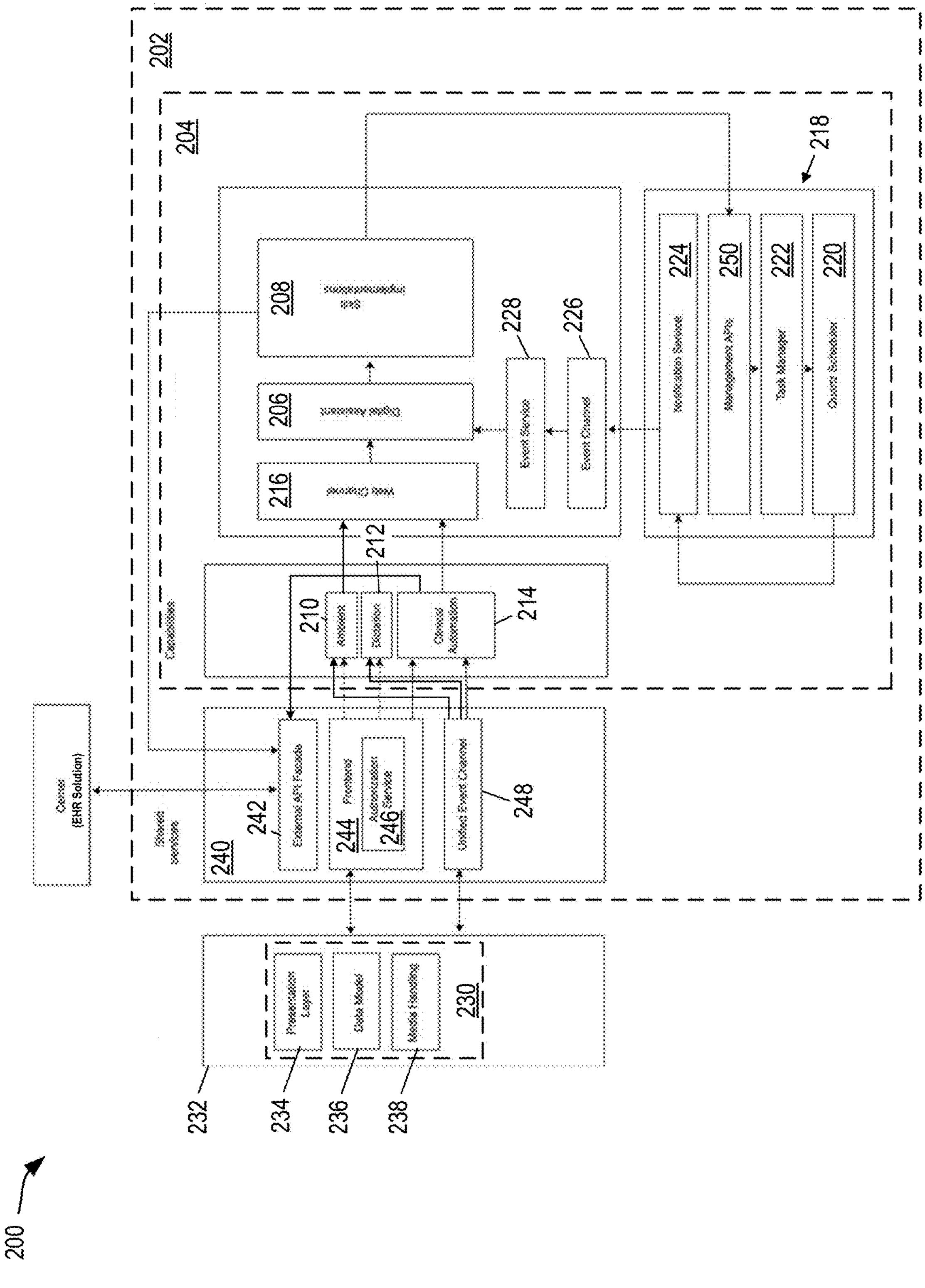
FIG. 2 depicts a simplified architectural diagram of a cloud service provider platform of the healthcare environment of FIG. 1, according to certain embodiments.

FIG. 2 is a high-level architectural diagram of one embodiment of a system 200 for facilitating healthcare provider tasks. The system 200 is shown to include a cloud service provider platform 202 that may be the same as or similar to the cloud service provider platform 108 described above relative to the healthcare environment 100 of FIG. 1, and an application 230 installed on a client device 232 which may be the same as or similar to the one of the client devices 102, 104 of FIG. 1.

As described in more detail below, embodiments of the cloud service provider platform 202 can be configured to have an artificial intelligence-driven (AI-driven) conversational-type interface that can conduct conversations with end users (e.g., those using the client devices) and perform functions and/or tasks based on the information conveyed by and/or ascertained from those conversations and other sources. The cloud service provider platform 202 can be configured with and/or configured to access natural language understanding (NLU) capabilities such as natural language processing, named entity recognition, intent classification, and so on. In some implementations, the cloud service provider platform 202 can include a skill-driven digital assistant 206 that includes a plurality of bots that each include one or more skills for conducting conversations and performing functions and/or tasks. In some implementations, the digital assistant 206 can instead be LLM-based and agent-driven, with agent(s) coordinating with LLM(s) for conducting conversations and performing functions and/or tasks. Examples of skill-driven and LLM-based and agent-driven digital assistants are described in U.S. patent application Ser. No. 17,648,376, filed on Jan. 19, 2022, and U.S. patent application Ser. No. 18/624,472, filed on Apr. 2, 2024, each of which are incorporated by reference as if fully set forth herein.

As shown in FIG. 2, the cloud service provider platform 202 can include a backend 204 that implements the digital assistant 206 and provides a plurality of different implementation skills ("skills") 208. The skills 208 (e.g., bots, chatbots) include the logic required to process specific tasks such as, for example, ordering medication, retrieving patient information, generating SOAP notes, and scheduling events or tasks and associated notifications for the end user. Each skill 208 is associated with a task flow by which steps of a task can be processed by the skill.

The backend 204 of the cloud service provider platform 202 can also include a plurality of capabilities (services) which, in this particular embodiment, include an ambient recording capability 210, a dictation capability 212, and a clinical automation capability 214. The ambient recording service 210 may, for example, be used to record and subsequently transcribe a spoken conversation between a healthcare provider and a patient into text. The text can then be used, for example, to generate textual patient notes (e.g., SOAP notes) for a healthcare provider. The dictation service 212 may be usable to, for example, dictate terms that can be used to automatically populate various forms, such as healthcare forms. The clinical automation service 214 can be used to facilitate natural language conversations between a healthcare provider and the digital assistant 208, such as but not limited to for purposes of retrieving patient information. Clinical automation conversations between an end user and the digital assistant 208 may occur via a web channel 216, as shown. In some embodiments, each of the services 210, 212, 214 can be facilitated by a corresponding skill of the plurality of skills 208.

The backend 204 of the cloud service provider platform 202 may further include a task manager and notification service layer 218. The task manager and notification service layer 218 may allow an end user to create, or have automatically created, reminders of events or tasks, and to subsequently receive notifications upon the occurrence of a time of an event or a time to perform a task. The task manager and notification service layer 218 can include a scheduler 220 service that operates to schedule the events or reminders and a task manager service 222 that includes various task management APIs for performing functions such as creating, updating, and deleting tasks. The task manager service 222 may also allow each consuming service to configure a channel by which to receive notifications. A notification service 224 of the task manager and notification service layer 218 is also present and can operate to manage the generation of notification messages when an event or a task becomes due. Upon occurrence of a criteria for initiating a given scheduled task, the notification service 224 can communicate with the digital assistant 206 via an event channel 226 and through an event service 228, such that a notification can be generated by a skill 208 of the digital assistant 206 that is appropriate to the given task and subsequently transmitted to a client device for display to an end user. The task manager and notification service layer 218 may also include one or more management APIs 250 that may perform management/administrative functions related to, for example and without limitation, global application settings, feature flag configurations, and metadata management.

As referenced above and described in more detail below, the application 230 displays on the client device 232 at the direction of one or more of the plurality of skills 208 of the backend 204 of the cloud service provider platform 202, various user interfaces via which an end user healthcare provider can interact with one or more of the skills 208 to perform various clinical tasks. In this particular embodiment of the application 230, an application framework includes a presentation layer 234, a data model layer 236, and a media layer 238. The presentation layer 234 can interpret messages sent by the clinical automation service 214. The data model layer 236 can function as a binding model between user interface (UI) fields and data contained in response messages sent to the client device 232 by the backend skills 208. The media layer 238 can be used, at least from a clinical automation perspective, for voice, audio and event support.

The cloud service provider platform 202 also includes a shared services component 240 that facilitates, among other things, authorizing client devices to access the cloud service provider platform 202, and an exchange of messages between client devices executing client applications and the skills 208 of the cloud service provider platform 202 backend 204. To this end, the shared services component 240 may include an external API facade 242. Except for reminders associated with the task manager and notification service layer 218, all API calls may use the external API facade 242 as a shared API service. The external API facade 242 can abstract clinical automation from an EHR solution (e.g., Cerner). The external API facade can also protect the clinical automation capability from API changes that occur outside of the cloud service provider platform 202 infrastructure, and may provide a zero-query access to information about a current healthcare provider, appointments, patients associated with those appointments, locations, and other information that can be used to populate a client application home screen that may provide a healthcare provider end user with a quick overview of important information (according to the healthcare provider).

The shared services component 240 can also include a frontend service 244 that is exposed to the client device 232. The frontend service 244 is an API service that can implement REST APIs for client applications (e.g., for configuring preferences, activating features, etc.). The frontend service 244 is also a shared service that dispatches messages and streams directed from the client application 230 to the capabilities 210, 212, 214 of the cloud service provider platform 202 backend 204. The frontend service 244 can serve as the entry point to all system services. For example, the client application 230 may go through the frontend service 244 to avail itself of any service of the cloud service provider platform 202. The frontend service 244 may include an authorization service 246. The authorization service 246 can facilitate authorization of the client device 232 (and the end user) to access and utilize the services of the cloud service provider platform 202. The frontend service 244 and the associated authorization service 246 can ensure that end user sessions get created and that the sessions are authenticated and authorized. For example, the frontend service 244 can ensure that a clinical automation operation is provided a valid session with all the information required to pass along when invoking protected services through the external API facade 242, which can relieve the clinical automation operation from the requirement to handle user login and session management.

The shared services component 240 is also shown to include a unified events channel 248, which is a cloud service of the cloud service provider platform 202 and can e the aforementioned bidirectional transfer of messages between client facilitate devices/applications and the skills 208 of the cloud service provider platform 202 backend 204. The unified events channel 248 can provide a WebSocket interface by which audio, conversational text, and event traffic can flow to and from the client application 230. For example, audio and conversation text received from the applications can be routed by the unified events channel 248 to the ambient 210, dictation 212, and clinical automation 214 services of the cloud service provider platform 202.

All communications from the client application 230 to the cloud service provider platform 202 and from the cloud service provider platform 202 (e.g., from a skill 208) to the client application 230 are in the form of messages. The messages may be in a conversation message model (CMM) format. The CMM format can represent a message to or from a bot and can serve as a unified representation of messages that can flow between the client application 230 and the cloud service provider platform 202. CMM messages can convey basic requests and responses, and can also convey information defining complex user interfaces. The CMM format can also define the various message types that a skill can send to a client application. These message types may include, for example, Text Message Payload, Postback Message Payload, Form Message Payload, Edit Form Message Payload, and Inbound Event Message Payload message types.

Client Applications

Applications installed on client devices (i.e., "client applications") are AI-enabled healthcare applications that are designed to help healthcare providers more efficiently perform the various repetitive tasks typically associated with delivering healthcare services to patients. For example, through use of a client application, a healthcare provider can quickly and efficiently access patient information on an as-needed basis (e.g., during a patient interaction), record details of patient interactions, generate patient notes, populate patient records, receive patient appointment schedules, schedule tasks and events, receive notifications about tasks and events that need to be performed, request and receive patient information including lab results, imaging results, lists of medications taken and medication allergies, and perform clinical functions such as ordering tests or prescribing medications. In some embodiments, such functions may be enabled via a natural language conversation with a digital assistant.

In various embodiments, a client application can be installed on a mobile computing device of an end user (as a mobile client application), a desktop computing device of an end user, (as a desktop client application), or on both a mobile computing device and a desktop computing device of an end user. The end user may be a healthcare provider. In some embodiments, the mobile computing device and the associated mobile client application may serve as the primary mechanism by which the healthcare provider interacts with the skills and services associated with a cloud service provider platform, including interactions with a digital assistant, while the desktop client application executing on the desktop computing device may serve as a companion application to the mobile client application.

As used herein, the term "mobile computing device" is intended to encompass handheld portable computing devices such as but not limited to smartphones and tablets that can easily be carried by a healthcare provider and used at virtually any location of the healthcare provider. Such mobile computing devices may execute mobile operating systems such as the iOS operating system from Apple™ or the Android operating system from Google™, although other mobile operating systems may instead be present on other mobile computing devices. As used herein, the term "desktop computing device" is intended to encompass computing devices such as personal computers, laptop computers, or similar computing devices that, even if technically mobile, are nonetheless of a size or configuration that would be too cumbersome to transport or would otherwise discourage a healthcare provider from carrying the computing device from one location to another. Such desktop computing devices may execute desktop operating systems such as Microsoft's Windows operating system, although other desktop operating systems may instead be present on other desktop computing devices. Client applications may be distributed to client devices through various channels, the type of which depends on whether the client application is a mobile client application or a desktop computing application. For example, mobile client applications may be distributed and updated through "app stores," such as Google Play™ for mobile computing devices equipped with an Android™ operating system and the Apple App Store™ for mobile computing devices equipped with an iOS™ operating system. Desktop client applications may be distributed, according to one embodiment, through a Citrix environment.

Whether installed on a mobile computing device or a desktop computing device, a client application can utilize various functionality afforded by the mobile computing device or the desktop computing device and its associated operating system. For example, when the client application is a mobile client application installed on a mobile computing device, the mobile client application may operate a sound recording device (e.g., microphone) and/or an image capture device (e.g., camera) of the mobile computing device. Likewise, when the client application is a desktop client application installed on a desktop computing device, the desktop client application may take advantage of the likely larger display of the desktop computing device for presenting patient imaging information (e.g., x-rays) to the healthcare provider.

Both a mobile client application and a desktop client application can be controlled by various skills of a digital assistant (e.g., the digital assistant 206 of FIG. 2) implemented in a backend portion (e.g., the backend 204 of FIG. 2) of a cloud service provider platform (e.g., the cloud service provider platform 202 of FIG. 2). For example, and as described in more detail below, a state of a mobile client application executing on a mobile computing device and a state of a desktop client application executing on a desktop computing device can be remotely controlled by the various skills of the digital assistant, and the client applications can be linked and synchronized such that an end user can move seamlessly between the mobile device and the desktop device while performing a given task.

Figure 3:
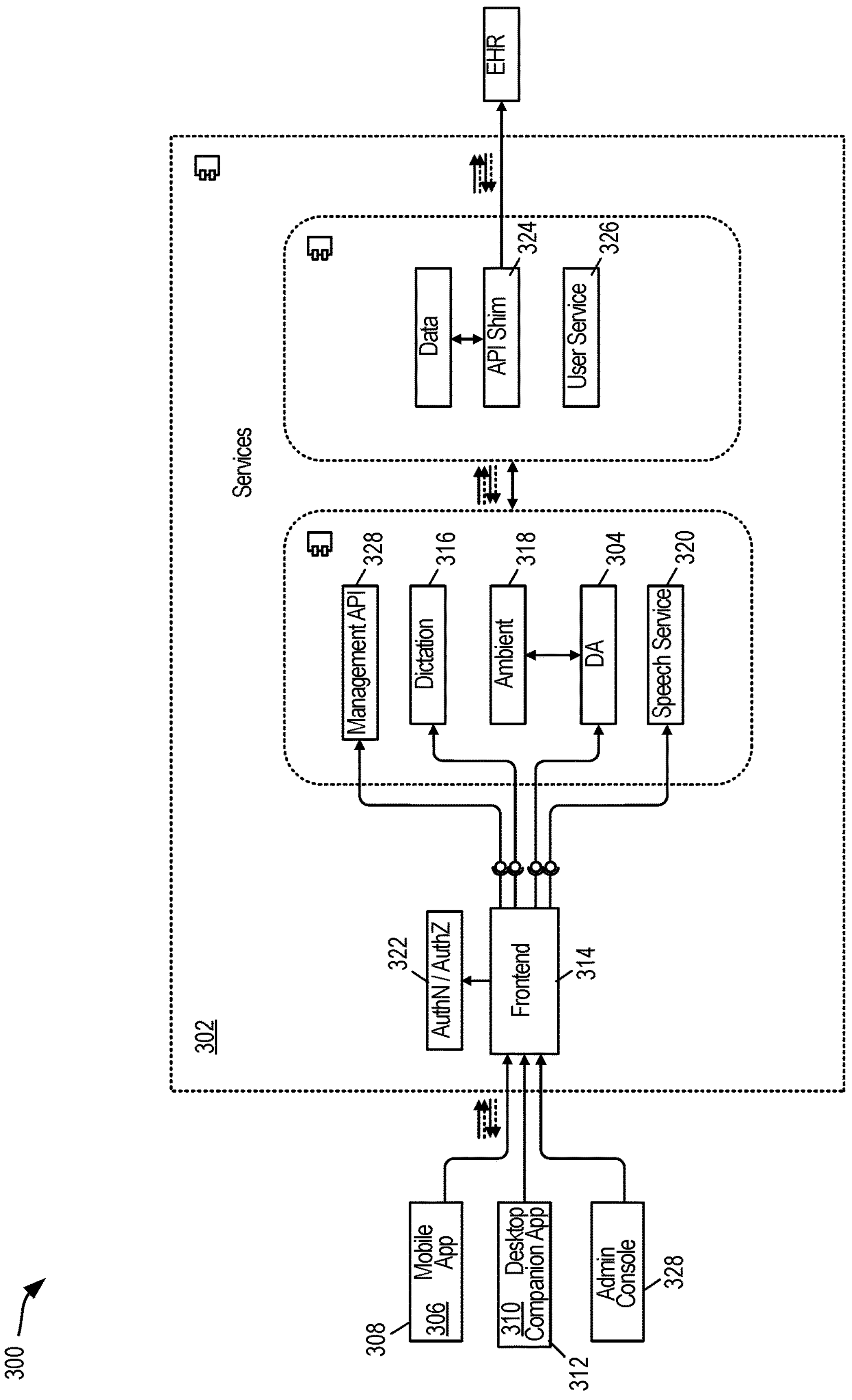
FIG. 3 is a high-level architectural diagram illustrating the interconnections and communication pathways between components of a cloud service provider platform and client application executing on client computing devices, according to certain embodiments.

FIG. 3 is a high-level architectural diagram 300 illustrating the interconnections and communication pathways between various components of a cloud service provider platform 302 implementing a digital assistant 304 and a mobile client application 306 executing on a mobile computing device 308 and a desktop client application 310 simultaneously executing on a desktop computing device 312. As previously described, the mobile client application 306 and the desktop client application 310 serve as end user-facing interfaces to the cloud service provider platform 302 and the associated digital assistant 304. Among other things, the client applications 306, 310 may operate to resolve the provider, authenticate the end user, establish an end user session, prepare the application runtime for interaction with backend services of the cloud service provider platform 302, display a home screen on the client devices 308, 312, and enable multimodal end user interactions with the client applications 306, 310.

The cloud service provider platform 302 can include a frontend service 314 that is exposed to the client devices 308, 312. The frontend service 314 may operate in the same or a similar manner to the frontend service 244 described above with respect to the cloud service provider platform 202 of FIG. 2. For example, the frontend service 314 can operate as the entry point to all system services and, as such, to dispatch messages and streams directed from the client devices 308, 312 to the digital assistant 304 and to various capabilities (services) of the cloud service provider platform 302. In this particular example, the services include a dictation service 316, an ambient recording service 318, and a speech service 320. These services are described in more detail below, but generally speaking: the dictation service allows healthcare providers to, for example, generate medical records from voice inputs using pre-seeded templates; the ambient recording service is an AI-powered and voice-enabled service that can automatically document healthcare provider interactions with patients accurately and efficiently at the point of care and can provide quick action suggestions; and the speech service is an AI-powered service that leverages automatic speech recognition (ASR) technology to transform audio-based content into text.

The cloud service provider platform 302 may also include an authorization service 322. The authorization service 322 can facilitate authorization of the client devices 308, 312 to access and utilize the services of the cloud service provider platform 302. In at least some embodiments, the authorization service 322 may be configured to work with supported Identity Providers (IDPs).

As shown, the services of the cloud service provider platform 302 may further include an API shim service 324 and a user service 326. The API shim service 324 can offer all required provider APIs required for building use cases, thereby eliminating any direct dependency on custom, healthcare provider-specific API interfaces. The user service 326 may provide end user management services for the cloud service provider platform 302, such as end user profile management services, user preference settings services, and so on. A management API 328 may also be present, and may perform management/administrative functions related to, for example, global application settings, feature flag configurations, and metadata management. A front-facing administration console 328 can provide an administrative user interface for managing, for example, end user sessions with the client applications 306, 310, metadata, client application settings (e.g., application feature management, end user profile/preferences). In some embodiments, the administration console 328 can be launched either directly in a web browser by entering a URL, or by selecting an administrator console user interface link presented by the client applications 306, 310 on the respective client devices 308, 312. In at least some embodiments, both end users and platform administrators may have access to the administration console 328. The administration console 328 may also provide a user interface by which the number of concurrent end user sessions with client applications can be managed. The concurrent session management mechanism of the administration console 328 can limit the number of available client application sessions a particular end user may have for a given tenancy.

Access to particular features and services of the cloud service provider platform 302 may be based on end user roles and capabilities of the client devices 308, 312. In order to implement such access control, the client applications 306, 310 may make calls to the user service 326 during a bootstrapping operation to determine end user capabilities (e.g., features accessible to the end user). Upon determining the end user capabilities, the client applications 306, 310 can render user interfaces on the client devices 308, 312 based on the end user capabilities. For example, if a standard user interface for end user interaction with the ambient recording service 318 includes selectable buttons, and the end user does not have a button selection capability, the ambient recording service user interface can be displayed on the client devices 308, 312 without buttons. In some embodiments, the client applications 306, 310 may also be configured with the ability to selectively restrict end user access to particular features and services of the cloud service provider platform 302.

Figure 4:
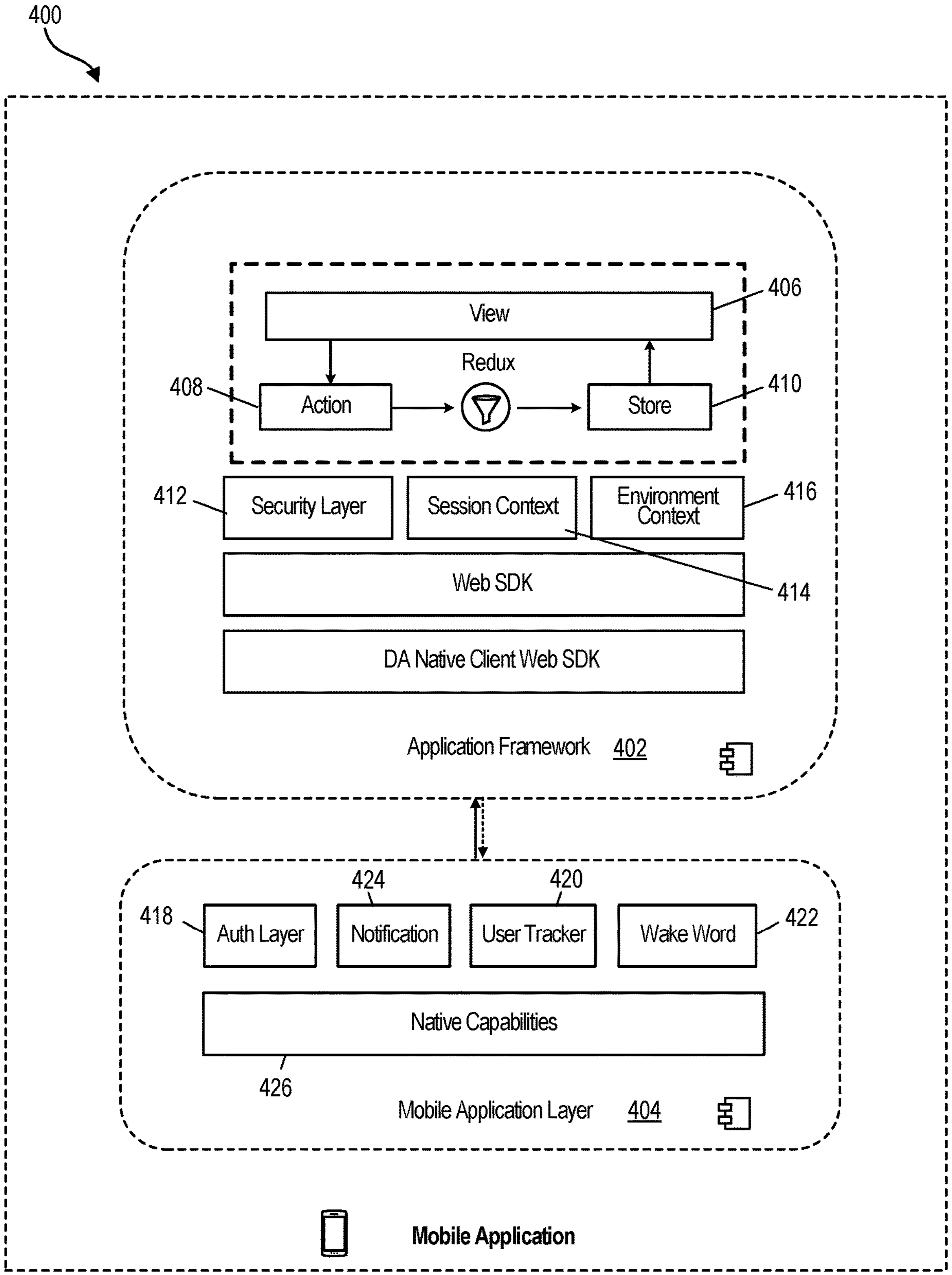
FIG. 4 depicts a framework for a mobile client application, according to some embodiments.

FIG. 4 depicts one embodiment of a framework 400 for a mobile client application, which may be the same as or similar to the mobile client application 306 of FIG. 2. The mobile client application framework 400 can be specially designed and configured to understand various enforceable contracts that govern interactions of the mobile client application and the backend of an associated cloud service provider platform, and may be used to rapidly build user interfaces for managing responses generated by various services or by various skills of a digital assistant implemented by the cloud service provider platform. In some embodiments, the mobile client application framework can be built using TypeScript and can then be transpiled into JavaScript.

This embodiment of the mobile client application framework 400 includes an application framework 402 and an associated mobile application layer 404. The application framework 402 can include several core components. As shown and described with respect to FIG. 2, for example, an application framework such as the application framework 402, can include a presentation (view) layer that can interpret response messages (e.g., CMM response messages) sent by a clinical automation service of a cloud service provider platform, a data model layer that can function as a binding model between user interface fields and data contained in response messages sent to client devices by backend skills of the cloud service provider platform, and a media layer that can be used, at least from a clinical automation perspective, for voice, audio and event support. A view layer 406 that can function to control the view (user interface) displayed on the mobile client device may be observed to also be a part of the application framework 402 in FIG. 4.

The framework embodiment of FIG. 4 is configured to allow a cloud service provider platform and services thereof to handle end user actions and to remotely (centrally) manage the application state by leveraging the Redux paradigm. With the Redux approach, views 406 are not burdened with complex business/communication logic. Instead, views 406 can gather data in the form of end user gestures (e.g., speaking, typing, tapping on buttons) and dispatch the same as actions 408 with payloads (i.e., the data associated with the gestures) to a Redux store 410. The view layer 406, the actions 408, and the Redux store 410 may all be associated with an application framework middleware layer. The middleware layer can process the actions and payloads to determine a single application state, thereby reducing two types of information into one (hence the use of the "Redux" descriptor). When response messages are eventually returned by the services of the cloud service provider platform to WebSocket connections managed by the middleware layer, the content of the response message payloads can also be dispatched as update actions to the client application state. The middleware layer may also include other logic, such as logic capable of transmitting a natural language utterance to a cloud service provider platform (e.g., to a digital assistant) through a WebSocket connection, retrieving transcribed utterances from a speech-to-text server, or generating an audible (verbal utterance) response by sending a textual input to a text-to-speech server. As described in more detail below, the centrally managed client application state allows an end user to move seamlessly between client devices when performing a clinical task.

As shown in FIG. 4, the application framework 402 may further include a security layer 412, a session context store 414, and an environment context store 416. The security layer 412 can enforce security rules at the application framework level, such as preventing unauthorized access to the capabilities of a cloud service provider platform, enforcing user role-based access, and so on. The session context store 414 can store on a client device, information related to an end user session with a client application installed on the client device. The environment context store 416 can store on the client device, environment and configuration information for the client device (which may be read from a server of the cloud service provider platform on startup of the associated client application).

A mobile client application can be built by adding the mobile application layer 404 on top of the application framework 402. As a result, the mobile application inherits all the capabilities offered by the application framework 402. The mobile application may be built for particular use and compatibility with Apple IOS and Google Android mobile device operating systems. As shown in FIG. 4, the mobile application layer 404 may include several core components. The core components may include, for example, an authentication layer 418 that provides end user login and logout capability, and a user activity tracker component 420 that can track user activities on a user interface of the mobile application and can lock the screen of the associated mobile device if screen inactivity is determined to exceed some predetermined amount of time (e.g., 15 minutes to comply with HIPAA requirements). The core components may also include a wake word module 422 that enables an end user to make voice inputs to the mobile client application after speaking a wake word (e.g., "Hey, Oracle"). Wake word detection can be performed locally via a learning model that runs on the computing device to which the mobile client application is installed. The core components may additionally include a notification layer 424 that can manage notifications generated by a service/digital assistant skill of a cloud service provider platform, such as push notifications or offline notifications. The core components may additionally include a native capabilities layer 426 that can offer native client device capabilities, such as for example, use of a microphone, a camera, or a WebSocket. In some embodiments, utilization of the native client device capabilities may be enabled via Cordova plugins.

Figure 5:
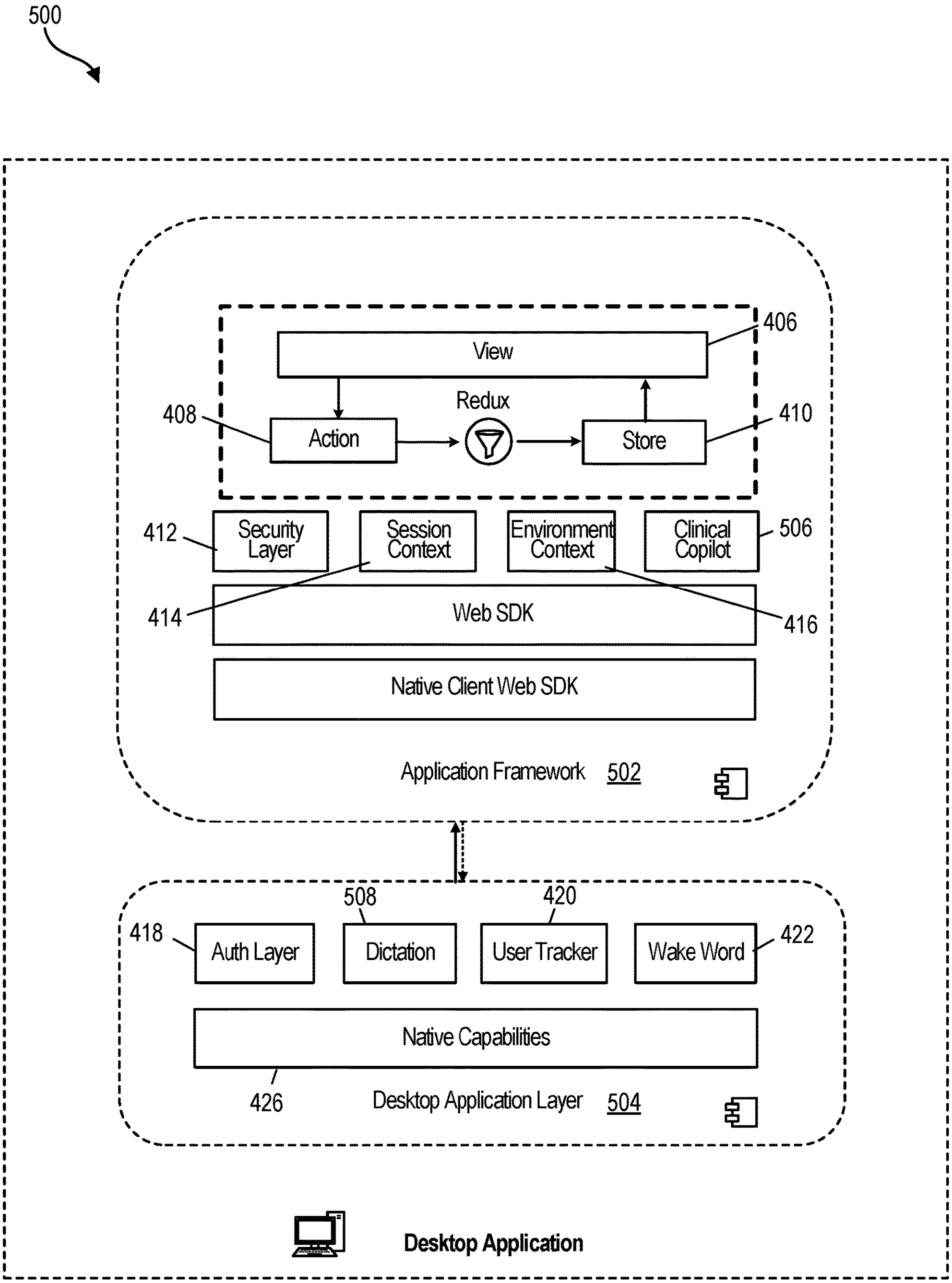
FIG. 5 depicts a framework for a desktop client application, according to some embodiments.

FIG. 5 depicts one embodiment of a framework 500 for a desktop client application, which may be the same as or similar to the desktop client application 310 of FIG. 2. This embodiment of the desktop client application framework 500 includes an application framework 502 and an associated desktop application layer 404. The application framework 502 can include various core components. Many of the core components of the application framework 502 are the same as those shown and described relative to the application framework 402 of FIG. 4. The core components of the application framework 502 that are duplicative of the core components of the application framework 402 of FIG. 4 are labeled in FIG. 5 with the same reference numbers used in FIG. 4. Each of the duplicative core components of the application framework 502 of FIG. 5 perform the same functions as described above relative to the application framework 402 of FIG. 4, and those functions are not described again relative to the application framework 502 of FIG. 5. All other functionalities and capabilities, etc., of the application framework 402 of FIG. 4 described above also apply to the application framework 502 of FIG. 5. Unlike the application framework 402 of FIG. 4, the application framework 502 includes an additional core component in the form of a clinical Copilot component 506. The clinical Copilot component can enable developers to integrate Microsoft Copilot™ features with the desktop client application, thereby allowing the desktop client application to leverage the power of the machine learning and large language models of the Copilot orchestration engine.

A desktop client application can be built by adding the desktop application layer 504 on top of the application framework 502. As a result, the desktop application inherits all the capabilities offered by the application framework 502. In some embodiments, the desktop client application may be built for particular use and compatibility with a Windows operating system. More specifically, some embodiments of the desktop client application can be built using the Windows Presentation Framework (WPF), which is a graphical user interface for Windows dot NET. The WPF application uses Microsoft Edge WebView2 control to embed the web view built using the application framework 502 container. In other words, the Web View2 control can integrate an application framework 502 created using JavaScript with the Windows native application runtime.

As shown in FIG. 5, the desktop application layer 504 may include many of the same core components as the mobile application layer 404. The core components of the desktop application layer 504 that are duplicative of the core components of the mobile application layer 404 of FIG. 4 are labeled in FIG. 5 with the same reference numbers used in FIG. 4. Each of the duplicative core components of the desktop application layer 504 of FIG. 5 perform the same functions as described above relative to the mobile application layer 404 of FIG. 4 and, therefore, those functions are not described again relative to the desktop application layer 504 of FIG. 5. All other functionalities and capabilities, etc., of the mobile application layer 404 of FIG. 4 described above also apply to the desktop application layer 504 of FIG. 5. As shown the desktop application layer 504 in this example also includes a dictation component 508 that allows an end user to utilize a dictation service of the cloud service provider platform to, for example, generate documents (e.g., electronic healthcare records) using voice inputs/commands.

Figure 6:
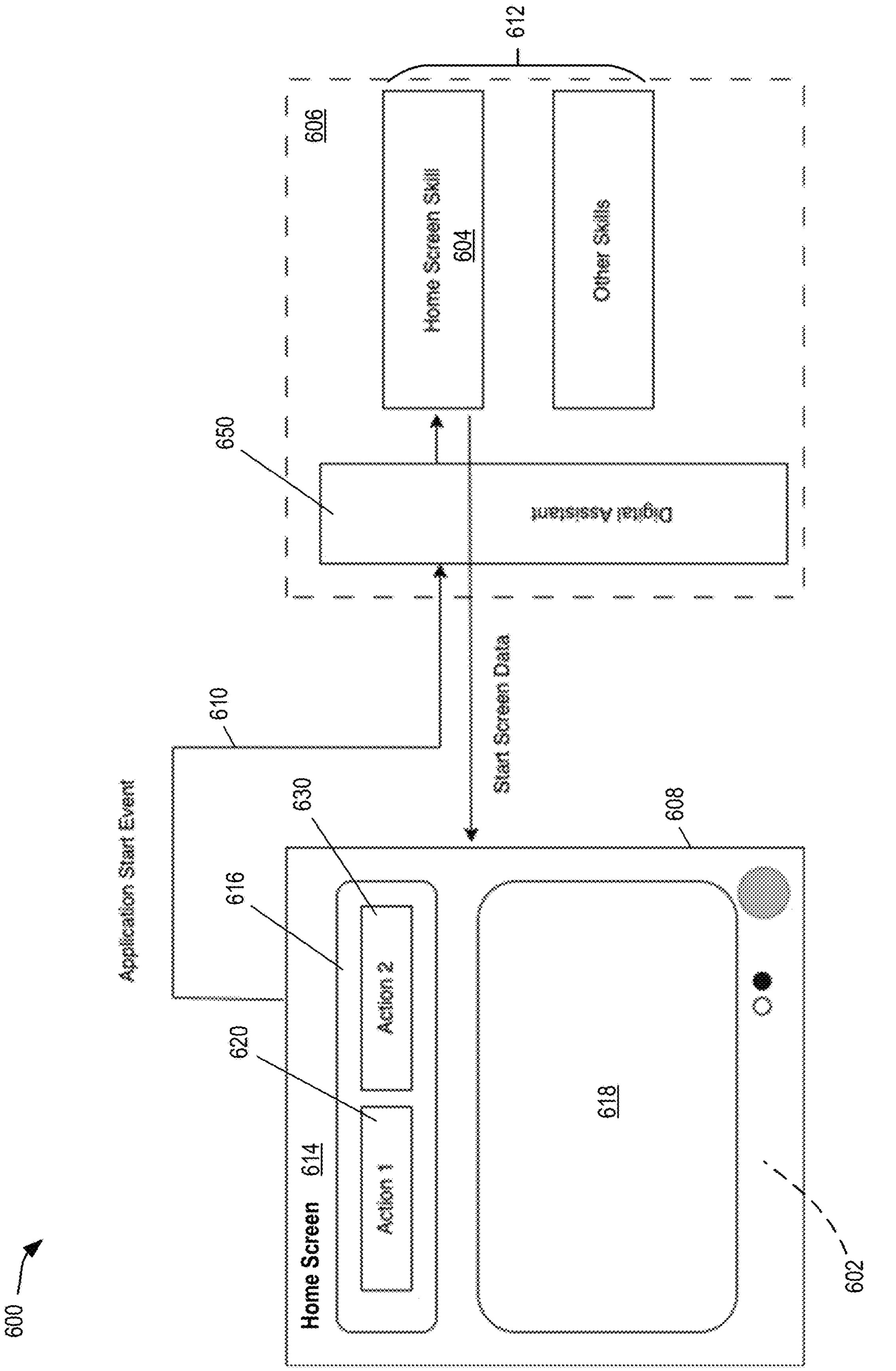
FIG. 6 is a simplified architectural diagram illustrating a dialog flow between a client application and a home screen skill of a cloud service provider platform during startup of the client application on a client device, according to some embodiments.

FIG. 6 is a simplified architectural diagram illustrating a dialog flow 600 between a client application 602 and a home screen skill 604 of a cloud service provider platform 606 during startup of the client application 600 on a client computing device 608. Generally speaking, at runtime, the client computing device 608 by way of the client application 602, send messages or events to the cloud service provider platform 606. Aside from the client application 602 sending a startup event upon initial startup, messages or events sent by the client application 602 may be driven entirely by the messages sent by a skill of the cloud service provider platform 606 to the client computing device 608.

As represented in FIG. 6, after startup of the client application 602 and any required authorization, authentication, etc., operations, an event notification 610 is received from the client computing device 608. The event notification 610 may be generated in response to the client application 602 installed on the client computing device 608 being granted access to a computing resource (the cloud service provider platform 606). The event notification 610 can be routed to the home screen skill 604 of a plurality of backend skills 612 of the cloud service provider platform 606. After receiving the event notification 610, a message can be provided to the client computing device 608 by the cloud service provider platform 606. The message can be generated by the home screen skill 604. The message may include a set of configuration parameters that may be generated by the home screen skill 604 or otherwise by another skill or component of the cloud service provider platform 606. The configuration parameters can be used by the client application 602 to display a first graphical user interface page on a display of the client computing device 608. The state of the client application 600 is updated accordingly. The first graphical user interface page may be a home screen 614. The configuration parameters may include information to be rendered on the home screen 614, such as for example, header greetings, starter actions, and/or cards presenting end user specific information.

The configuration of the home screen 614 may vary based on, for example, the end user and the specific (e.g., clinical) setting in which the client computing device 608 and associated client application 602 are being used. In some embodiments, the home screen 614 can include multiple widgets via which the end user can view new, important and time sensitive information at a glance. As used herein, the term "widget" is intended to describe a small user interface element that displays important and concise information. In some embodiments, a widget can be a client application user interface construct comprising read only data along with optional buttons or links. Some embodiments of the client application home screen 614 may include several types of widgets. Examples of such widgets may include a header, conversation starters area 616, and a key items display area 618 (which may provide information unique to the end user).

If the end user chooses to interact with a given widget, such as by engaging an action button 620, 630 of the conversation starters area 616, the widget can expand into a multimodal conversational view (e.g., task panel) to show more information or perform an action. The task panel may be an interactive modality of the skills 612 and may consist of various areas for providing information or facilitating end user interaction with the cloud service provider platform 606. In one embodiment, the task panel may include a task header, a task response area, and a task content area. Other task panel configurations are also possible.

Figure 7:
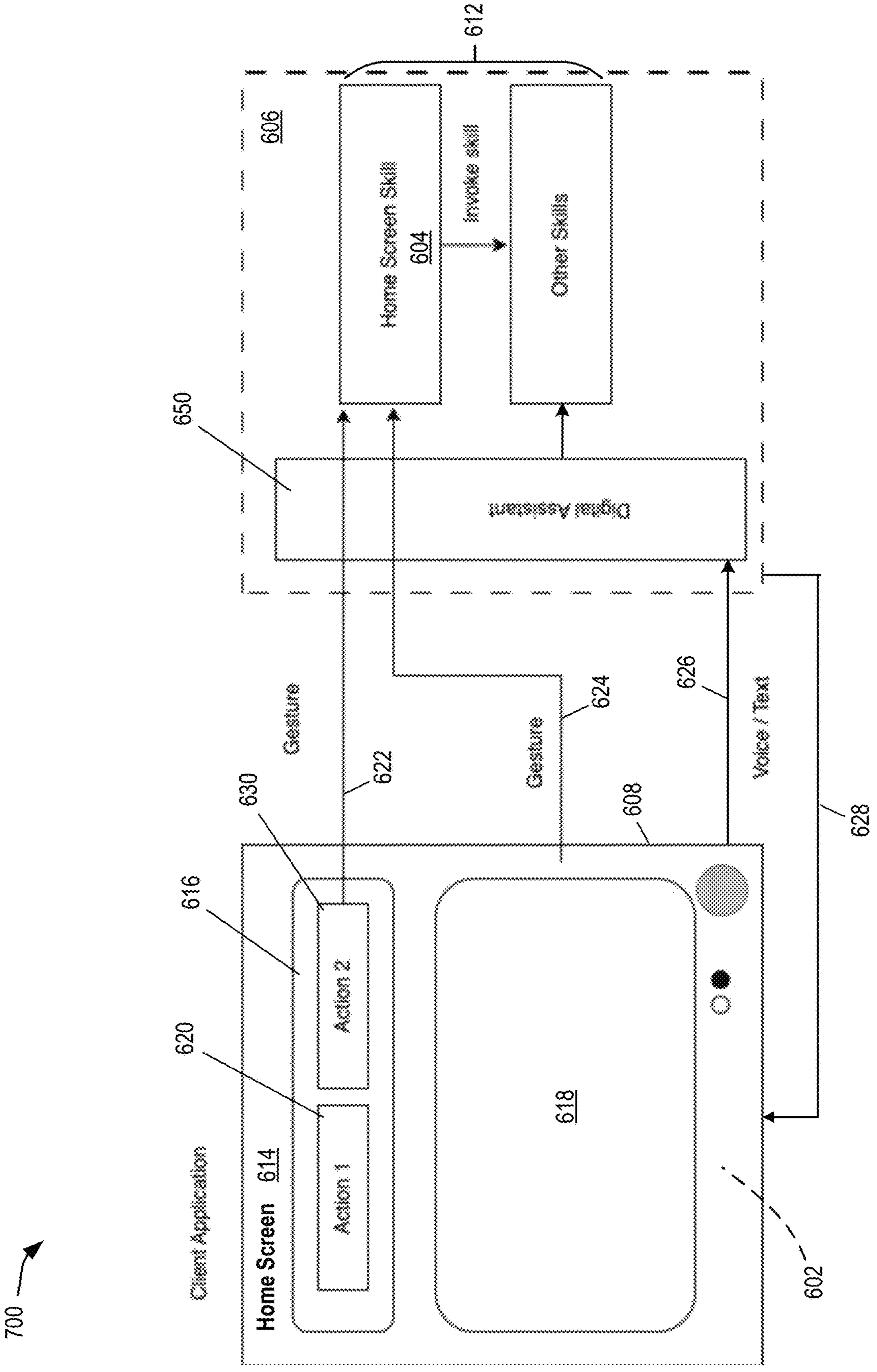
FIG. 7 is a simplified architectural diagram illustrating a further dialog flow between the client application and the cloud service provider of FIG. 6 subsequent to rendering of a home screen on the client device, according to some embodiments.

FIG. 7 is another simplified architectural diagram illustrating a further dialog flow 700 between the client application 602 and the cloud service provider platform 606 subsequent to rendering of the home screen 614 on the client computing device 608. For example, the further dialog flow may result from an interaction of the end user with a widget 616, 618, a notification, or with other information presented on the home screen 614.

Embodiments of the client application 602 can support multimodal end user input. Therefore, once the home screen 614 of the client application 600 has been rendered with widgets, data, etc., the end user can interact in various ways with the home screen 614 and other user interfaces and associated widgets, etc., subsequently displayed on the client computing device 608 to send messages carrying task requests to the cloud service provider platform 606. For example, the end user may engage in gesture-based interactions with the home screen 614 or another user interface screen displayed on the client computing device 608 by the client application 602. The gesture-based interactions may include, for example, a tap or click 622 of the action button 620, the action button 630, or another feature on the displayed user interface. The gesture-based interactions may also include typing 624 in a designated area of the user interface, such as within an area bounded by the widget 618.

Alternatively, the end user may engage in utterance-based interactions 626 with the home screen 614, or with another user interface screen displayed on the client computing device 608 by the client application 602 subsequent to the home screen 614. The end user may initiate an utterance-based interaction 626 with the client application 602 through voice or text such as, for example, by speaking a designated wake word/phrase (e.g., "Hey, Oracle"). The wake word may be spoken alone or the wake word may be included with a task request (e.g., "Hey, Oracle, order medication for patient X"). The spoken wake word is heard by a microphone of the client computing device 608, which may be configured in the settings to be always listening. The client application can utilize a native speech AI library to detect the wake word within an utterance of the end user, and can thereafter direct the utterance to a speech service of the cloud service provider platform 606 via a frontend service thereof. The speech service may employ automatic speech recognition (ASR) and/or other techniques to translate the utterance into text. When the utterance includes more than just the wake word, the translated text can be sent back to the client application 602. For example, during further speech by the end user, partial transcriptions may be continuously sent to a command text area of a client application 602 user interface displayed on the client computing device 608 to update the displayed transcription until completed transcription is finally displayed.

The end user can interact with the home screen 614 (or other user interfaces) presented by the client application 602 on the client computing device 608 to send task request messages to the cloud service provider platform 606. Therefore, the data flow 700 may further include receiving from the client computing device 608, a task request message associated with a task to be performed by the cloud service provider platform 606. The task request message may be generated by the client computing device 608 in response to an end user interaction with the first graphical user interface page or a subsequent graphical user interface page. As shown in FIG. 7, the task request may, in some embodiments, eventually be received by the home screen skill 604 of the cloud service provider platform 606. Upon receipt of the task request message, a context associated with the task request message can be determined, and the task request message can be routed, based at least in-part on the context associated with the task request message, to a selected task flow (of a service or skill) of a plurality of task flows (plurality of services or skills 612) associated with the cloud service provider platform 606. A response message 628 can be generated by the cloud service provider platform 606 in response to the task being executed by processing steps of the selected task, and the response message 628 can be received at, for example, a shared services portion (e.g., the unified event channel 248 of FIG. 2) of the cloud service provider platform 606. The response message 628 may include a payload having a content including a set of response configuration parameters that define a response layout of a second graphical user interface page of the client application. The response message 628 can then be provided to the client computing device 608. Providing the response message 628 to the client computing device 608 can cause the client application 602 to display a second graphical user interface page on the display of the client computing device 608 based at least in part on the response layout. In at least some embodiments, the client application 602 may cause the display of the client computing device 608 to return to the home screen 614 once the end user is done reviewing or interacting with the second graphical user interface page displayed upon receipt of the response message 628 from the cloud service provider platform 606. The home screen 614 may again display the previously displayed widgets 616, 618 or the home screen 614 can be updated to display some new widgets or to display completely different widgets.

Generally speaking, the payload content of a response message can inform a client application what to display and what to say. In addition to causing a client application to display a new (e.g., second) graphical user interface page on a client device, the payload content of a response message can also cause a corresponding change in state of the client application, where the new application state corresponds to and allows the end user to appropriately interact with the information displayed in the new graphical user interface page.

Figure 8:
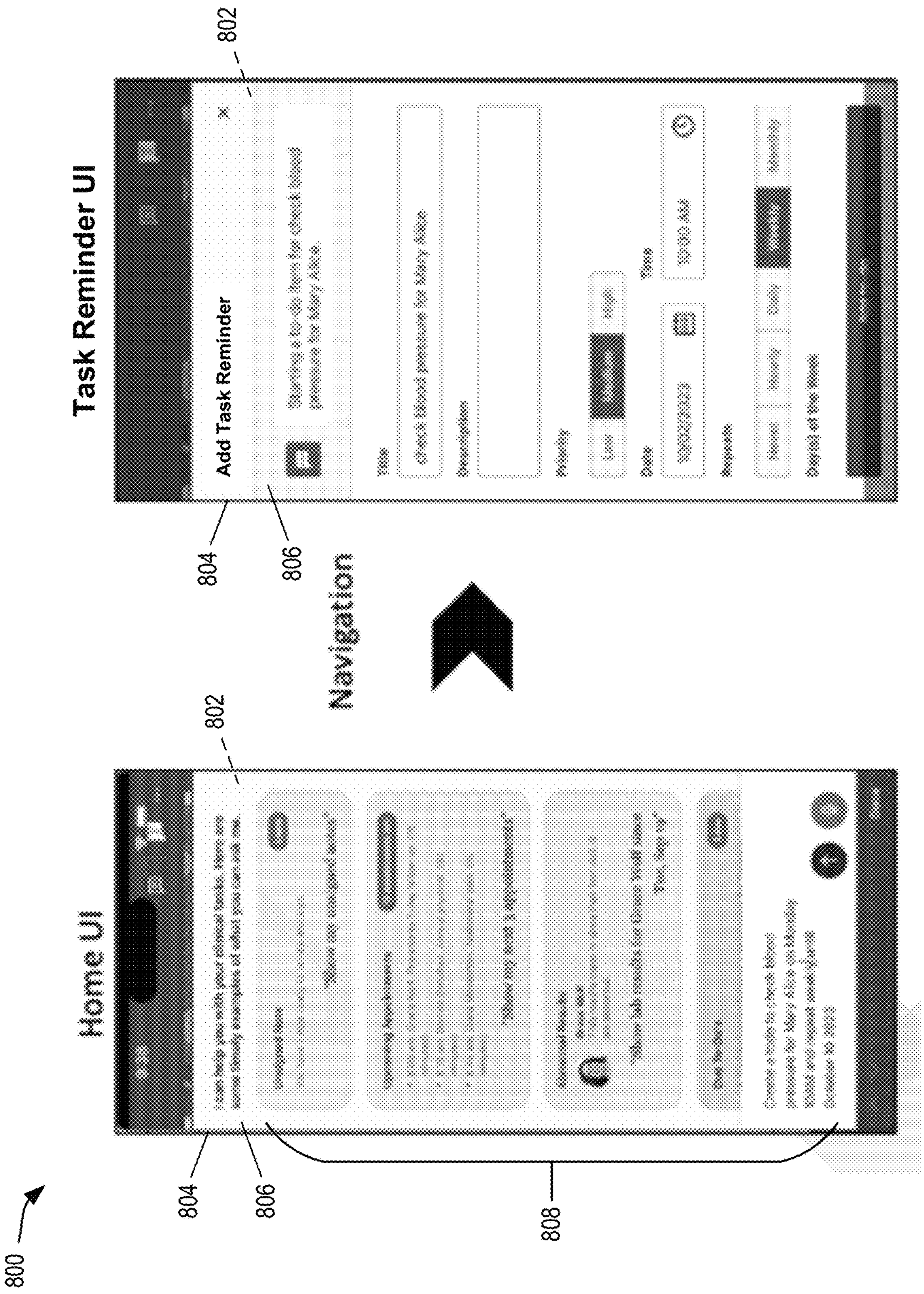
FIG. 8 depicts one example of a client application user interface and client application state transition flow, according to some embodiments.

FIG. 8 depicts one example of a user interface and application state transition flow 800 associated with a transition from a current user interface to a new user interface and a corresponding change from a current client application state to an updated client application state. As shown, a client application 802 installed on a client computing device 804 initially displays a home screen 806 on a display of the client computing device 804. The home screen 806 presents various widgets 808 to an end user. As represented in FIG. 8, end user interaction with one of the widgets 808 causes a task request message to be sent to a cloud service provider platform to which the client computing device 804 is communicatively coupled, the task request message is routed to an appropriate service or skill, and the cloud service provider platform returns a response message having a payload that causes the client application 802 to display a new graphical interface that presents information contained in the payload content. In this particular example, the widget 808 with which the end user interacted initiated a task request where the requested task is scheduling a reminder to perform a future task by the end user (e.g., checking the blood pressure of a given patient at a particular date and time). Therefore, the skill to which the task request was routed returned a response message that caused the client application 802 to display, instead of the home screen 806, an "add task reminder" screen that at least evidences the scheduling of the task reminder.

As a result of receiving the response message at the client computing device 804, the state of the client application 802 in FIG. 8 is also concurrently and correspondingly updated to a task reminder state in which functions/operations associated with scheduling of the reminder can be viewed and manipulated. Thus, the state of the client application 802 can be controlled remotely and centrally by the cloud service provider platform to which the client computing device 804 is communicatively coupled. When more than one client computing device and associated client application associated with the same end user are communicatively coupled to the cloud service provider platform, updating the application state on the client computing device from which the task request message was sent will also cause a corresponding update to the state of the client application on the other client computing device. Consequently, both client applications can be maintained in the same state by the cloud service provider platform, which can allow the end user to view the same information on either client computing device and to move seamlessly between client devices relative to completing a given task.

Referring again to FIGS. 6-7 for purposes of illustration, the payloads of the messages exchanged between the client application 602 and the cloud service provider platform 606 may be of a conversation message model (CMM) format. In some embodiments, the message payloads may more particularly be of an advanced form layout CMM format, wherein data is presented as one or more forms, and wherein each form can have multiple rows, with each row having one or more columns, and each column have one or more fields. As described above, the client application 602 understands how to generate messages in the CMM format and also understands how to translate response message payload content in CMM format into a visual representation for display on a client computing device 608.

When a new conversation (e.g., task request) is started with the cloud service provider platform 606 via a gesture-based or utterance-based interaction of the end user with the client applications 602, and a new data flow results therefrom, resulting updates to the user interface (e.g., home screen 614) on the client computing device 608 may be handled in a variety of ways. For example, a task overlay procedure may be utilized when displaying new user interfaces associated with responses to new task requests. According to the task overlay procedure, a new task panel can be launched by the client application 602 and overlayed on top of an existing task panel to present new content associated with responses to new task requests or other conversations with the cloud service provider platform 606. Thus, for example, when a new response message is received from the cloud service provider platform 606 while the end user is still interacting with payload content received with a previous response message, the current interaction may be suspended and the payload content of the new response message may be displayed in a new (e.g., overlayed) task panel. Alternatively, if the current interaction is determined to be more important/of higher priority than the payload content of the new response message, it is possible that display of the payload content of the new response message can be delayed until the current end user interaction is completed.

The task overlaying procedure may occur successively. This means that payload content associated with each of a number of subsequent task requests by the end user may be received and presented in a series of overlayed task panels that form a stack and wherein, within the stack, the home screen 614 is at the bottom and the task overlay presenting the most recently received response message payload content is at the top. Each time a new task panel is added to the stack, the flow associated with response message payload content presented in the prior top task panel can be suspended and the current flow can become the flow associated with the response message payload content presented in the new task panel. Thus, the task overlay procedure can be configured such that the flow associated with the response message payload content of the top task panel can always be the current flow and, likewise, the state of the client application may always be set to correspond to the current flow. The state of the client application may also update with each overlay of a new task panel. When the end user terminates interaction with the current flow and the top-most task panel is correspondingly closed, the immediately preceding task panel in the stack becomes the top task panel and the previously suspended flow associated with the response message payload content thereof becomes the current flow. The client application state may automatically update accordingly. This process of adding and removing task panels from a task panel stack may continue until the task panel of the home screen 614 becomes the top task panel.

In some embodiments, the cloud service provider platform 606 may send messages to the client computing device 608 in blocks (e.g., blocks of three or more messages). At least some of the messages in a block may be related, and in some cases more than one of the messages may be required to render a complete view on the client computing device 608. As the blocks traverse the pipeline of the cloud service provider platform 606, the blocks may be chunked into smaller blocks/sets of messages. Thus, a complete message block, as originally designated by the cloud service provider platform 606, may not arrive as one message block at the client application 602. It is also possible in some embodiments, that the cloud service provider platform 606 will only send one message at a time to the client computing device 608. Given that the view rendered on the client computing device 608 by the client application 602 can become unstable if the view relies on multiple messages and only some of the messages are received, the client application 602 may require that all messages related to a given view be received and parsed before the client application 602 will render the view associated with the messages. To this end, the client application 602 may "debounce" incoming messages-meaning that the client application 602 may aggregate incoming messages for some period of time or until some threshold or other condition is met. For example, the client application 602 may aggregate incoming messages until there is a lull (e.g., 100 milliseconds) between receiving new messages. All the aggregated messages may then be processed in one group, which increases the likelihood that all the messages required to render a particular view on the client computing device 608 will have been received and processed by the time the view is to be rendered.

In embodiments where, for example, the client computing device 608 receives messages from the cloud service provider platform 606 in blocks or the messages are otherwise aggregated and then processed as described above, multiple task panels of a stack of task panels already displayed on the client computing device 608 may be simultaneously replaced upon receipt of a block of messages or upon processing of an aggregated group of messages. In this regard, each block of messages or processed aggregated group of messages may have associated therewith, a screen identification parameter that identifies the view to be rendered by the payload content of the messages (e.g., "screen.id: start screen"). When the new block of messages is received at the client device or when an aggregated group of messages is processed at the client device, the screen identification parameters associated with the currently displayed task overlays can be analyzed and compared to the screen identification parameter for the new block of messages or the processed aggregated group of messages. When there is a match of screen identification parameters, the currently displayed task panels from the topmost task panel to, inclusively, the task panel having the matching screen identification parameter, can be removed, and replaced with a task panel rendered according to the payload content of the new block of messages or the processed aggregated group of messages. If no screen identification parameter match is found, then a task panel rendered according to the payload content of the new block of messages or processed aggregated group of messages can be overlayed on the current topmost task panel and the view is updated to correspond to the content of the new task panel. In cases, however, where an auto-close operation of the current topmost task panel has already been triggered, the current topmost task panel may be removed prior to overlaying the new task panel on the stack, as the triggering of the auto-close operation indicates that the skill flow corresponding to that task has already ended and there is no possibility of returning thereto.

Capabilities

A communication between a client application and a cloud service provider platform can fall into one of several categories. For example, and without limitation, a communication between a client application and a cloud service provider platform can be related to a dictation capability, an ambient recording capability, or a clinical automation capability, each of which may be implemented through communications between the client application and the cloud service provider platform. Other categories of communications related to other capabilities are also possible.

A. Dictation

In some embodiments, a task request message from a client application to a cloud service provider platform can activate a dictation service to perform a dictation operation, whereby a healthcare provider can generate electronic healthcare records using voice inputs. Creating various electronic healthcare records is a necessary task, but can also be repetitive, tedious, and time-consuming. For example, a typical physician may spend approximately two hours on electronic healthcare record-related tasks every day. The dictation service implemented according to the disclosure through cooperation of a client application with a cloud service provider platform can reduce the time required to generate electronic healthcare records, which can allow healthcare providers more time to focus on core functions.

Figure 9:
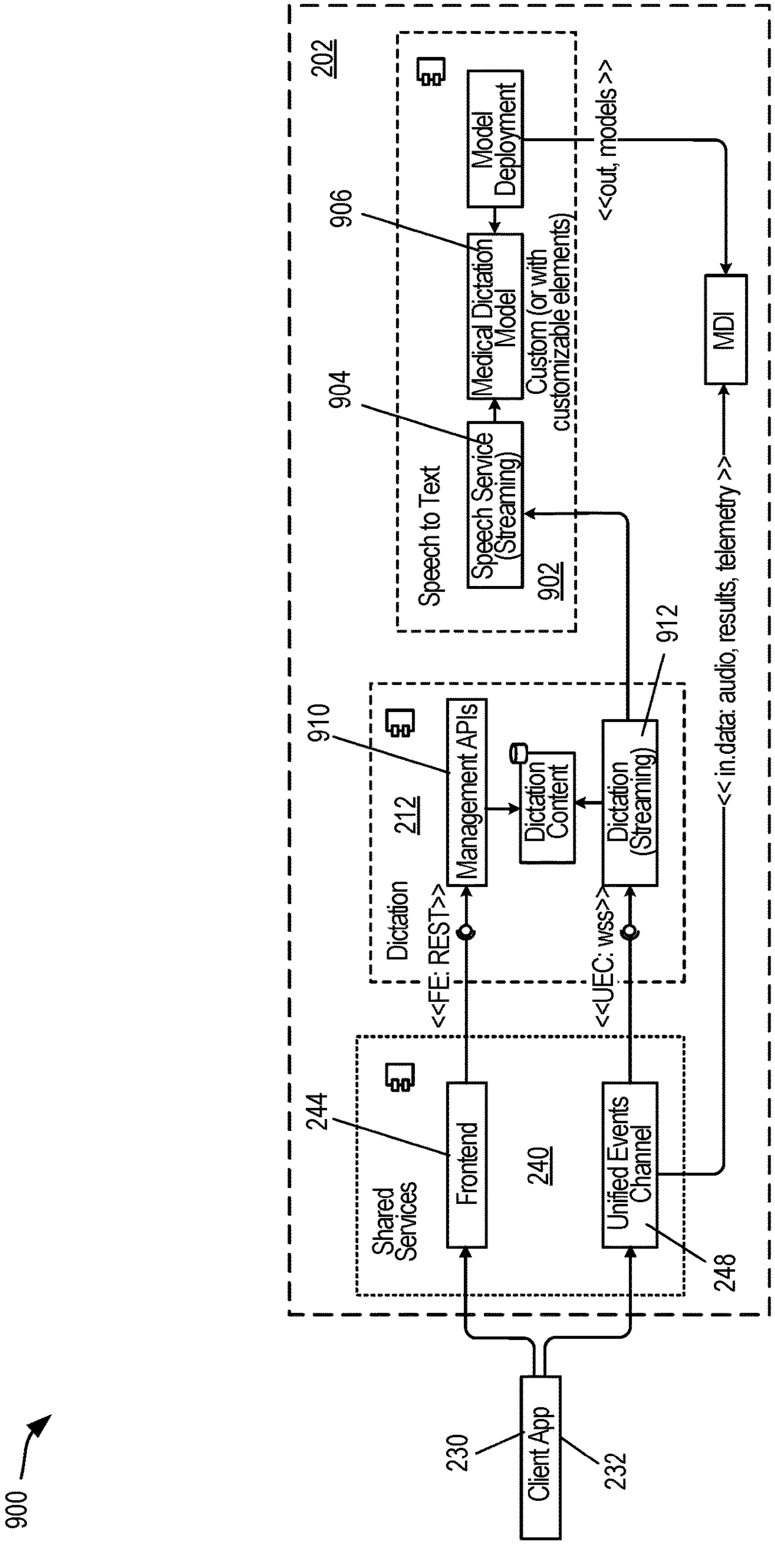
FIG. 9 illustrates a dictation service data flow in reference to the system architecture depicted in FIG. 2, according to some embodiments.

FIG. 9 illustrates one embodiment of a dictation service data flow 900, in reference to the system architecture depicted in FIG. 2. In some embodiments, the dictation service 212 may be activated from the client application 230 via messages sent across the unified event channel 248 of the frontend 244 of the cloud service provider platform 202. The dictation service 212 may be activated by, for example, engaging (e.g., selecting/clicking) an action button of the client application home screen or another widget that may be provided and displayed for the same purpose. As represented in FIG. 6, such an action button may be configured as a dictation mode initiation button. Alternatively, the dictation service may be activated by selecting/right-clicking on a "dictation" taskbar icon, or through a natural language voice command such as, for example, "Hey Oracle, activate Dictation." In still other embodiments, a unique user interface may be provided and used for activating the dictation service rather than activating the dictation service from the home screen. Once activated, the dictation service 212 can conveniently and efficiently generate healthcare records using voice inputs instead of by typing. For example, a healthcare provider can dictate information using the client application 230 and a microphone of the client device 232, and the dictation service 212 of the cloud service provider platform 202 can automatically convert the dictated information into text and enter the text into a healthcare-related document (e.g., into appropriate fields of a predefined healthcare form). In some embodiments, the dictation capability may utilize pre-seeded templates that can be filled out using dictated commands or information.

The dictation service may utilize or may be based on an artificial intelligence (AI) speech service associated with the cloud service provider platform. For example, the dictation service may utilize a speech-to-text service 902 of the cloud service provider platform 202 to transcribe dictated speech to text for insertion into electronic healthcare record documents. In some embodiments, and as shown in FIG. 9, the speech-to-text service 902 may include a streaming audio intake component 904 that receives an audio stream of the end user dictation and forwards the audio stream to a dictation model which, in this embodiment is a medical dictation model 906.

In some embodiments, the dictation service may be most conveniently activated and utilized from a mobile client application, as most if not all mobile computing devices will have a microphone. The mobile client devices are also highly portable. Nonetheless, the dictation service can also be utilized using a desktop client application installed on a desktop computing device. For example, with an end user logged in to both a mobile client application on a mobile computing device and a companion desktop client application on a desktop computing device, the end user may issue a command to switch the desktop computing device to a dictation mode. This can occur, for example, by way of an end user interaction with a widget on a user interface of the desktop client application, or alternatively, by way of a spoken command such as "Hey Oracle, pair with desktop." In either case, the mobile client application can detect the command and can, using the microphone of the mobile computing device, cause an audio stream of the speech to be sent to the cloud service provider platform. The cloud service provider platform will subsequently process the speech, and respond to the desktop client application rather than the mobile client application.

The dictation service may be implemented using a collection of components of the cloud service provider platform. For example, at a high level, the cloud service provider platform may include a dictation sub-service(s) that implements and orchestrates a dictation use case (e.g., activate, deactivate, manage workflow, send notifications, and deliver speech-to-text conversion results). In some embodiments, the audio stream conveying the dictated speech may be sent to a dictation engine (server) 908. The dictation server 908 may, for example, encompass all the components necessary to manage a complete dictation operation lifecycle and to interact with outside systems. The dictation server 908 may manage both inbound and outbound streaming within a session, may store and forward the speech audio for processing, and may send the result in a response message to the client device(s). The dictation service components may also include, for example, processing elements (workers) that receive a message from an inbound queue, process it and pushes the message to an outbound queue (if its eligible for further processing); a session manager that can manage user connection mapping, track user session status changes, update the session status, store session metadata, and notify the client application(s) of state changes; an audio stream handler that can manage incoming client connection requests, forward audio, and respond with dictation results; a dictation worker that can publish the transcription result for further post processing; a post dictation worker that can process the transcribed text and identify/enrich the transcription; a database worker that can create session metadata and may update as the session status changes; and one or more management APIs 910. Various other components may also be present, and other cloud service provider platform embodiments may have different configurations. In any case, use of the dictation service can meaningfully improve the efficiency electronic healthcare record creation, thereby unburdening healthcare providers to perform other functions that can have a greater impact on the patient healthcare experience.

B. Ambient Recording

In some embodiments, a task request message from a client application to a cloud service provider platform can cause an ambient recording service to perform an ambient recording operation whereby a spoken conversation, such as a conversation between a healthcare provider and a patient, can be recorded, transcribed to text, and used for various purposes including creating clinical notes. Creating clinical notes is an essential but time consuming process. For example, it is reported that healthcare providers typically spend approximately two to three hours per day creating clinical notes. The ambient recording service implemented according to the disclosure through cooperation of a client application with a cloud service provider platform can significantly reduce the time required to generate clinical notes.

Referring again to FIG. 7 for purposes of illustration, it can be understood that in some embodiments, the ambient recording service may be activated from the client application 602 by, for example, engaging (e.g., selecting/clicking) an action button (e.g., action button 630) of the client application home screen 614, which may be configured as an ambient recording mode activation button, or by similarly interacting with another widget that may be provided and displayed for the same purpose. Alternatively, the ambient recording service may be activated by selecting/right-clicking on an "ambient recording" taskbar icon, or through a natural language voice command such as, for example, "Hey Oracle, start the visit." In still other embodiments, a unique user interface may be provided and used for activating the ambient recording service rather than activating the dictation service from the home screen 614. Once activated, the ambient recording service can conveniently and efficiently record a spoken conversation, such as a conversation between a healthcare provider and a patient, transcribe the recorded conversation into text, and provide the text as input to a trained machine model to create a clinical note that effectively summarizes the healthcare provider-patient interaction in a standardized format. In some embodiments, the clinical note may be a Subjective, Objective, Assessment and Plan (SOAP) note.

A healthcare provider may, in some embodiments, utilize a mobile client application installed on a mobile computing device to stream a conversation to the cloud service provider platform using a microphone of the mobile computing device. The conversation may be streamed to the cloud service provider platform via a WebSocket connection (e.g., provided by the universal event channel 248 of FIG. 2) with the ambient recording service components of the cloud service provider platform. In some embodiments, the ambient recording service may utilize a generative artificial intelligence (AI) model (e.g., an ASR model) of or associated with the cloud service provider platform to analyze the transcribed text of the recorded conversation and to generate a clinical note using one or more natural language understanding and/or natural language processing techniques. Data associated with recorded conversations may, in some embodiments, be saved and used to finetune the machine learning model(s) used to analyze the transcribed text and generate the clinical notes.

It may also be possible in other embodiments to utilize a desktop client application installed on a desktop computing device to activate and interact with the ambient recording service. The process of using a desktop client application may be accomplished in a similar manner to that described above with respect to the dictation service. When a desktop client application and associated desktop computing device is used to perform an ambient recording operation, a mobile client application to which an end user (e.g., healthcare provider) is also logged in can detect an ambient recording service activation command from the end can an audio stream of the conversation to be sent to the cloud service provider platform. The cloud service provider platform will subsequently process the conversation as described above, and respond to the desktop client application rather than the mobile client application.

Once a clinical note (e.g., SOAP note) has been created, the clinical note may be sent to the client computing device and displayed thereon by the client application for healthcare provider review and possible revision. The healthcare provider can then sign the clinical note once approved. The ambient recording service can thus eliminate the need for healthcare providers to create clinical notes from scratch, thus increasing the amount of time that healthcare providers can spend with patients by reducing the amount of time required to be spent on documentation.

C. Clinical Automation

In some embodiments, a task request message from a client application to a cloud service provider platform can cause an clinical automation service to perform a clinical task. Various types of clinical tasks can be performed by the clinical automation service. For example, the clinical automation service can be utilized to request and obtain patient information such as charts, records, and images (e.g., x-rays, CT scans). The clinical automation service may also be utilized to perform tasks such as ordering patient medication (e.g., calling in prescriptions). Utilizing the clinical automation service can reduce the time required to perform clinical tasks such as those described above.

Generally speaking, the clinical automation service is implemented by a multimodal digital assistant that provides support for the various clinical functional tasks. Healthcare providers can interact with the digital assistant through, for example, user interface controls, text, and audio and voice inputs.

Figure 10:
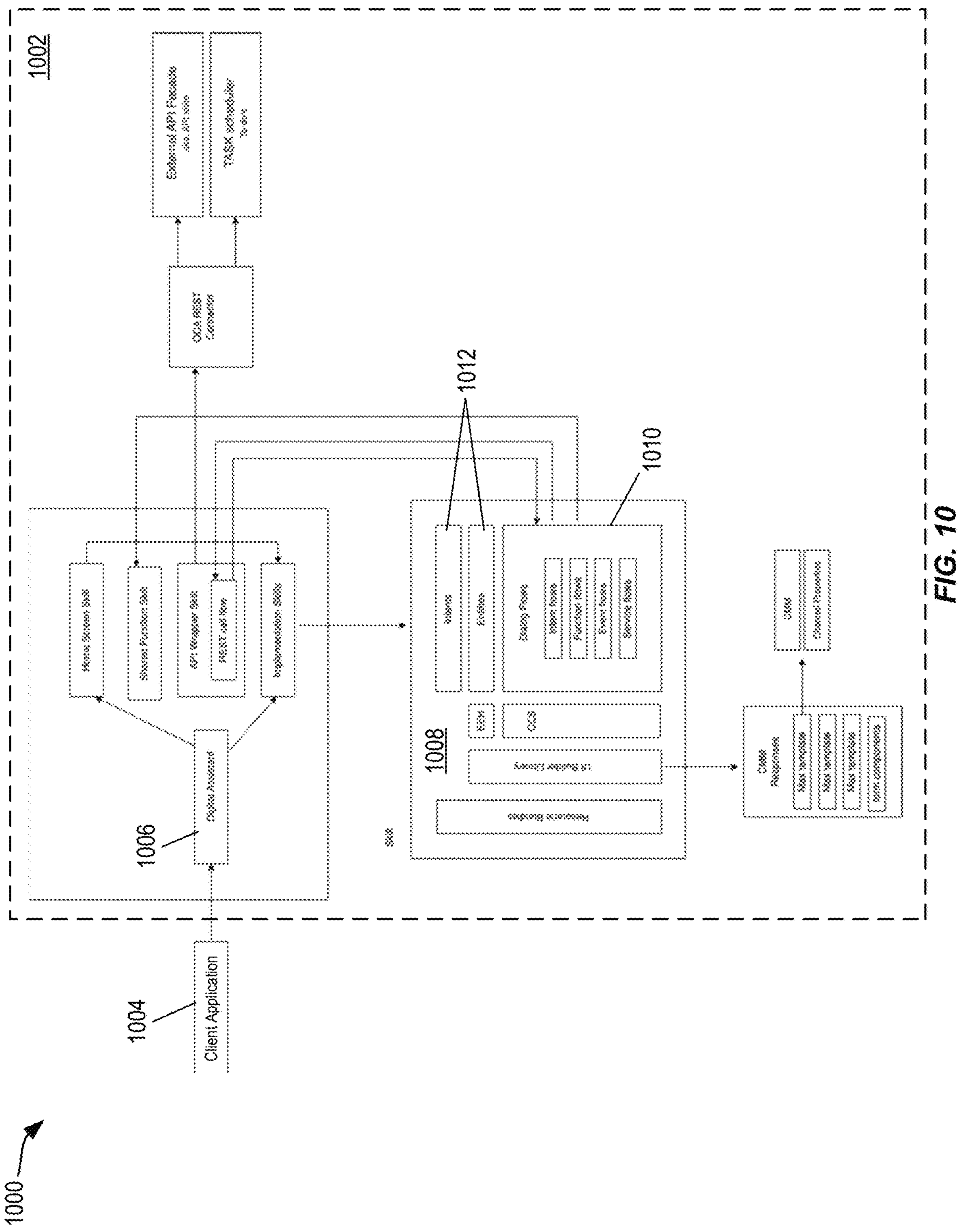
FIG. 10 illustrates a clinical automation service data flow in reference to the system architecture depicted in FIG. 2 and the dialog flows of FIGS. 6-7, according to some embodiments.

FIG. 10 illustrates one embodiment of a clinical automation service data flow 1000 implemented through a combination of a client application 1004 executing on a client computing device and communicating with a cloud service provider platform 1002, and can be best understood by further reference to FIG. 2 and to FIGS. 6-7. The clinical automation service may be activated from a client application 1004 by, for example, engaging (e.g., selecting/clicking) an action button of a client application home screen which, as illustrated in FIG. 6, may be configured as a clinical automation mode activation button. The clinical automation service may also be activated by similarly interacting with another widget that may be provided and displayed for the same purpose. Alternatively, the clinical automation service may be activated by selecting/right-clicking on a "clinical automation" taskbar icon, or via an utterance-based (natural language-based) interaction with a digital assistant 1006. In the latter case, for example, a healthcare provider may start a conversation with the digital assistant 1006 by speaking a task request such as "Please show me John Smith's chart." The request will be thereafter translated from speech to text by a speech-to-text service of or associated with the cloud service provider platform 1002 of which the clinical automation service is a part, the intent of the task request can be determined by a skill 1008 of the digital assistant 1006, and a service or skill of the cloud service provider platform can retrieve the requested chart from a database and present the chart to the healthcare provider on the client computing device. In still other embodiments, a unique user interface may be provided and used for activating the clinical automation service rather than activating the clinical automation service from a home screen of the client application 1004.

In some embodiments, a healthcare provider can engage with the clinical automation service using a mobile client application installed on a mobile computing device and/or using a desktop client application installed on a desktop computing device, in the same or a similar manner as that described above relative to the dictation service and the ambient recording service.

As is the case with other task requests and corresponding tasks, the data flow associated with use of the clinical automation service involves an exchange of messages between the client application 1004 (e.g., mobile client application) the cloud service provider platform 1002. More particularly, task request messages sent from the client application 1004 relative to tasks to be performed by the clinical automation service are sent to the digital assistant 1006 (also see FIG. 2 in this regard) of the cloud service provider platform 1002. Based at least in part on the context of the message, the digital assistant 1006 can then route the task associated with the task request message to a selected (most appropriate) skill of a plurality of skills 1010 associated with the digital assistant 1006, where the task can be performed by processing steps of the task according to the task flow of the skill. In some cases, the selected skill may not be able to complete the entirety of the task, and may pass the task to another skill to complete the task.

The selected skill may be chosen, for example, by utilizing components 1012 that may apply natural language processing, natural language understanding, named entity recognition, and/or other artificial intelligence technologies to analyze the natural language utterance provided in a payload of a task request message and to thereby determine the intent of the request (i.e., to identify the task). The response generated by the selected skill and sent back to the client device 1004 includes a payload having a content that is responsive to the requested task. For example, the payload may include a natural language response to a query (e.g., a request for information), which may initiate further conversation between the healthcare provider and the digital assistant 1006. The payload content may also include requested information—e.g., John Smith's chart relative to the example task request described above. In either case, receipt of the response message by the client device on which the client application 1004 is installed will cause the client application 1004 to display the payload content on a display of the client computing device and will update the state of the client application 1004 accordingly.

The view presented can be defined by configuration parameters in the response message. In some embodiments, the view may be a task panel overlay, as previously described. In some embodiments, where a task panel is displayed upon receipt of the response message as an overlay or otherwise, the task panel may include, for example a shared context area that can provide various types of contextual information to the healthcare provider end user, including information about a patient (e.g., patient name) or information about the healthcare provider. The task panel may also include a dialog area where the actual response message (e.g., text) or a prompt can be displayed. When a prompt is displayed, the prompt may be accompanied by an audio (verbal) response that is spoken to the healthcare provider. The task panel may also display a modal area where rich user interface content such as forms, tables, cards, or similar layouts may be displayed. The model area may display, for example, the details of a given task (e.g., in case of a medication order, information about the medication being ordered, ordering options, etc.). In any case, use of the clinical automation service can simplify and render more efficient a number of clinical tasks that are commonly performed by healthcare providers, which again can provide healthcare providers with more time to interact with patients or perform other non-administrative more directly related to patient care.

Paired Application Control

An end user (e.g., health care provider) facility may be equipped with both mobile computing devices and desktop computing devices via which the health care provider can interact with a cloud service provider platform configured to assist the health care provider in performing various clinical functions. A mobile client application may be installed on each mobile computing device and a desktop client application may be installed on each desktop computing. The mobile computing devices and the desktop computing devices may have different capabilities. For example, the mobile computing devices may have microphones, while the desktop computing devices may have no microphones or may have microphones of lower quality. On the other hand, the desktop computing devices may be equipped with displays that are larger and of higher resolution than the displays of the mobile computing devices, and/or may be equipped with speakers that are of higher quality than the built-in speakers of the mobile computing devices. Thus, it may be preferred to use a mobile computing device and its associated mobile client application for some tasks, and a desktop computing device and its associated desktop client application for other tasks.

Additionally, in at least some cases, performance of a clinical task may be rendered more efficient or otherwise may be better performed if the health care provider can begin the task on one of a mobile computing device or a desktop computing device and complete the task on the other of the mobile computing device and the desktop computing device. For example, it may be easier for a health care provider to use a mobile computing device and a voice command to request retrieval of a patient x-ray by the cloud service provider platform, but it may be preferred to view the x-ray on the larger and higher resolution display of a desktop computing device. Consequently, it is desirable that a health care provider or another end user of a clinical assistance cloud service provider platform can seamlessly transition one or more times between a mobile computing device and a desktop computing device when utilizing the cloud service provider platform to perform a given clinical task.

Accordingly, a mobile client application and a desktop client application that are concurrently associated with a same user session with the cloud service provider platform, can be paired with one another so that the mobile client application and the desktop client application can operate in concert, under the control of the cloud service provider platform, to provide an end user with a single seamless experience when the end user switches between client devices while performing a task. Likewise, with the mobile client application and the desktop client application paired, an end user can still perform a task when one of the client devices is unavailable or when, for example, one of the client devices (e.g., the desktop computing device) is not conveniently accessible based on the end user's current location.

In some embodiments, the mobile computing device and the mobile client application installed thereon may be considered to be the primary client device/client application, and the desktop computing device/desktop client application may be considered to be the secondary client device/client application. For example, the desktop client application may, in some embodiments, be considered to be a companion application to the mobile client application and the capabilities of the desktop client application and the desktop computing device can be used to support use of the mobile client application and the mobile computing device.

Figure 11:
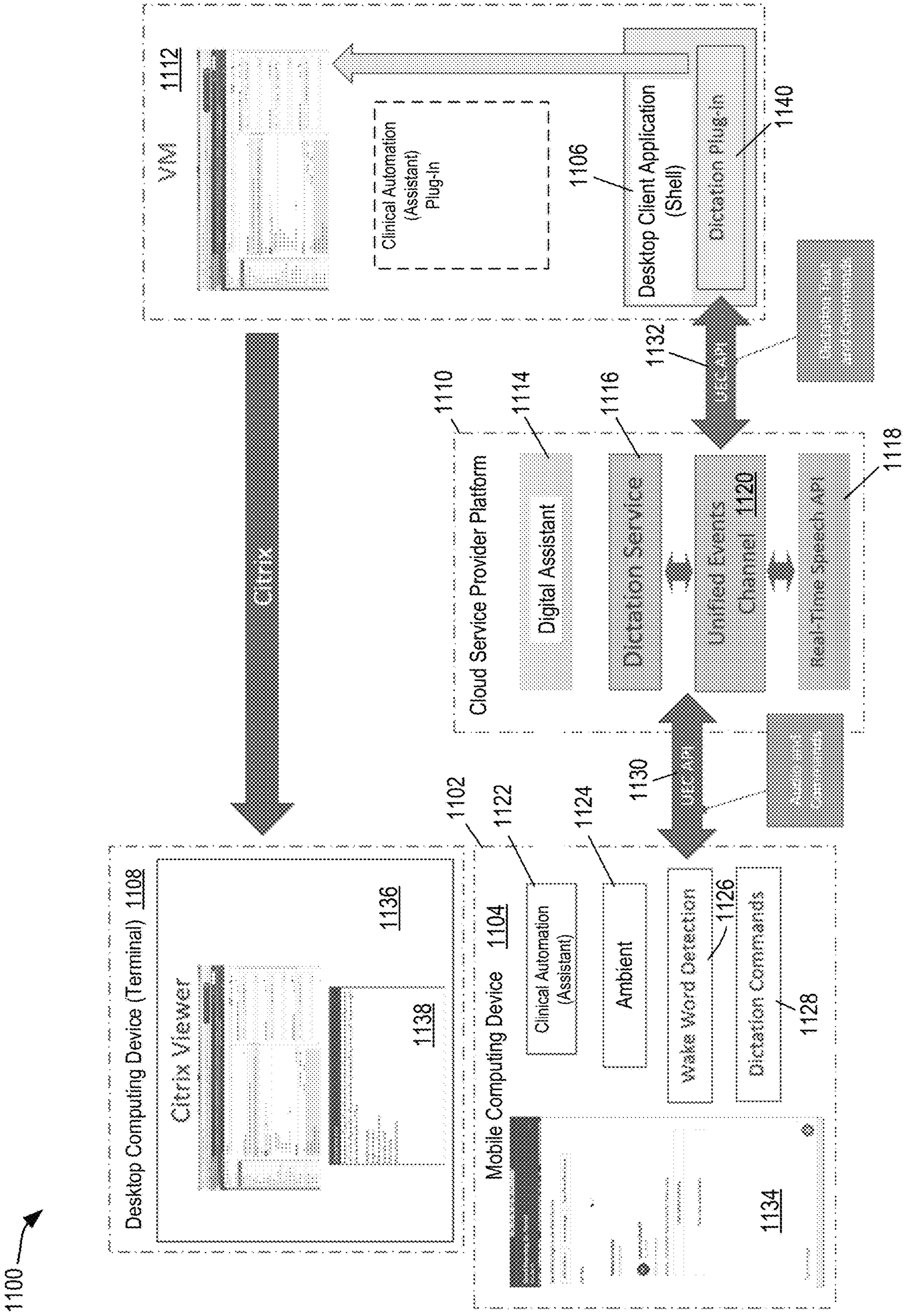
FIG. 11 illustrates a paired client application control scheme, according to some embodiments.

A better understanding of a paired client application control scheme 1100 for use in a system for facilitating healthcare provider tasks, such as the a system 200, can be gained by reference to FIG. 11 and to FIG. 2, and to the additional description provided below. As shown in FIG. 11, a mobile client application 1102 executing on a mobile computing device 1104 and a desktop client application 1106 executing on a desktop computing device 1108 may be communicatively coupled to a cloud service provider platform 1110 of a system for facilitating healthcare provider tasks. In this particular embodiment, the desktop client application 1106 is deployed as a desktop client application shell on a virtual machine, such as a Citrix virtual machine 1112, and the desktop computing device 1108 is a virtual desktop that includes a terminal via which an end user can interact with the desktop client application 1106 and the cloud service provider platform 1110. Other embodiments may utilize other desktop computing device configurations, such as a traditional desktop computing device having its own local operating system and a network connection to the cloud service provider platform 1110. It may also be possible in some embodiments, that a desktop client application may be a configured as a regular web application instead utilizing Citrix. For example, a web form of the desktop client application could run on Linux-based clients.

As is further represented in FIG. 11, the cloud service provider platform 1110 can include a digital assistant 1114. While not shown, the cloud service provider platform 1110 may also include or have associated therewith a plurality of different skills that include the logic required to process specific tasks, as previously described with respect to the skills 208 of the cloud service provider platform 202 of FIG. 2. The cloud service provider platform 1110 can also include a plurality of capabilities which, in this particular embodiment, include a dictation service (engine) 1116, which may operate to, for example, transcribe spoken information into textual patient notes, and a real-time speech API 1118 that is configured to receive audio streams from the mobile computing device 1104 or the desktop computing device 1108 and to facilitate transcription of the audio into text and return of the text to the mobile computing device 1104 or the desktop computing device 1108 for display to the end user.

It may also be understood from FIG. 11 that the cloud service provider platform 1110 also includes a unified event channel 1120 which, like in the system 200 of FIG. 2, can be a cloud service of the cloud service provider platform 1110 and facilitates a bidirectional transfer of messages between the digital assistant 1114 and the services 1116, 1118 of the cloud service provider platform 1110 and the mobile and desktop computing devices 1102, 1108 and their associated client applications 1102, 1106. The unified events channel 1110 can provide a WebSocket interface by which audio, conversational text, and event traffic can flow to and from the client applications 1102, 1106. For example, audio and conversation text received from the client applications 1102, 1106 can be routed by the unified events channel 1120 to the dictation service 1116, the real-time speech API 1118, or a skill of the digital assistant 1114. A mobile computing device unified event channel API 1130 may be deployed and utilized to facilitate communications between the mobile client application 1102 and the unified event channel 1120 of the cloud service provider platform 1110. For example, the mobile computing device unified event channel API 1130 may be called when sending audio or spoken (e.g., dictation) commands from the mobile computing device 1104 to the cloud service provider platform 1110. Likewise, a desktop computing device unified event channel API 1132 may be deployed and utilized to facilitate communications between the desktop client application 1106 and the unified event channel 1120 of the cloud service provider platform 1110. For example, the desktop computing device unified event channel API 1132 may be called when sending transcribed dictation text to the desktop computing device 1108 or spoken commands from the desktop computing device 1108 to the cloud service provider platform 1110.

As illustrated in FIG. 11, a home screen skill or a similar function of the cloud service provider platform 1110 has caused the mobile client application 1102 to display on the mobile computing device 1104, a user interface 1134 that includes widgets or other selectable interface objects by which an end user can activate various capabilities, services, or skills of the cloud service provider platform 1110. In this example, the user interface 1134 displayed on the mobile computing device 1104 is shown to include a clinical automation (also referred to as assistant) widget 1122 and an ambient recording widget 1124 A wake word module 1126 and a dictation component 1128 are also associated with the mobile computing device 1104. The clinical automation (assistant) widget 1122 can be used to start a conversation with the digital assistant 1114 by which the digital assistant 1114 can be requested to assist an end user with, for example, a clinical automation task (e.g., retrieving a patient chart). While the presence of the clinical automation (assistant) widget 1122 on the user interface of the mobile computing device 1104 indicates use of the mobile computing device 1104 for conversing with the digital assistant 1114, it is also represented in FIG. 11 that the desktop computing device 1108 may instead be used for that purpose in other embodiments. The ambient recording widget 1124 can be used to activate an ambient recording service of the cloud service provider platform 1110, whereby a spoken conversation, such as a conversation between a health care provider and a patient, can be recorded and subsequently transcribed into text for use in generating notes or for other tasks. The ambient recording service is described more thoroughly above relative to the client applications. The wake word component 1126 can enable an end user to make voice inputs to the mobile client application 1104 that can after speaking a wake word (e.g., "Hey, Oracle"), which is picked up by a microphone of the mobile computing device 1104. For example, the wake word may be spoken prior to engaging the digital assistant 1114 or the dictation service 1116 of the cloud service provider platform 1110 via a voice command. The dictation component 1128 may recognize various dictation commands input to the mobile client application 1102 and can facilitate end user utilization of the dictation service of the cloud service provider platform 1110.

Pairing the mobile client application 1102 and the desktop client application 1106 may involve registering each client application with the unified event channel 1120 of the cloud service provider platform 1110. When an end user initially logs in to the cloud service provider platform 1110 using a computing device in some embodiments, the unified event channel 1120 may receive a registration request from the client application executing on the computing device. Thus, when an end user initially signs in to the cloud service provider platform 1110 using the mobile client application 1102 on the mobile computing device 1104, the unified event channel 1120 may receive a registration request from the mobile client application 1102. The registration request message may include information that identifies the mobile computing device 1104 and capabilities of the mobile computing device 1104 to the cloud service provider platform 1110. For example, the mobile client application 1102 may inform the unified event channel 1120 that it is installed on a "mobile" device that includes a high-quality microphone. Likewise, when an end user initially signs in to the cloud service provider platform 1110 using the desktop client application 1106 of the desktop computing device 1108, the unified event channel 1120 can receive a registration request from the desktop client application 1106. The registration request message may include information that identifies the desktop computing device 1108 and capabilities of the desktop computing device 1108 to the cloud service provider platform 1110. For example, the desktop client application 1106 may inform the unified event channel 1120 that it is installed on a "desktop" device that includes a display capable of displaying large images. The client device identifications and capabilities may be saved upon registering the mobile computing device 1104 and the desktop computing device 1108 with the cloud service provider platform 1110.

In some embodiments, the unified event channel 1120 may, relative to the mobile client application 1102 and the desktop client application 1106, provide a capability that is akin to an enhanced "chat room." Each client computing device that is assigned to a "chat room" and each client computing device in the same room can see the messages associated with the other client computing devices. Each client computing device may also stream audio to the room and receive audio streams from other client computing devices. The unified event channel 1120 can also allow each client computing device in a room to see what other computing devices are in the room (i.e., registered with the cloud service provider platform 1110) and their capabilities. Unlike combined application behavior, which is typically determined by the combination of front-end and back-end system components, the behavior of an intelligent paired application control scheme as described herein is determined by the combination of front-end systems and the capabilities of the client computing devices registered with the unified event channel 1120.

A mobile client application and a desktop client application can be paired in different ways. For example, the mobile client application 1102 and the desktop client application 1106 can be paired according to a "single sign on" application pairing procedure where the end user first signs in to the desktop client application 1106 on the desktop computing device 1108 and then pairs the mobile client application 1102 with the desktop client application 1106. For example, once the end user has signed in to the desktop client application 1106, the end user may, in some embodiments, be able to subsequently pair the mobile client application 1102 with the desktop client application 1106 by using a camera of the mobile computing device 1104 to read a bar code, a QR code, or another action initiating object displayed on a display of the desktop computing device 1108. Alternatively, a temporary alphabetic, alphanumeric, or numeric code may be obtained from the desktop computing device 1108 and entered into the mobile client application 1102.

Alternatively, the mobile client application 1102 and the desktop client application 1106 can be paired according to a "separate sign on" application pairing procedure where the user independently enters sign-in information into the desktop client application 1106 and the mobile client application 1102. The registration requests received by the unified event channel 1120 during each of the separate sign-ins serves to pair the mobile client application 1102 with the desktop client application 1106.

Upon registration of the mobile client application 1102 with the cloud service provider platform 1110, the mobile client application 1102 may immediately or soon thereafter request from the unified event channel 1120 and identification of other client devices that are registered with the cloud service provider platform 1110. Likewise, upon registration of the desktop client application 1106 with the cloud service provider platform 1110, the desktop client application 1106 may immediately or soon thereafter request from the unified event channel 1120 and identification of other client devices that are registered with the cloud service provider platform 1110. When a mobile computing device is identified as being registered with the cloud service provider platform 1110, a mobile microphone option may appear on a user interface of the desktop client application 1106 and selecting the mobile microphone option can allow the desktop computing device 1108 to record audio using the microphone of the mobile computing device 1104.

In some embodiments, neither concurrent user sessions with multiple mobile computing devices nor concurrent user sessions with multiple desktop computing devices are permitted. In such an embodiment, a sign in to a second mobile computing device while already signed in with the mobile computing device 1104 may terminate the previous user mobile computing device session or a sign in to a second desktop computing device while already signed in with the desktop computing device 1108 may terminate the previous desktop computing device user session.

During use of the mobile computing device 1104 and the desktop computing device 1108 to receive assistance from the services or skills of the cloud service provider platform 1110 with clinical tasks, the unified event channel 1120 receives tasks request messages from the mobile computing device 1104 and/or the desktop computing device 1108. For example, the unified event channel 1120 may receive from the mobile computing device 1104 in response to an end user interaction with the mobile client application 1102, a task request message corresponding to a related task to be performed by the cloud service provider platform 1110. The task request message may also identify a state of the mobile client application 1102. Upon receiving the state of the mobile client application 1102, the cloud service provider platform 1110 can synchronize a state of the desktop client application 1106 with the state of the mobile client application 1102. The cloud service provider platform 1110 can then determine a context associated with the task request message and based at least in part on the context, can route the task request message to a selected task flow of a plurality of task flows associated with the various services or skills of the cloud service provider platform 1110. As a result, the unified event channel 1120 can receive a response message from the cloud service provider platform 1110 that was generated in response to the task being executed by processing steps of the task. The response message can have a payload content that includes a set of configuration parameters that define a layout of the payload content when displayed on the user interface 1134 of the mobile computing device 1104. The response message is then provided to both the mobile computing device 1104 and the desktop computing device 1108, whereafter the payload content of the response message is displayed on a display of one or both of the mobile computing device 1104 and the desktop computing device 1108 according to the configuration parameters and the capabilities of the mobile computing device 1104 and the desktop computing device 1108. In other example data flows, the task request message may be received from the desktop computing device 1108 instead of the mobile computing device 1104. The task request message received by the unified event channel 1120 may result from an end user interaction with a widget or another interface object displayed on the mobile computing device 1104 or the desktop computing device 1108, or by the end user issuing a spoken command.

A number of different end user-system sequence flows may be associated with engaging the various services and skills offered by the cloud service provider platform 1110 using the mobile computing device 1104 or the desktop computing device 1108. For example, when the mobile client application 1102 is in a standby mode (rather than having a muted microphone, or being in an active audio mode), an end user may utter a wake word (e.g., "Hey, Oracle") followed by a query to activate and enter the clinical automation (assistant) mode of operation and send the query to the digital assistant 1114. In such a scenario, the mobile client application 1102 can run the audio feed associated with the utterance through the wake word component 1126, and the wake word component 1126 can recognize the wake word, notify the mobile client application 1102, and specify an audio offset immediately following receipt of the wake word. The mobile computing device 1104 can then begin streaming audio to the unified event channel 1120, starting at the specified offset. The audio stream can be directed by the unified event channel 1120 to the real-time speech API 1118 of the cloud service provider platform 1110. At the same time, the mobile client application 1102 can send a message to all related client devices registered with the cloud service provider platform 1110 (i.e., all client devices in the same virtual "room") informing the client devices that a client automation (assistant) operation has begun. The desktop client application 1106 of the desktop computing device 1108 receives this message and, at a minimum, may resultantly update a related status icon of the current desktop client application 1106 user interface 1136. With the audio stream being delivered to the real-time speech API 1118, the real-time speech service of the cloud service provider platform 1110 can begin returning partial transcripts to the mobile computing device 1104 and the desktop computing device 1108 via the unified event channel 1120. In some embodiments, the mobile client application 1102 may display partial transcripts for end user feedback, such as in a text box of the user interface 1134. The desktop client application 1106 may, in some embodiments, ignore all partial transcripts received by the desktop computing device 1108, or may display partial transcripts, such as in a bubble notification or a command box 1138. The real-time speech service eventually returns a final transcript addressed to both the mobile computing device 1104 and the desktop computing device 1108. In some embodiments, the mobile client application 1102 may display the final transcript in a text box. The final text of the final transcript is also forwarded to the digital assistant 1114. This process can repeat until the end user conversation with the digital assistant 1114 is terminated.

Another sequence flow can result from an end user activating and entering the clinical automation (assistant) mode of operation from the desktop computing device 1108. For example, the end user may click on a clinical automation (assistant) widget (not shown in FIG. 11), which may be present on the user interface 1136 of the desktop computing device 1108 when the desktop client application 1106 can be used to converse with the digital assistant 1114, and thereafter begins speaking. In this case, the desktop client application 1106 becomes aware that the clinical automation (assistant) service has been activated and may update the aforementioned status icon on the desktop computing device 1108 user interface 1136. The desktop client application 1106 also sends a message to all related client devices registered with the cloud service provider platform 1110 (i.e., all client devices in the same virtual "room") informing the client devices that a client automation (assistant) operation has begun. The mobile client application 1102 thus receives the message and begins streaming audio to the unified event channel 1120, which directs the audio stream to the real-time speech service of the cloud service provider platform 1110 via the real-time speech API 1118. The remaining sequence flow is the same as described above relative to activation of the clinical automation (assistant) mode from the mobile computing device 1104.

Another sequence flow can result from an end user activating and entering the dictation mode of operation from the desktop computing device 1108. For example, the end user may engage with a user interface widget or may type a hotkey combination to start dictation, and then begin to speak. In this case, the desktop client application 1106 is aware of the widget interaction or the of the hotkey event and send a message to all related client devices registered with the cloud service provider platform 1110 (i.e., all client devices in the same virtual "room") informing the client devices that a dictation operation has begun. The desktop client application 1106 can also activate a dictation plugin 1140, which may in some embodiments, perform at least some dictation preparation work. The mobile client application 1102 receives the message sent by the desktop client application 1106 and can begin streaming the audio associated with the speech of the end user to the unified event channel 1120, which can direct the audio stream to the dictation service 1116 of the cloud service provider platform 1110. The mobile client application 1102 may also update the user interface 1134 of the mobile computing device 1104 to reflect activation of the dictation mode. The dictation service can begin to return various responses, which are addressed to both the mobile computing device 1104 and the desktop computing device 1108. In this example, the mobile client application 1102 may ignore the responses (message type), while the desktop client application 1106 may pass all such messages to the dictation plugin 1140 to be acted upon. This sequence flow can continue until the dictation operation is terminated.

Another sequence flow can result from an end user activating and entering the dictation mode of operation from the mobile computing device 1104. For example, the end user may click on a dictation widget (e.g., action button) on the user interface 1134 of the mobile computing device 1104. In this case, it is mobile client application 1102 that sends the message to the registered client devices to inform the client devices that a dictation operation has begun prior to beginning streaming the audio of the end user's speech. The desktop client application 1106 receives the message sent by the mobile client application 1102, and may update its user interface accordingly. The desktop client application 1106 may also activate the dictation plugin 1140. Dictation service responses may then begin to be returned and may acted upon as described above relative to activating the dictation service from the desktop computing device 1108, until the dictation operation is terminated. Another sequence flow can result from an end user using the mobile computing device 1104 to activate and enter the dictation mode of operation via the clinical automation (assistant) mode. For example, the end user may utter a dictation activation phrase that includes a wake word (e.g., "Hey Oracle, start dictation") while in standby mode, or just an dictation activation phrase (e.g., "start dictation") when already in the clinical automation (assistant) mode. In this case, the clinical automation (assistant) functionality of the mobile client application 1102 detects the command and proceeds as described in the example sequence flow described immediately above, starting with the second step.

In the above sequence flow examples, the participating client computing devices (e.g., the mobile computing device 1104 and the desktop computing device 110) handle the events in the virtual "room" in a manner that is appropriate to their client application states and device capabilities. For example, when dictation is initiated, whether on the mobile computing device 1104 or on the desktop computing device 1108, the desktop client application 1106 may react to the dictation start event by displaying a the "dictation box" user interface component 1138 for collecting dictated text. If a dictation operation starts when the desktop computing device 1108 is not present, the mobile client application 1102 may display such a dictation box user interface object instead. In any case, many other sequence flows and associated user interface views are possible in other embodiments. For example, with respect to audio capture and wake word detection, the mobile client application 1102 can include additional widgets (e.g., action buttons) for controlling actions such as, without limitation, starting and stopping dictation, navigating form fields, pasting dictation box contents while in dictation mode, starting the clinical automation (assistant) mode by clicking a button rather than uttering a wake word; and muting the microphone. Additionally, some embodiments of the mobile client application 1102 can include a mobile dictation box, regardless of whether the desktop computing device 1108 is present, to facilitate continued dictation while an end user walks or otherwise moves from one location to another, or at least while being away from the desktop computing device 1108. In such an example, dictated text may be accumulated in the mobile dictation box and synchronized between the mobile client application 1102 and the desktop client application 1106. As the end user gets closer to the desktop computing device 1108 or arrives at another location and signs in to a different desktop computing device, the accumulated dictated text can be transferred to (pasted) into a document, etc., such as a document of an electronic health record system.

In terms of distribution of functionality between the mobile client application 1102 and the desktop client application 1106, there are a number of possible options. For example, much of the functionality can be distributed (made available) through one of the mobile client application 1102 or the desktop client application 1106, or it can be duplicated (made available) through both the mobile client application 1102 and the desktop client application 1106. The paired mobile client application 1102 and desktop client application 1106 may have different hierarchies in different embodiments. For example, in a minimal functionality configuration of the mobile client application 1102, the mobile client application 1102 may only effectuate audio capture and wake word detection. Beyond these functions, there may be no mobile client application run-time user experience at all once the two app instances are paired up. In such a minimal functionality configuration, the mobile computing device 1104 can function as a regular networked microphone (without custom buttons). To start, stop and control a dictation operation, for example, an end user may have to engage widgets on the desktop computing device user interface 1136, use keyboard shortcuts, or use voice commands.

In another example, the desktop client application 1106 may have a minimal functionality configuration. In such a configuration, the desktop client application 1106, when paired, may only delegate audio capture and wake word detection to the mobile client application 1102. All other functionality may remain available on the desktop computing device 1108 regardless of whether it is paired. The mobile client application 1102 may also provide duplicate functionality. For example, an end user can choose to start dictation by engaging a widget on the mobile client device user interface 1134 or by engaging a widget of a desktop client application 1106 toolbar (or full-size window, etc.). Additionally, if dictation and clinical automation (assistant) top-level commands are provided on the mobile client application 1102, a desktop toolbar mode (when paired) can be disabled or reduced to a read-only status display in some embodiments. In some embodiments of such a configuration, a full-size clinical automation (assistant) view provided by the mobile client application 1106 may be reduced or disabled when the client applications are paired since the clinical automation (assistant) is already implemented by the mobile client application 1102.

The paired mobile client application 1102 and desktop client application 1106 can also handle output data in different ways. As an example, consider a case where an end user issues a voice command to open an x-ray image. The captured audio associated with the voice command is sent to the digital assistant 1114 via the unified event channel 1120, where the voice command is analyzed and the intent of the voice command is determined to be a request to open the x-ray image. The command is then published back to the unified event channel 1120 (virtual room) and the desktop client application 1106, if the present, can pick up the command and the desktop computing device 1108 can be used to display the desired x-ray image, as the display of the desktop computing device 1108 is preferred for this purpose based on the display capability identified in the related earlier desktop computing device 1108 registration request message. If the desktop client application 1106 is not present, then the mobile client application 1102 can pick up the command and open the x-ray, such as by using an embedded viewer.

According to various embodiments, a root session may be maintained and may act as a parent session for each user login from various client applications. When an end user logs in to a mobile client application or a desktop client application, a session manager can determine if a root session exists. If no root session exists, the session manager can create a root session, followed by session for the current client application login. Every login for the same user will then be a child of root session. When a service needs to share state across multiple logins (desktop or mobile) for an end user, the root session can be used for saving the state.

It can be understood from the foregoing disclosure, that pairing a mobile client application and a desktop client application and controlling both applications from a cloud service provider platform can provide several unique and valuable functions. For example, when the client applications are paired as described herein, an end user working on a desktop computing device can use the mobile client application to stream audio (e.g., voice) using a microphone of the mobile computing device, and the associated cloud service provider platform will route processed results (e.g., a transcript) of the audio stream to the desktop client application. Additionally, an end user can input voice commands to the mobile client application to navigate the desktop client application. The user state can be carried across both the mobile client application and the desktop client application. For example, an end user can sign in to both the mobile client application and the desktop client application and share the same state across logged-in applications running on different platforms with various capabilities.

Task Scheduling and Notifications

Healthcare providers commonly see numerous patients each day. The cumulative number of core and administrative tasks that may need to be performed relative to the patients treated by a healthcare provider may be significant. Some of these tasks may be tasks that are performed in during a patient visit, while others may not. Rather, some tasks may need to be performed prior to a patient visit and other tasks may need to be performed at some point after a patient visit. For example, in addition to scheduling a patient visit, a healthcare provider may need to obtain a patient record, an x-ray or another patient image, or other patient-related information prior to the patient visit. During the patient visit, the healthcare provider may wish to, for example, check the patient's blood pressure, collect blood for lab work, and/or conduct other tests or have certain discussions with the patient. After the patient visit, the healthcare provider may need to order the lab work, call in a prescription, or order other testing for the patient. Healthcare providers may benefit from the ability to easily and accurately generate calendar events for such events and tasks and to associate therewith future reminders (notifications) that can be provided to the healthcare providers at or around a time at which an event is set to occur or a task is to be performed. System embodiments according to the disclosure can provide a digital assistant for efficiently scheduling healthcare-related events and tasks and related techniques for generating and sending timely notifications for the scheduled events and tasks. In some embodiments of the cloud service provider platforms described herein, the digital assistant thereof may be associated with a task manager and notification service component (e.g., task manager and notification service component 218 of FIG. 2) that can cooperate with the digital assistant to schedule events and tasks for healthcare providers and to timely generate and send notifications.

Figure 12:
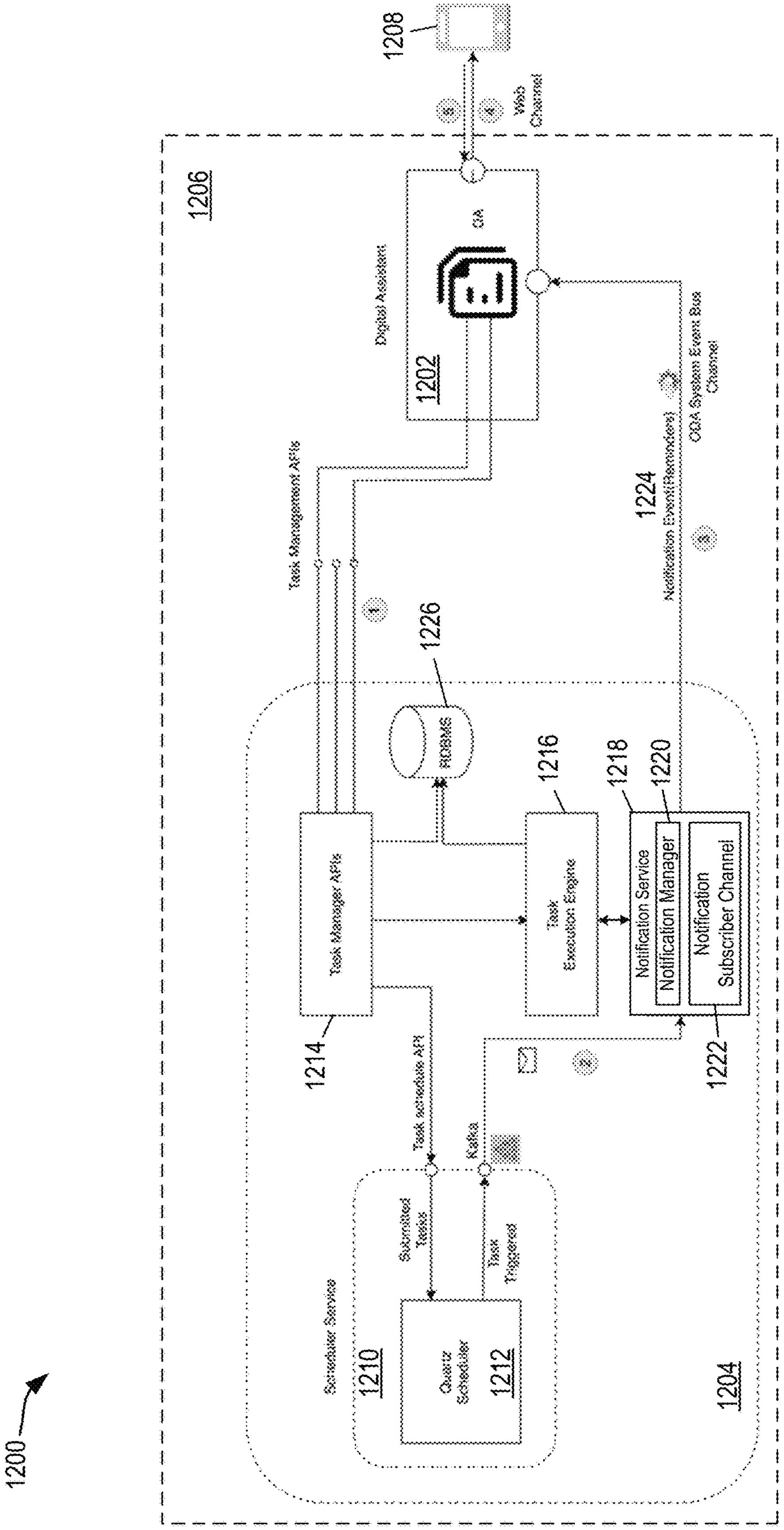
FIG. 12 illustrates a data flow diagram associated with the scheduling of tasks and the generating of notifications by a cloud service provider platform, according to some embodiments.

A better understanding of various mechanisms by which a digital assistant of a cloud service provider platform can perform scheduling and notification functions may be obtained by reference to, for example, the architectural diagram of FIG. 2 and the data flow 1200 of FIG. 12. As previously described, FIG. 2 illustrates a task manager and notification service component 218 of a cloud service provider platform 202 that is communicatively coupled to a digital assistant 206 of the cloud service provider platform 202 for performing such functions. To better illustrate the data flows between such components in the course of scheduling events and tasks and generating and sending notifications therefor, a similar arrangement of components is depicted in FIG. 12.

The data flow 1200 illustrated by the data flow diagram of FIG. 12 is shown to involve a digital assistant 1202 and a task manager and notification service layer 1204 of a cloud service provider platform 1206. The digital assistant 1202 may include, or be associated with, one or more machine-learning models, such as large language models (LLMs) for interpreting natural language end user inputs, scheduling events and tasks, and generating notifications. An end user may converse with the digital assistant using a client application of a client computing device 1208, as described above. In this example, the client computing device 1208 is a mobile computing device and the client application is a mobile client application, but conversations with the digital assistant 1202 may also occur via a desktop computing device and an associated desktop client application in other examples.

In the example of FIG. 12, the task manager and notification service layer 1204 is shown to include a scheduler service 1210 having a scheduler component 1212, a plurality of task manager APIs 1214, a task execution engine 1216, and a notification service 1218. The scheduler service 1210 can allow end users to schedule, unschedule, or repeat tasks (i.e., to generate task entries) at a specified time (e.g., due date, completion of an operation, etc.). The scheduler service 1210 can also operate to start, stop or pause the scheduler component 1212. The task manager APIs 1214 can be called to manage tasks such as the creation, update, and deletion of events and tasks. The task manager APIs 1214 can also allow each service of the cloud service provider platform 1206 that receives notification messages to configure a channel by which to receive the notification messages. The task execution engine 1216 may be responsible for scheduling events and tasks, and routing the result of execution thereof to appropriate components. The notification service 1218 may comprise several components, including for example, a notification manager 1220, and notification subscriber channel 1222. The notification manger 1220 can manage the generation of notification messages 1224 when a criteria for performing a task is triggered. The notification subscriber channel 1222 can direct the notification messages 1224 to the appropriate subscribed services.

In one embodiment, an end user can generate a task entry for a future task, note, etc., through a conversation with the digital assistant 1202. For example, the end user may establish a conversation with the digital assistant 1202 by selecting a clinical automation (assistant) mode widget on the client application of the client computing device 1208 or by uttering a wake word (or a wake word along by a command) as described above with respect to FIG. 11. For example, the end user may say "Hey Oracle, please remind me that patient Jane Doe has a check-up at 4 PM next Thursday." In response, the digital assistant 1202 can, for example, provide a confirmation, request more information, and/or change subjects. Once the conversation is established, the end user may provide further utterances (e.g., commands) to the digital assistant 1202, which are transmitted thereto as messages. In some embodiments, the end user may expressly request the scheduling of a task by the digital assistant 1202 and, in that regard, the end user may supply details of the task such as title, a description, a due date or other criteria upon which performance of the task will be triggered, and recurrence intervals if any. In some embodiments, the messages may further include information comprising an identification of the client computing device 1208 and a channel for communicating with the client computing device 1208. The digital assistant 1202 may then call the task manager APIs 1214 to cause the task entry to be generated for the task by engaging the scheduler service 1210.

The task entry may include various information. For example, the task entry may include a description of the task (which may include a title), the due date or other criteria for initiating the task (e.g., time at which the task is to be performed). The task description that is part of a given task entry can help to uniquely identify the task. For example, if a task entry is generated for a task of calling in a patient prescription to a pharmacy, the task description in the task entry can be used to differentiate the task from another scheduled task for a different patient. Generating the task entry may further comprise generating metadata associated with the task and with a context of the end user conversation with the digital assistant 1202. In some embodiments, the metadata may further comprise an identification of a selected skill of a plurality of skills of the digital assistant 1202 for processing steps of the task. The description, the task initiating criteria, and the metadata may be stored as the task entry in a table of a database, such as the database 1226.

In another embodiment, a task entry may be generated without any scheduling input form the end user. For instance, a task entry may be generated automatically by the digital assistant 1202 based on a conversation of the end user. For example, when a healthcare provider speaks with a patient and the ambient recording service is used to record and transcribe the conversation, the text of the transcription may be analyzed by the aforementioned one or more machine learning models of or associated with the digital assistant 1202, and one or more tasks to be scheduled may be identified as a result. The identified tasks can be saved to the database 1226 of the task manager and notification service layer 1204, and task entries for the tasks may be created by invoking the task manager APIs 1214 and engaging the scheduler service 1210 as described above. Such task entries created automatically at the instruction of the digital assistant 1202 may include the same information described above with respect to task entries created at the express instruction of the end user, including metadata.

Irrespective of the mechanism by which task entries are generated, the task manager and notification service layer 1204 may be responsible for deduplicating tasks and sorting tasks based on priority and triggering criteria (e.g., due date). If similar tasks are proposed by the digital assistant 1202, the associated description of the task may be analyzed and used to reject duplicate tasks. If an end user asks the digital assistant 1202 to list the tasks associated with all the stored task entries, the digital assistant 1202 can obtain a list of the tasks by querying the task manager and notification service layer 1204. The tasks may then be presented to the end user on a user interface of the client computing device 1208. In some embodiments, the presented tasks may be sorted based on triggering criteria (e.g., due date) and priority by default. In some embodiments, the end user can optionally delete a task from the list, mark a task as completed, mark a task for later completion, or change a single occurrence task to a recurring task.

As previously mentioned, a feature of the task manager and notification service layer 1204 is generating notifications and notification messages. For example, notification service 1218 of the task manager and notification service layer 1204 may generate a notification entry for each task entry, and may associate the notification entry with the task entry in the table of the database 1226. The notification entry can include, for example, notification instructions for controlling how a notification is to be generated and later provided to the client computing device 1208. Upon detecting satisfaction of the criteria for initiating the task as identified in the task entry, the notification service 1218 can generate the notification based on the notification instructions, append the metadata to the notification to generate a notification message, and send the notification message 1224 to the client computing device 1208 based on the notification instructions.

A notification for a task can be generated in multiple ways. For example, a notification for a task may be automatically generated by the notification service 1218 of the task manager and notification service layer 1204 as described above—i.e., upon occurrence of the identified criteria for initiating the associated task. Alternatively, a notification for a task may be generated when a service or skill of the cloud service provider platform 1206 needs to notify the end user about a status of some operation related to the task (e.g., generation of or a recognized failure to generate a SOAP note). Thus, the notification messages generated by the notification service 1218 may be related to: notifications that are triggered by the digital assistant 1202 (e.g., alerting the doctor about health conditions of patient when lab result is ready); notifications that indicate a state change (e.g., when a SOAP note is ready for review for the patient); notifications for tasks that are set by the end user (e.g., call in a prescription refill for a patient); and notifications generated by rules, which are notifications set by the end user or configured by the digital assistant 1202 from past end user behavior (e.g., at 6 AM every morning, show a given healthcare provider his/her patient appointments for the day).

The notification messages generated by the notification service 1218 are sent to the client computing device 1208 at the appropriate times. Notification messages 1224 can be delivered directly to the client application of the client computing device 1208 using the same (CMM) and payload format as any other messages transmitted from the cloud service provider platform 1206 to the client computing device 1208, and vice versa. In some embodiments, the cloud service provider platform 1206 caches a token and channel metadata provided by the client computing device 1208 when an end user initiates a conversation with the cloud service provider platform 1206 (e.g., at registration of the client computing device 1208). When it becomes necessary to send a notification to the client computing device 1208, the cached token and channel metadata can be used by the cloud service provider platform 1206 to identify the client computing device 1208 and the channel for communication therewith, ensuring proper delivery of generated notifications to the client computing device 1208.

In some embodiments, the notification messages can be sent to the client computing device 1208 push notifications (e.g., APNS for an iOS operating system or FCM for an Android operating system). In some embodiments, in-app notifications are also supported and may appear as an in-line popup on a user interface of the client computing device 1208. In some embodiments, notification messages may be overlayed on one another on a user interface of a client computing device, as previously described regarding task panel overlays.

In contrast to a typical mobile, web, or desktop application where a user manually an exclusively sets preferences, embodiments described herein can offer AI-powered user settings based on user context. More specifically, cloud service provider platform embodiments can leverage digital assistant recommendations to provide an optimized end user experience by automatically adjusting certain configurations based on the end user context. For instance, turning off low-priority user notifications if a healthcare provider end user is busy speaking to a patient and an ambient recording operation is ongoing, or turning on a do not disturb feature based on a location of the end user (e.g., deferring all low priority notifications if the healthcare provider is in a medical lab).

In some embodiments, a notification message can be categorized or assigned a priority level classification, such as by the notification instructions of the notification entry. The priority level classification can be subsequently used to determine whether a notification of a notification message sent to the client computing device 1208 should be displayed immediately or if display of the notification should be deferred until a later time. For example, at a time of sending a notification message 1224 to the client computing device 1208, a priority level classification of the associated notification can be compared with a priority level classification (or category, etc.) of an ongoing interaction of an end user. When the priority level classification assigned to the notification is higher than the priority level classification of the ongoing interaction, an instruction may be sent to the client computing device 1208 to suspend the ongoing interaction and to immediately display the notification. Contrarily, when the priority level classification of the ongoing interaction is higher than the priority level classification assigned to the notification, an instruction may be sent to the client computing device 1208 to defer displaying the notification until the ongoing interaction has ended. In some embodiments, a notification message conveying a low priority notification may be marked or otherwise include information indicating that the message is, for example, "deferrable." In some embodiments, a notification message conveying a high priority notification may be similarly appropriately marked. When display of a notification is deferred, the associated notification message can be queued, such as by the notification manager 1220 of the task manager and notification service layer 1204 until the ongoing interaction of the end user has completed. Upon completion of the ongoing interaction, the queued notification is presented to the end user (e.g., in the client application and/or by a device-specific push notification). Other methods for determining whether to display or delay displaying of a notification are possible in other embodiments.

Examples of situations in which it may be desirable to either immediately display or temporarily defer displaying a task notification are provided below. In one example of a situation in which it may be desirable to immediately display a task notification, the task notification may inform a healthcare provider that awaited diagnostic test results for a patient are available or are retrievable for viewing and, for example, the underlying test is related to a potentially serious condition of the patient and/or the healthcare provider is currently interacting with the patient and the test results are relevant to the interaction. In another example, a healthcare provider may be engaged in a low priority conversation with the digital assistant 1202 of the cloud service provider platform 1206 when the cloud service provider platform receives a notification message from the notification service 1218 indicating that a SOAP note is ready for a patient. In this case, the notification can be immediately displayed without negatively affecting the ongoing interaction of the healthcare provider with the cloud service provider platform 1206, as the healthcare provider can simply continue the ongoing interaction and whenever ready, tap on notification to view the details thereof. Situations in which it may be desirable to defer displaying a task notification until a current interaction of an end user is completed includes a situation where immediately displaying the notification could undesirably impact an ongoing interaction of the end user with skill or related to the context of the notification. For example, it may be undesirable to immediately display a notification when a healthcare provider is in the process of using an ambient service of a cloud service provider platform to record a conversation with a patient.

When an end user taps on or otherwise selects or engages a displayed notification, a message is returned to the cloud service provider platform 1206 indicating that the end user has elected to review the notification. The return message includes the metadata from the notification message. Upon receipt of the return message, the digital assistant 1202 can route the task associated with the notification to the selected skill identified in the metadata. In some embodiments, the task may be assigned a category prior to generation of the metadata, and the selected skill identified in the metadata may be a skill of the same category.

In some implementations, the notifications can be used to trigger or start a contextually relevant conversation between the end user and the digital assistant 1202. The context for the conversation may be derived, at least in part, from the metadata associated with the notification. For example, upon a healthcare provider engaging a notification generated for a task comprising calling in a refill prescription for a patient, the digital assistant 1202 can launch a conversation that queries the healthcare provider about the type and quantity of the medication being refilled. Upon engaging a displayed notification, the client application of the client computing device 1208 may also navigate the end user to a desired state in a conversation. For example, this could be either a user interface where a healthcare provider can view the details of the notification or it may be some actions suggested by the digital assistant 1202 based on the notification.

Upon receiving a return message from the client computing device 1208 (which may be configured as an event message) with the metadata as at least part of the message payload, and routing the task to the selected skill identified in the metadata, the selected skill can perform the task by processing steps of the task using a task flow of the skill. In this regard, any ongoing conversational flow between the end user and the selected skill can be suspended before the selected skill performs the task. In response to performing the task by the selected skill, the cloud service provider platform 1206 may send a response message to the client computing device 1208. The response message may include a payload content responsive to the task performed (e.g., the payload content may include a patient x-ray retrieved from an electronic health records store by the digital assistant 1202. Receipt of the response message by the client computing device 1208 may cause the client application to render the payload content of the response message on a user interface of a display of the client computing device 1208. The end user may interact with the user interface and further interaction between the end user and the cloud service provider platform 1206 may result.

Illustrative Methods

Figure 13:
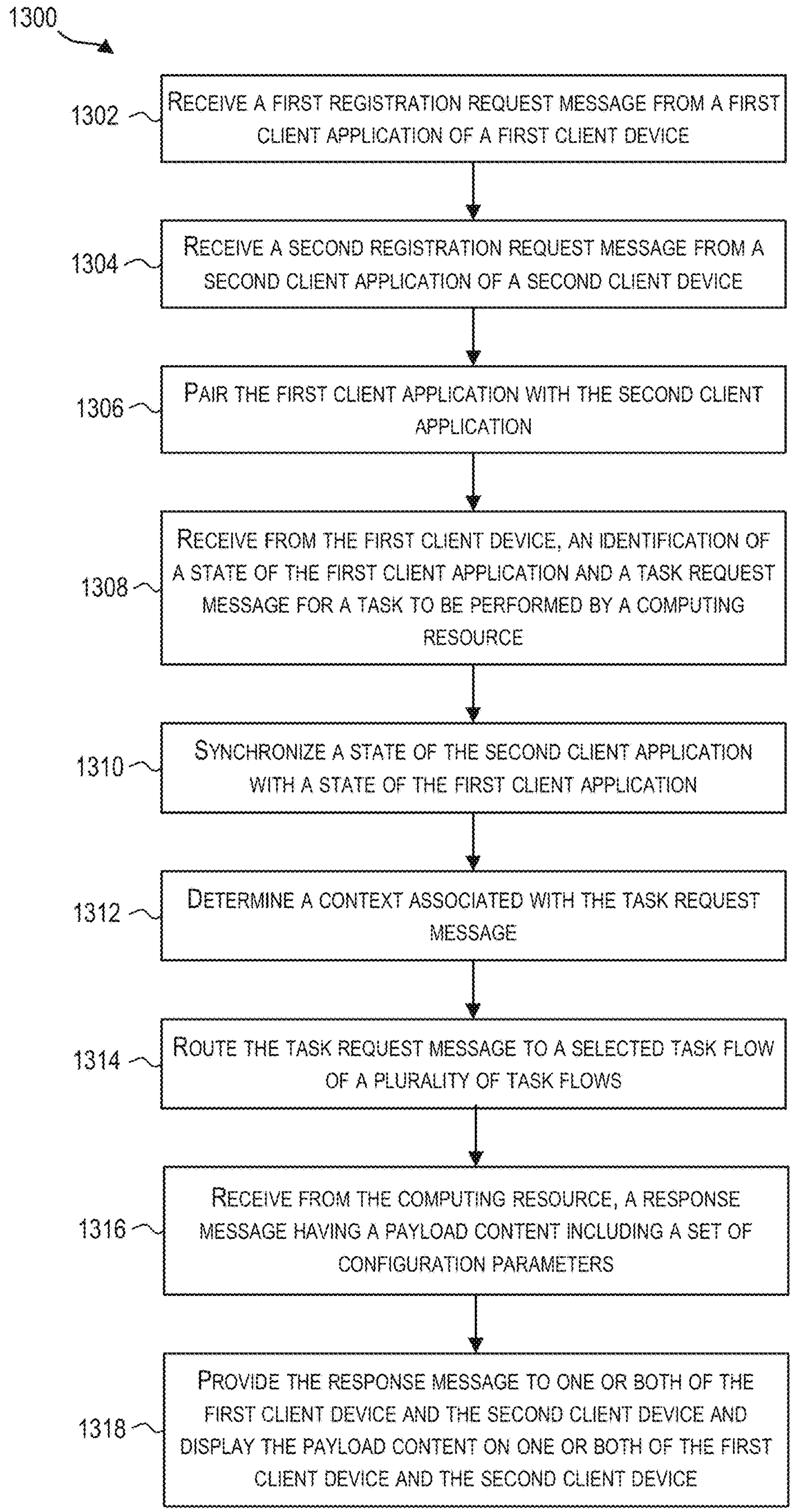
FIG. 13 depicts a method for centrally and remotely controlling the state and navigation of a client application user interface, according to some embodiments.

FIG. 13 is a process flow for intelligently controlling paired applications. The processing depicted in FIG. 13 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 13 and described below is intended to be illustrative and non-limiting. Although FIG. 13 depicts the various processing steps occurring in a particular sequence or order, this is not intended to be limiting. In certain alternative embodiments, the steps may be performed in some different order or some steps may also be performed in parallel. In certain embodiments, such as in the embodiment depicted in FIG. 2, the processing may be performed by a system (e.g., system 200).

At block 1302, a first registration request message is received from a first client application executing on a first client device. The first registration request message includes information that at least identifies the first client device and capabilities of the first client device. The first client application may be a mobile client application and the first client device may be a mobile computing device, or the first client application may be a desktop client application and the first client device may be a desktop computing device.

At block 1304, a second registration request message is received from a second client application executing on a second client device. The second registration request message includes information that at least identifies the second client device and capabilities of the second client device. The second client application may be a mobile client application and the second client device may be a mobile computing device, or the second client application may be a desktop client application and the second client device may be a desktop computing device.

The identification of the first client device and the second client device that is included in the information of the registration request messages can, in some cases, be used by the computing resource when communicating with the first client device and the second client device. The capabilities of the first client device and the second client device can vary. For example, when one of the first client device and the second client device is a mobile computing device, the capabilities can include sound recording (via a microphone) or image capture (via a camera). When one of the first client device and the second client device is a desktop computing device, the capabilities can include audio playback (via external speakers) or large-scale high-resolution display (via one or more monitors).

At block 1306, the first client application is paired with the second client application upon registering the first client device and the second client device with a computing resource (e.g., a cloud service provider platform). The computing resource then has knowledge of both client applications and can concurrently send information to, update the state of, etc., both client applications. Pairing of the applications may also involve, for example, causing the first client device and the second client device to each subscribe to receive notifications from the computing resource, and thereafter publishing a notification from the computing resource to the first client device and the second client device any time a client device is registered with or unregistered from the computing resource.

At block 1308, an identification of a state of the first client application and a task request message corresponding to a task to be performed by the computing resource is received from the first client device in response to an end user interaction with the first client application. In some cases, the task associated with the task request message may be a task to be performed by one or more skills associated with a digital assistant of the computing resource. For example, the task may be completing various healthcare forms via end user dictation, generating healthcare (e.g., SOAP) notes by recording and transcribing a spoken conversation between a healthcare provider and a patient, or clinical automation tasks such as retrieving patient records or medical images, or ordering prescriptions. The end user interaction with the first client application may be, for example, a gesture-based interaction with a widget or another interface object presented by the first client application on a user interface of the first client device, or an interaction based on a natural language utterance of the end user.

At block 1310 a state of the second client application is synchronized with the state of the first client application. Synchronizing the state of the second client application with the state of the first client application allows both applications to display the same information for viewing and interaction by the end user. Synchronizing the state of the second client application with the state of the first client application also helps to facilitate a seamless experience when the end user transitions between the first client device and the second client device while performing a task.

At block 1312, a context associated with the task request message is determined. The context may be determined, for example, from various information in the task request message, a current state of the client application, etc.

At block 1314, the task request message is routed to a selected task flow of a plurality of task flows associated with the computing resource based at least in part on the context associated with the task request message. The task flow can be a task flow of a skill associated with the digital assistant or a service of the cloud service provider platform. The selected task flow can be used to perform the task by processing steps of the task. In some cases, a single task flow may not be capable of performing the entire task. In such a case, the selected task may perform part of the task and then hand off the remainder of the task to another task flow.

At block 1316, a response message is received from the computing resource. The response message is generated by the computing resource in response to the task being executed by processing steps of the task by the selected task flow. The response message has a payload content including a set of configuration parameters that define a layout of the payload content. For example, the configuration parameters may be related to an advanced form layout CMM format for use in presenting task response information, whereby the response information can be presented as one or more forms, and wherein each form can have multiple rows, with each row having one or more columns, and each column have one or more fields.

At block 1318, the response message is provided to one or both of the first client device and the second client device. Providing the response message to one or both of the first client device and the second client device causes the payload content of the response message to be displayed on one or both of a first client device display and a second client device display according to the configuration parameters and the capabilities of the first client device and the second client device. When provided to a client device in CMM format, the associated client application understands how to translate response message payload content in CMM format into a visual representation for display on the client device. The visual representation may include a number of interface objects by which an end user can interact with the cloud service provider platform and the services and digital assistant thereof. For example, the payload content may be rendered with one or more widgets, such as action buttons, that can be used to activate services of the cloud service provider platform or converse with the digital assistant. One or more designated areas may also be provided in which to present information that is sent to the mobile computing device by the cloud service provider platform.

Examples of Cloud Infrastructure

The term cloud service is generally used to refer to a service that is made available by a cloud service provider (CSP) to users (e.g., cloud service customers) on demand (e.g., via a subscription model) using systems and infrastructure (cloud infrastructure) provided by the CSP. Typically, the servers and systems that make up the CSP's infrastructure are separate from the user's own on-premise servers and systems. Users can thus avail themselves of cloud services provided by the CSP without having to purchase separate hardware and software resources for the services. Cloud services are designed to provide a subscribing user easy, scalable access to applications and computing resources without the user having to invest in procuring the infrastructure that is used for providing the services.

There are several cloud service providers that offer various types of cloud services. As discussed herein, there are various types or models of cloud services including infrastructure as a service (IaaS), software as a service (SaaS), platform as a service (PaaS), and others. A user can subscribe to one or more cloud services provided by a CSP. The user can be any entity such as an individual, an organization, an enterprise, and the like. When a user subscribes to or registers for a service provided by a CSP, a tenancy or an account is created for that user. The user can then, via this account, access the subscribed-to one or more cloud resources associated with the account.

As noted above, IaaS is one particular type of cloud computing. IaaS can be configured to provide virtualized computing resources over a public network (e.g., the Internet). In an IaaS model, a cloud computing provider can host the infrastructure components (e.g., servers, storage devices, network nodes (e.g., hardware), deployment software, platform virtualization (e.g., a hypervisor layer), or the like). In some cases, an IaaS provider may also supply a variety of services to accompany those infrastructure components (example services include billing software, monitoring software, logging software, load balancing software, clustering software, etc.). Thus, as these services may be policy-driven, IaaS users may be able to implement policies to drive load balancing to maintain application availability and performance.

In some instances, IaaS customers may access resources and services through a wide area network (WAN), such as the Internet, and can use the cloud provider's services to install the remaining elements of an application stack. For example, the user can log in to the IaaS platform to create virtual machines (VMs), install operating systems (OSs) on each VM, deploy middleware such as databases, create storage buckets for workloads and backups, and even install enterprise software into that VM. Customers can then use the provider's services to perform various functions, including balancing network traffic, troubleshooting application issues, monitoring performance, managing disaster recovery, etc.

In most cases, a cloud computing model will require the participation of a cloud provider. The cloud provider may, but need not be, a third-party service that specializes in providing (e.g., offering, renting, selling) IaaS. An entity might also opt to deploy a private cloud, becoming its own provider of infrastructure services.

In some examples, IaaS deployment is the process of putting a new application, or a new version of an application, onto a prepared application server or the like. It may also include the process of preparing the server (e.g., installing libraries, daemons, etc.). This is often managed by the cloud provider, below the hypervisor layer (e.g., the servers, storage, network hardware, and virtualization). Thus, the customer may be responsible for handling (OS), middleware, and/or application deployment (e.g., on self-service virtual machines (e.g., that can be spun up on demand) or the like.

In some examples, IaaS provisioning may refer to acquiring computers or virtual hosts for use, and even installing needed libraries or services on them. In most cases, deployment does not include provisioning, and the provisioning may need to be performed first.

In some cases, there are two different challenges for IaaS provisioning. First, there is the initial challenge of provisioning the initial set of infrastructure before anything is running. Second, there is the challenge of evolving the existing infrastructure (e.g., adding new services, changing services, removing services, etc.) once everything has been provisioned. In some cases, these two challenges may be addressed by enabling the configuration of the infrastructure to be defined declaratively. In other words, the infrastructure (e.g., what components are needed and how they interact) can be defined by one or more configuration files. Thus, the overall topology of the infrastructure (e.g., what resources depend on which, and how they each work together) can be described declaratively. In some instances, once the topology is defined, a workflow can be generated that creates and/or manages the different components described in the configuration files.

In some examples, an infrastructure may have many interconnected elements. For example, there may be one or more virtual private clouds (VPCs) (e.g., a potentially on-demand pool of configurable and/or shared computing resources), also known as a core network. In some examples, there may also be one or more inbound/outbound traffic group rules provisioned to define how the inbound and/or outbound traffic of the network will be set up and one or more virtual machines (VMs). Other infrastructure elements may also be provisioned, such as a load balancer, a database, or the like. As more and more infrastructure elements are desired and/or added, the infrastructure may incrementally evolve.

In some instances, continuous deployment techniques may be employed to enable deployment of infrastructure code across various virtual computing environments. Additionally, the described techniques can enable infrastructure management within these environments. In some examples, service teams can write code that is desired to be deployed to one or more, but often many, different production environments (e.g., across various different geographic locations, sometimes spanning the entire world). However, in some examples, the infrastructure on which the code will be deployed must first be set up. In some instances, the provisioning can be done manually, a provisioning tool may be utilized to provision the resources, and/or deployment tools may be utilized to deploy the code once the infrastructure is provisioned.

Figure 14:
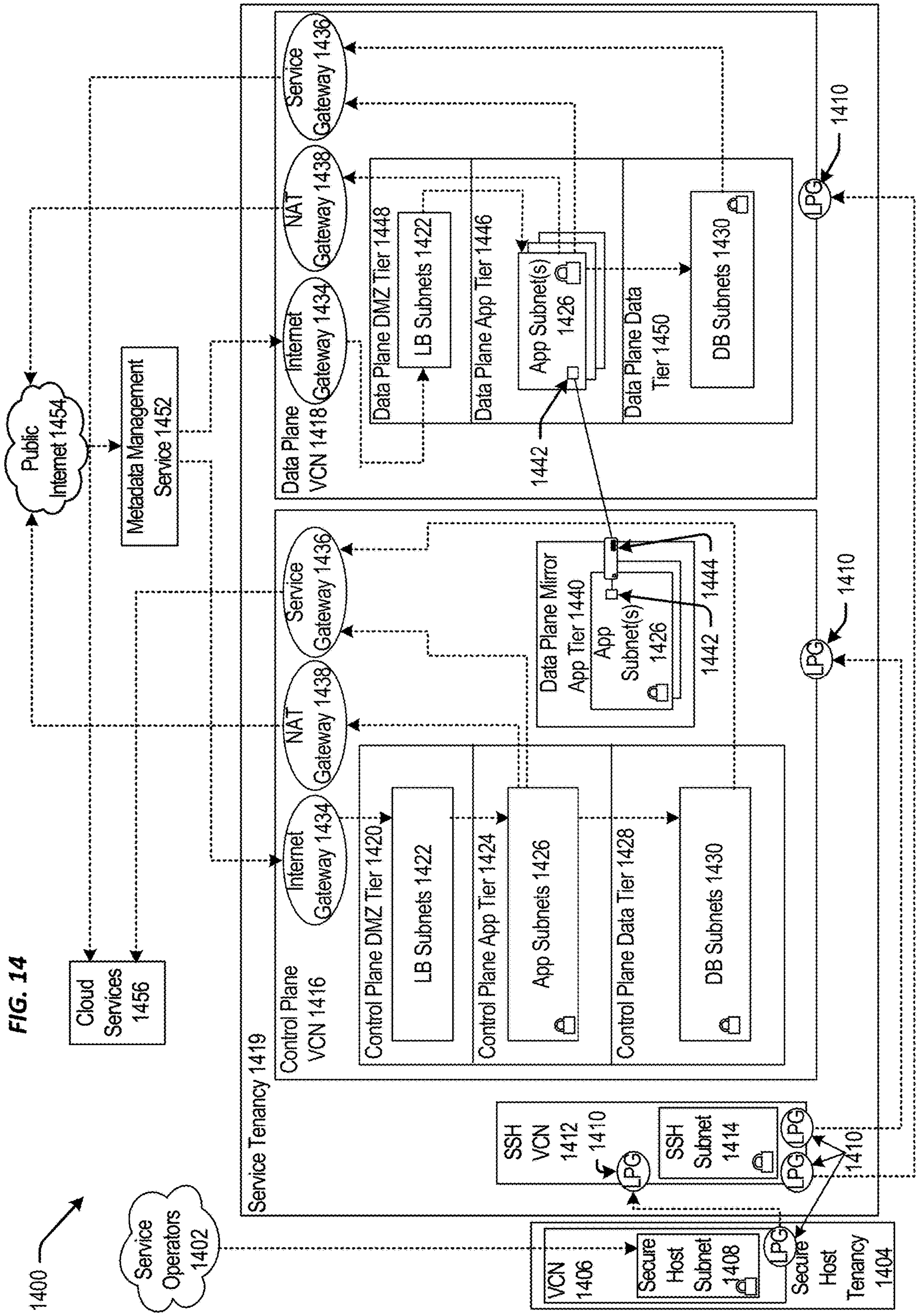
FIG. 14 is a block diagram illustrating one pattern for implementing a cloud infrastructure as a service system according to certain embodiments.

FIG. 14 is a block diagram 1400 illustrating an example pattern of an IaaS architecture, according to at least one embodiment. Service operators 1402 can be communicatively coupled to a secure host tenancy 1404 that can include a virtual cloud network (VCN) 1406 and a secure host subnet 1408. In some examples, the service operators 1402 may be using one or more client computing devices, which may be portable handheld devices (e.g., an iPhone®, cellular telephone, an iPad®, computing tablet, a personal digital assistant (PDA)) or wearable devices (e.g., a Google Glass® head mounted display), running software such as Microsoft Windows Mobile®, and/or a variety of mobile operating systems such as iOS, Windows Phone, Android, BlackBerry 8, Palm OS, and the like, and being Internet, e-mail, short message service (SMS), Blackberry®, or other communication protocol enabled. Alternatively, the client computing devices can be general purpose personal computers including, by way of example, personal computers and/or laptop computers running various versions of Microsoft Windows®, Apple Macintosh®, and/or Linux operating systems. The client computing devices can be workstation computers running any of a variety of commercially-available UNIX® or UNIX-like operating systems, including without limitation the variety of GNU/Linux operating systems, such as for example, Google Chrome OS. Alternatively, or in addition, client computing devices may be any other electronic device, such as a thin-client computer, an Internet-enabled gaming system (e.g., a Microsoft Xbox gaming console with or without a Kinect® gesture input device), and/or a personal messaging device, capable of communicating over a network that can access the VCN 1406 and/or the Internet.

The VCN 1406 can include a local peering gateway (LPG) 1410 that can be communicatively coupled to a secure shell (SSH) VCN 1412 via an LPG 1410 contained in the SSH VCN 1412. The SSH VCN 1412 can include an SSH subnet 1414, and the SSH VCN 1412 can be communicatively coupled to a control plane VCN 1416 via the LPG 1410 contained in the control plane VCN 1416. Also, the SSH VCN 1412 can be communicatively coupled to a data plane VCN 1418 via an LPG 1410. The control plane VCN 1416 and the data plane VCN 1418 can be contained in a service tenancy 1419 that can be owned and/or operated by the IaaS provider.

The control plane VCN 1416 can include a control plane demilitarized zone (DMZ) tier 1420 that acts as a perimeter network (e.g., portions of a corporate network between the corporate intranet and external networks). The DMZ-based servers may have restricted responsibilities and help keep breaches contained. Additionally, the DMZ tier 1420 can include one or more load balancer (LB) subnet(s) 1422, a control plane app tier 1424 that can include app subnet(s) 1426, a control plane data tier 1428 that can include database (DB) subnet(s) 1430 (e.g., frontend DB subnet(s) and/or backend DB subnet(s)). The LB subnet(s) 1422 contained in the control plane DMZ tier 1420 can be communicatively coupled to the app subnet(s) 1426 contained in the control plane app tier 1424 and an Internet gateway 1434 that can be contained in the control plane VCN 1416, and the app subnet(s) 1426 can be communicatively coupled to the DB subnet(s) 1430 contained in the control plane data tier 1428 and a service gateway 1436 and a network address translation (NAT) gateway 1438. The control plane VCN 1416 can include the service gateway 1436 and the NAT gateway 1438.

The control plane VCN 1416 can include a data plane mirror app tier 1440 that can include app subnet(s) 1426. The app subnet(s) 1426 contained in the data plane mirror app tier 1440 can include a virtual network interface controller (VNIC) 1442 that can execute a compute instance 1444. The compute instance 1444 can communicatively couple the app subnet(s) 1426 of the data plane mirror app tier 1440 to app subnet(s) 1426 that can be contained in a data plane app tier 1446.

The data plane VCN 1418 can include the data plane app tier 1446, a data plane DMZ tier 1448, and a data plane data tier 1450. The data plane DMZ tier 1448 can include LB subnet(s) 1422 that can be communicatively coupled to the app subnet(s) 1426 of the data plane app tier 1446 and the Internet gateway 1434 of the data plane VCN 1418. The app subnet(s) 1426 can be communicatively coupled to the service gateway 1436 of the data plane VCN 1418 and the NAT gateway 1438 of the data plane VCN 1418. The data plane data tier 1450 can also include the DB subnet(s) 1430 that can be communicatively coupled to the app subnet(s) 1426 of the data plane app tier 1446.

The Internet gateway 1434 of the control plane VCN 1416 and of the data plane VCN 1418 can be communicatively coupled to a metadata management service 1452 that can be communicatively coupled to public Internet 1454. Public Internet 1454 can be communicatively coupled to the NAT gateway 1438 of the control plane VCN 1416 and of the data plane VCN 1418. The service gateway 1436 of the control plane VCN 1416 and of the data plane VCN 1418 can be communicatively coupled to cloud services 1456.

In some examples, the service gateway 1436 of the control plane VCN 1416 or of the data plane VCN 1418 can make application programming interface (API) calls to cloud services 1456 without going through public Internet 1454. The API calls to cloud services 1456 from the service gateway 1436 can be one-way: the service gateway 1436 can make API calls to cloud services 1456, and cloud services 1456 can send requested data to the service gateway 1436. But, cloud services 1456 may not initiate API calls to the service gateway 1436.

In some examples, the secure host tenancy 1404 can be directly connected to the service tenancy 1419, which may be otherwise isolated. The secure host subnet 1408 can communicate with the SSH subnet 1414 through an LPG 1410 that may enable two-way communication over an otherwise isolated system. Connecting the secure host subnet 1408 to the SSH subnet 1414 may give the secure host subnet 1408 access to other entities within the service tenancy 1419.

The control plane VCN 1416 may allow users of the service tenancy 1419 to set up or otherwise provision desired resources. Desired resources provisioned in the control plane VCN 1416 may be deployed or otherwise used in the data plane VCN 1418. In some examples, the control plane VCN 1416 can be isolated from the data plane VCN 1418, and the data plane mirror app tier 1440 of the control plane VCN 1416 can communicate with the data plane app tier 1446 of the data plane VCN 1418 via VNICs 1442 that can be contained in the data plane mirror app tier 1440 and the data plane app tier 1446.

In some examples, users of the system, or customers, can make requests, for example create, read, update, or delete (CRUD) operations, through public Internet 1454 that can communicate the requests to the metadata management service 1452. The metadata management service 1452 can communicate the request to the control plane VCN 1416 through the Internet gateway 1434. The request can be received by the LB subnet(s) 1422 contained in the control plane DMZ tier 1420. The LB subnet(s) 1422 may determine that the request is valid, and in response to this determination, the LB subnet(s) 1422 can transmit the request to app subnet(s) 1426 contained in the control plane app tier 1424. If the request is validated and requires a call to public Internet 1454, the call to public Internet 1454 may be transmitted to the NAT gateway 1438 that can make the call to public Internet 1454. Metadata that may be desired to be stored by the request can be stored in the DB subnet(s) 1430.

In some examples, the data plane mirror app tier 1440 can facilitate direct communication between the control plane VCN 1416 and the data plane VCN 1418. For example, changes, updates, or other suitable modifications to configuration may be desired to be applied to the resources contained in the data plane VCN 1418. Via a VNIC 1442, the control plane VCN 1416 can directly communicate with, and can thereby execute the changes, updates, or other suitable modifications to configuration to, resources contained in the data plane VCN 1418.

In some embodiments, the control plane VCN 1416 and the data plane VCN 1418 can be contained in the service tenancy 1419. In this case, the user, or the customer, of the system may not own or operate either the control plane VCN 1416 or the data plane VCN 1418. Instead, the IaaS provider may own or operate the control plane VCN 1416 and the data plane VCN 1418, both of which may be contained in the service tenancy 1419. This embodiment can enable isolation of networks that may prevent users or customers from interacting with other users', or other customers', resources. Also, this embodiment may allow users or customers of the system to store databases privately without needing to rely on public Internet 1454, which may not have a desired level of threat prevention, for storage.

In other embodiments, the LB subnet(s) 1422 contained in the control plane VCN 1416 can be configured to receive a signal from the service gateway 1436. In this embodiment, the control plane VCN 1416 and the data plane VCN 1418 may be configured to be called by a customer of the IaaS provider without calling public Internet 1454. Customers of the IaaS provider may desire this embodiment since database(s) that the customers use may be controlled by the IaaS provider and may be stored on the service tenancy 1419, which may be isolated from public Internet 1454.

Figure 15:
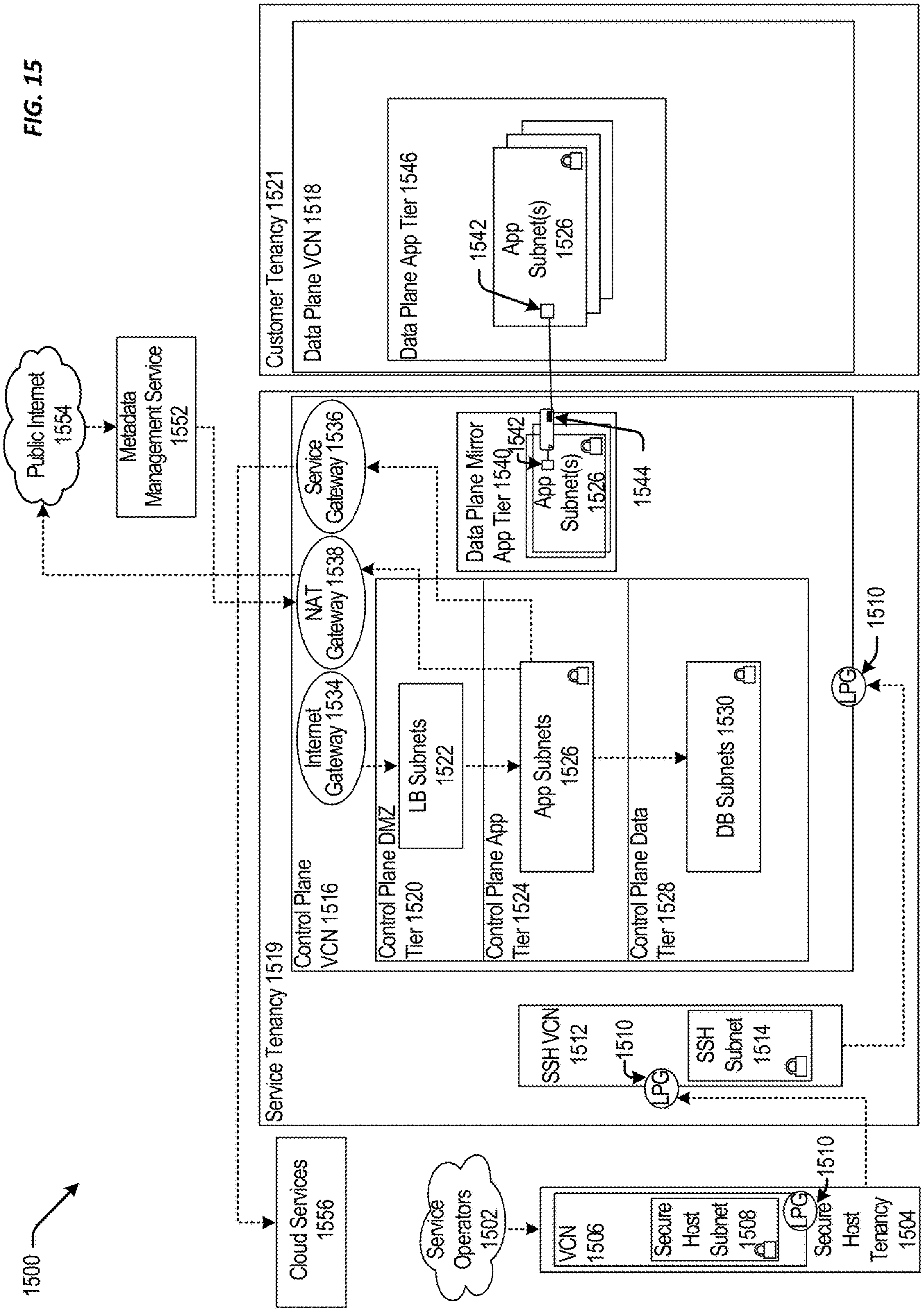
FIG. 15 is a block diagram illustrating another pattern for implementing a cloud infrastructure as a service system according to certain embodiments.

FIG. 15 is a block diagram 1500 illustrating another example pattern of an IaaS architecture, according to at least one embodiment. Service operators 1502 (e.g., service operators 1402 of FIG. 14) can be communicatively coupled to a secure host tenancy 1504 (e.g., the secure host tenancy 1404 of FIG. 14) that can include a virtual cloud network (VCN) 1506 (e.g., the VCN 1406 of FIG. 14) and a secure host subnet 1508 (e.g., the secure host subnet 1408 of FIG. 14). The VCN 1406 can include a local peering gateway (LPG) 1510 (e.g., the LPG 1410 of FIG. 14) that can be communicatively coupled to a secure shell (SSH) VCN 1512 (e.g., the SSH VCN 1412 of FIG. 14) via an LPG 1510 contained in the SSH VCN 1512. The SSH VCN 1512 can include an SSH subnet 1514 (e.g., the SSH subnet 1414 of FIG. 14), and the SSH VCN 1512 can be communicatively coupled to a control plane VCN 1516 (e.g., the control plane VCN 1416 of FIG. 14) via an LPG 1510 contained in the control plane VCN 1516. The control plane VCN 1516 can be contained in a service tenancy 1519 (e.g., the service tenancy 1419 of FIG. 14), and the data plane VCN 1518

(e.g., the data plane VCN 1418 of FIG. 14) can be contained in a customer tenancy 1521 that may be owned or operated by users, or customers, of the system.

The control plane VCN 1516 can include a control plane DMZ tier 1520 (e.g., the control plane DMZ tier 1420 of FIG. 14) that can include LB subnet(s) 1522 (e.g., LB subnet(s) 1422 of FIG. 14), a control plane app tier 1524 (e.g., the control plane app tier 1424 of FIG. 14) that can include app subnet(s) 1526 (e.g., app subnet(s) 1426 of FIG. 14), a control plane data tier 1528 (e.g., the control plane data tier 1428 of FIG. 14) that can include database (DB) subnet(s) 1530 (e.g., similar to DB subnet(s) 1430 of FIG. 14). The LB subnet(s) 1522 contained in the control plane DMZ tier 1520 can be communicatively coupled to the app subnet(s) 1526 contained in the control plane app tier 1524 and an Internet gateway 1534 (e.g., the Internet gateway 1434 of FIG. 14) that can be contained in the control plane VCN 1516, and the app subnet(s) 1526 can be communicatively coupled to the DB subnet(s) 1530 contained in the control plane data tier 1528 and a service gateway 1536 (e.g., the service gateway 1436 of FIG. 14) and a network address translation (NAT) gateway 1538 (e.g., the NAT gateway 1438 of FIG. 14). The control plane VCN 1516 can include the service gateway 1536 and the NAT gateway 1538.

The control plane VCN 1516 can include a data plane mirror app tier 1540 (e.g., the data plane mirror app tier 1440 of FIG. 14) that can include app subnet(s) 1526. The app subnet(s) 1526 contained in the data plane mirror app tier 1540 can include a virtual network interface controller (VNIC) 1542 (e.g., the VNIC of 1442) that can execute a compute instance 1544 (e.g., similar to the compute instance 1444 of FIG. 14). The compute instance 1544 can facilitate communication between the app subnet(s) 1526 of the data plane mirror app tier 1540 and the app subnet(s) 1526 that can be contained in a data plane app tier 1546 (e.g., the data plane app tier 1446 of FIG. 14) via the VNIC 1542 contained in the data plane mirror app tier 1540 and the VNIC 1542 contained in the data plane app tier 1546.

The Internet gateway 1534 contained in the control plane VCN 1516 can be communicatively coupled to a metadata management service 1552 (e.g., the metadata management service 1452 of FIG. 14) that can be communicatively coupled to public Internet 1554 (e.g., public Internet 1454 of FIG. 14). Public Internet 1554 can be communicatively coupled to the NAT gateway 1538 contained in the control plane VCN 1516. The service gateway 1536 contained in the control plane VCN 1516 can be communicatively coupled to cloud services 1556 (e.g., cloud services 1456 of FIG. 14).

In some examples, the data plane VCN 1518 can be contained in the customer tenancy 1521. In this case, the IaaS provider may provide the control plane VCN 1516 for each customer, and the IaaS provider may, for each customer, set up a unique compute instance 1544 that is contained in the service tenancy 1519. Each compute instance 1544 may allow communication between the control plane VCN 1516, contained in the service tenancy 1519, and the data plane VCN 1518 that is contained in the customer tenancy 1521. The compute instance 1544 may allow resources, that are provisioned in the control plane VCN 1516 that is contained in the service tenancy 1519, to be deployed or otherwise used in the data plane VCN 1518 that is contained in the customer tenancy 1521.

In other examples, the customer of the IaaS provider may have databases that live in the customer tenancy 1521. In this example, the control plane VCN 1516 can include the data plane mirror app tier 1540 that can include app subnet(s) 1526. The data plane mirror app tier 1540 can reside in the data plane VCN 1518, but the data plane mirror app tier 1540 may not live in the data plane VCN 1518. That is, the data plane mirror app tier 1540 may have access to the customer tenancy 1521, but the data plane mirror app tier 1540 may not exist in the data plane VCN 1518 or be owned or operated by the customer of the IaaS provider. The data plane mirror app tier 1540 may be configured to make calls to the data plane VCN 1518 but may not be configured to make calls to any entity contained in the control plane VCN 1516. The customer may desire to deploy or otherwise use resources in the data plane VCN 1518 that are provisioned in the control plane VCN 1516, and the data plane mirror app tier 1540 can facilitate the desired deployment, or other usage of resources, of the customer.

In some embodiments, the customer of the IaaS provider can apply filters to the data plane VCN 1518. In this embodiment, the customer can determine what the data plane VCN 1518 can access, and the customer may restrict access to public Internet 1554 from the data plane VCN 1518. The IaaS provider may not be able to apply filters or otherwise control access of the data plane VCN 1518 to any outside networks or databases. Applying filters and controls by the customer onto the data plane VCN 1518, contained in the customer tenancy 1521, can help isolate the data plane VCN 1518 from other customers and from public Internet 1554.

In some embodiments, cloud services 1556 can be called by the service gateway 1536 to access services that may not exist on public Internet 1554, on the control plane VCN 1516, or on the data plane VCN 1518. The connection between cloud services 1556 and the control plane VCN 1516 or the data plane VCN 1518 may not be live or continuous. Cloud services 1556 may exist on a different network owned or operated by the IaaS provider. Cloud services 1556 may be configured to receive calls from the service gateway 1536 and may be configured to not receive calls from public Internet 1554. Some cloud services 1556 may be isolated from other cloud services 1556, and the control plane VCN 1516 may be isolated from cloud services 1556 that may not be in the same region as the control plane VCN 1516. For example, the control plane VCN 1516 may be located in "Region 1," and cloud service "Deployment 7," may be located in Region 1 and in "Region 2." If a call to Deployment 7 is made by the service gateway 1536 contained in the control plane VCN 1516 located in Region 1, the call may be transmitted to Deployment 7 in Region 1. In this example, the control plane VCN 1516, or Deployment 7 in Region 1, may not be communicatively coupled to, or otherwise in communication with, Deployment 7 in Region 2.

Figure 16:
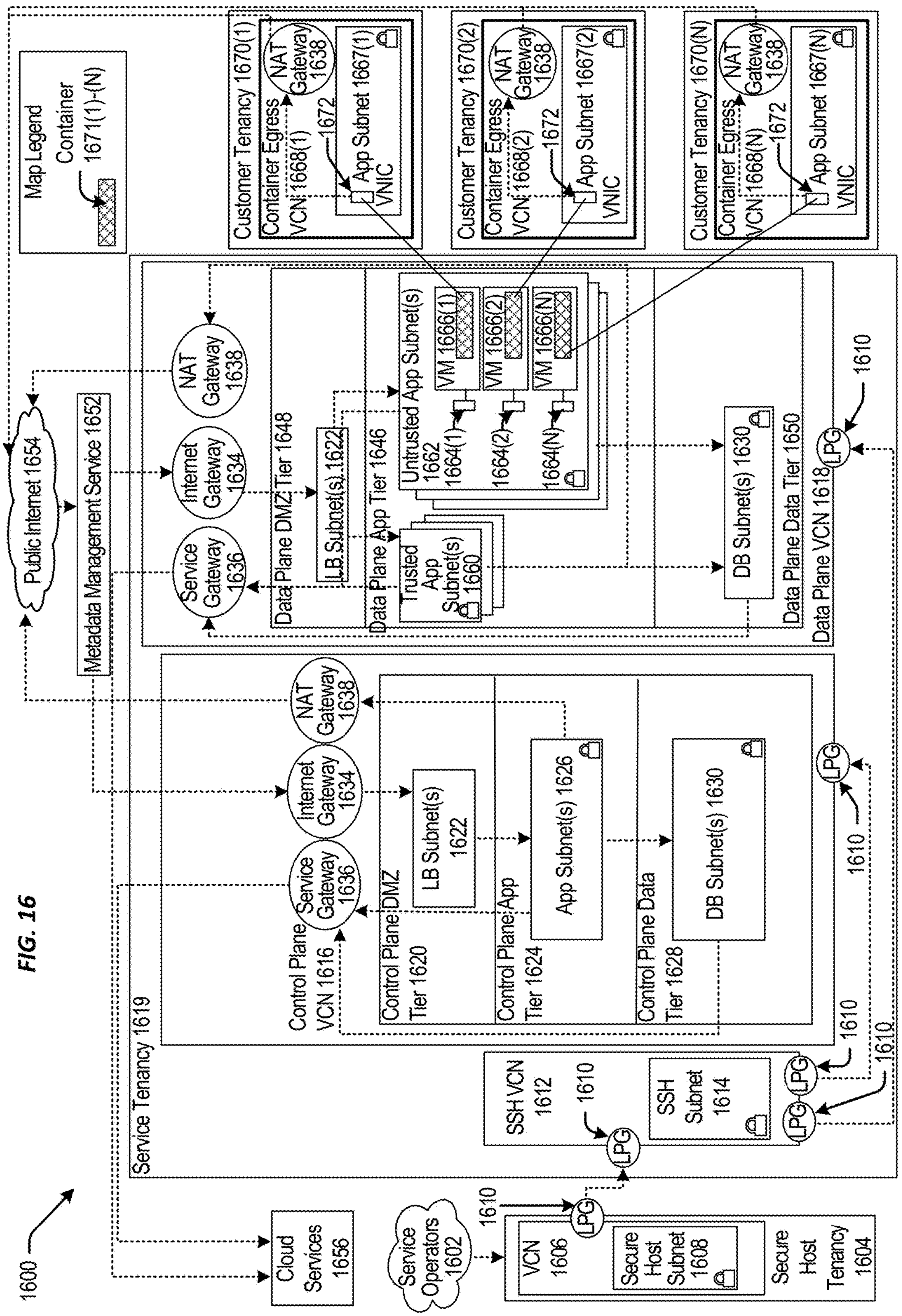
FIG. 16 is a block diagram illustrating another pattern for implementing a cloud infrastructure as a service system according to certain embodiments.

FIG. 16 is a block diagram 1600 illustrating another example pattern of an IaaS architecture, according to at least one embodiment. Service operators 1602 (e.g., service operators 1402 of FIG. 14) can be communicatively coupled to a secure host tenancy 1604 (e.g., the secure host tenancy 1404 of FIG. 14) that can include a virtual cloud network (VCN) 1606 (e.g., the VCN 1406 of FIG. 14) and a secure host subnet 1608 (e.g., the secure host subnet 1408 of FIG. 14). The VCN 1606 can include an LPG 1610 (e.g., the LPG 1410 of FIG. 14) that can be communicatively coupled to an SSH VCN 1612 (e.g., the SSH VCN 1412 of FIG. 14) via an LPG 1610 contained in the SSH VCN 1612. The SSH VCN 1612 can include an SSH subnet 1614 (e.g., the SSH subnet 1414 of FIG. 14), and the SSH VCN 1612 can be communicatively coupled to a control plane VCN 1616 (e.g., the control plane VCN 1416 of FIG. 14) via an LPG

1610 contained in the control plane VCN 1616 and to a data plane VCN 1618 (e.g., the data plane 1418 of FIG. 14) via an LPG 1610 contained in the data plane VCN 1618. The control plane VCN 1616 and the data plane VCN 1618 can be contained in a service tenancy 1619 (e.g., the service tenancy 1419 of FIG. 14).

The control plane VCN 1616 can include a control plane DMZ tier 1620 (e.g., the control plane DMZ tier 1420 of FIG. 14) that can include load balancer (LB) subnet(s) 1622 (e.g., LB subnet(s) 1422 of FIG. 14), a control plane app tier 1624 (e.g., the control plane app tier 1424 of FIG. 14) that can include app subnet(s) 1626 (e.g., similar to app subnet(s) 1426 of FIG. 14), a control plane data tier 1628 (e.g., the control plane data tier 1428 of FIG. 14) that can include DB subnet(s) 1630. The LB subnet(s) 1622 contained in the control plane DMZ tier 1620 can be communicatively coupled to the app subnet(s) 1626 contained in the control plane app tier 1624 and to an Internet gateway 1634 (e.g., the Internet gateway 1434 of FIG. 14) that can be contained in the control plane VCN 1616, and the app subnet(s) 1626 can be communicatively coupled to the DB subnet(s) 1630 contained in the control plane data tier 1628 and to a service gateway 1636 (e.g., the service gateway of FIG. 14) and a network address translation (NAT) gateway 1638 (e.g., the NAT gateway 1438 of FIG. 14). The control plane VCN 1616 can include the service gateway 1636 and the NAT gateway 1638.

The data plane VCN 1618 can include a data plane app tier 1646 (e.g., the data plane app tier 1446 of FIG. 14), a data plane DMZ tier 1648 (e.g., the data plane DMZ tier 1448 of FIG. 14), and a data plane data tier 1650 (e.g., the data plane data tier 1450 of FIG. 14). The data plane DMZ tier 1648 can include LB subnet(s) 1622 that can be communicatively coupled to trusted app subnet(s) 1660 and untrusted app subnet(s) 1662 of the data plane app tier 1646 and the Internet gateway 1634 contained in the data plane VCN 1618. The trusted app subnet(s) 1660 can be communicatively coupled to the service gateway 1636 contained in the data plane VCN 1618, the NAT gateway 1638 contained in the data plane VCN 1618, and DB subnet(s) 1630 contained in the data plane data tier 1650. The untrusted app subnet(s) 1662 can be communicatively coupled to the service gateway 1636 contained in the data plane VCN 1618 and DB subnet(s) 1630 contained in the data plane data tier 1650. The data plane data tier 1650 can include DB subnet(s) 1630 that can be communicatively coupled to the service gateway 1636 contained in the data plane VCN 1618.

The untrusted app subnet(s) 1662 can include one or more primary VNICs 1664(1)-(N) that can be communicatively coupled to tenant virtual machines (VMs) 1666(1)-(N). Each tenant VM 1666(1)-(N) can be communicatively coupled to a respective app subnet 1667(1)-(N) that can be contained in respective container egress VCNs 1668(1)-(N) that can be contained in respective customer tenancies 1670(1)-(N). Respective secondary VNICs 1672(1)-(N) can facilitate communication between the untrusted app subnet(s) 1662 contained in the data plane VCN 1618 and the app subnet contained in the container egress VCNs 1668(1)-(N). Each container egress VCNs 1668(1)-(N) can include a NAT gateway 1638 that can be communicatively coupled to public Internet 1654 (e.g., public Internet 1454 of FIG. 14).

The Internet gateway 1634 contained in the control plane VCN 1616 and contained in the data plane VCN 1618 can be communicatively coupled to a metadata management service 1652 (e.g., the metadata management system 1452 of FIG. 14) that can be communicatively coupled to public Internet 1654. Public Internet 1654 can be communicatively coupled to the NAT gateway 1638 contained in the control plane VCN 1616 and contained in the data plane VCN 1618. The service gateway 1636 contained in the control plane VCN 1616 and contained in the data plane VCN 1618 can be communicatively coupled to cloud services 1656.

In some embodiments, the data plane VCN 1618 can be integrated with customer tenancies 1670. This integration can be useful or desirable for customers of the IaaS provider in some cases such as a case that may desire support when executing code. The customer may provide code to run that may be destructive, may communicate with other customer resources, or may otherwise cause undesirable effects. In response to this, the IaaS provider may determine whether to run code given to the IaaS provider by the customer.

In some examples, the customer of the IaaS provider may grant temporary network access to the IaaS provider and request a function to be attached to the data plane app tier 1646. Code to run the function may be executed in the VMs 1666(1)-(N), and the code may not be configured to run anywhere else on the data plane VCN 1618. Each VM 1666(1)-(N) may be connected to one customer tenancy 1670. Respective containers 1671(1)-(N) contained in the VMs 1666(1)-(N) may be configured to run the code. In this case, there can be a dual isolation (e.g., the containers 1671(1)-(N) running code, where the containers 1671(1)-(N) may be contained in at least the VM 1666(1)-(N) that are contained in the untrusted app subnet(s) 1662), which may help prevent incorrect or otherwise undesirable code from damaging the network of the IaaS provider or from damaging a network of a different customer. The containers 1671(1)-(N) may be communicatively coupled to the customer tenancy 1670 and may be configured to transmit or receive data from the customer tenancy 1670. The containers 1671(1)-(N) may not be configured to transmit or receive data from any other entity in the data plane VCN 1618. Upon completion of running the code, the IaaS provider may kill or otherwise dispose of the containers 1671(1)-(N).

In some embodiments, the trusted app subnet(s) 1660 may run code that may be owned or operated by the IaaS provider. In this embodiment, the trusted app subnet(s) 1660 may be communicatively coupled to the DB subnet(s) 1630 and be configured to execute CRUD operations in the DB subnet(s) 1630. The untrusted app subnet(s) 1662 may be communicatively coupled to the DB subnet(s) 1630, but in this embodiment, the untrusted app subnet(s) may be configured to execute read operations in the DB subnet(s) 1630. The containers 1671(1)-(N) that can be contained in the VM 1666(1)-(N) of each customer and that may run code from the customer may not be communicatively coupled with the DB subnet(s) 1630.

In other embodiments, the control plane VCN 1616 and the data plane VCN 1618 may not be directly communicatively coupled. In this embodiment, there may be no direct communication between the control plane VCN 1616 and the data plane VCN 1618. However, communication can occur indirectly through at least one method. An LPG 1610 may be established by the IaaS provider that can facilitate communication between the control plane VCN 1616 and the data plane VCN 1618. In another example, the control plane VCN 1616 or the data plane VCN 1618 can make a call to cloud services 1656 via the service gateway 1636. For example, a call to cloud services 1656 from the control plane VCN 1616 can include a request for a service that can communicate with the data plane VCN 1618.

Figure 17:
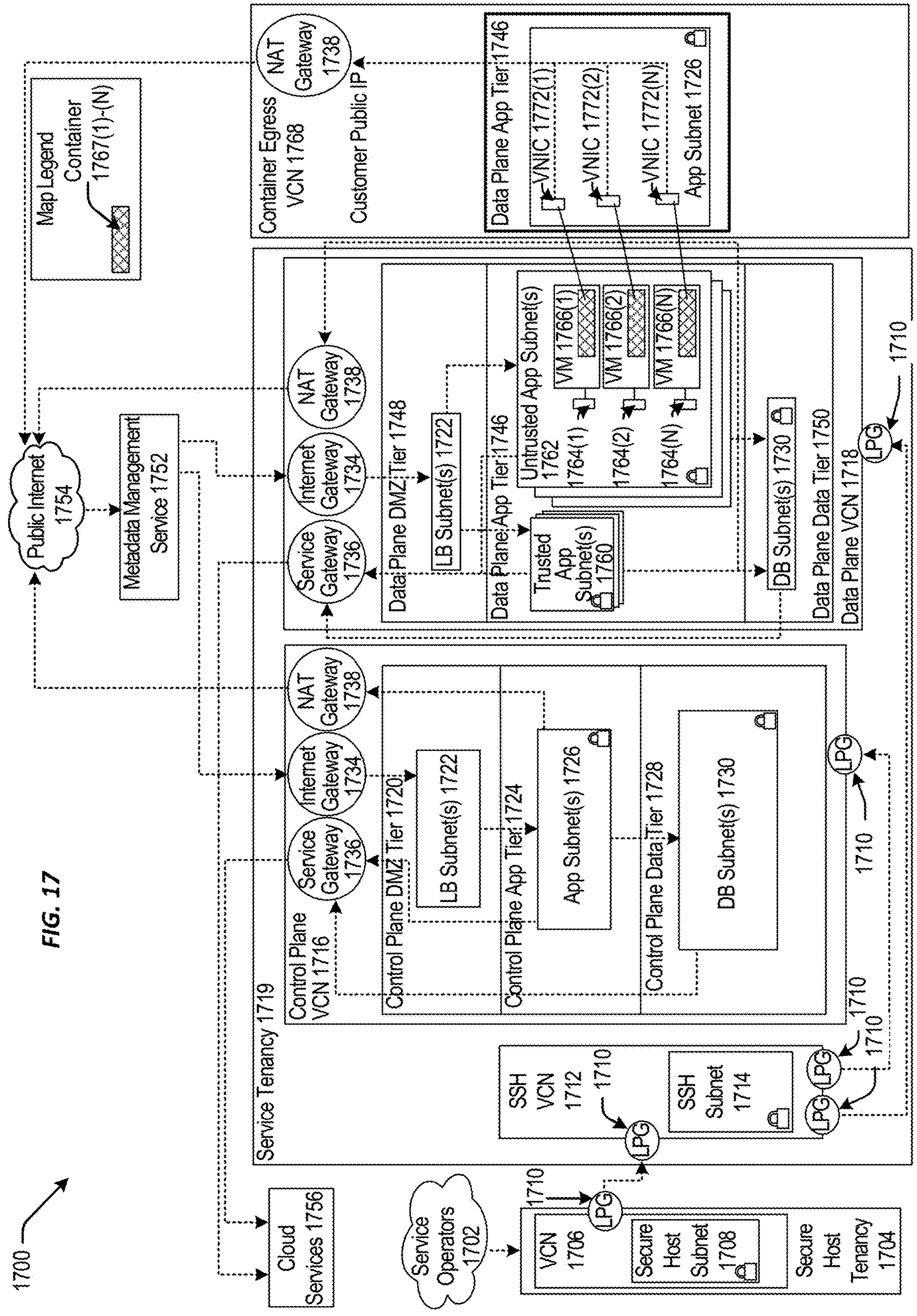
FIG. 17 is a block diagram illustrating another pattern for implementing a cloud infrastructure as a service system according to certain embodiments.

FIG. 17 is a block diagram 1700 illustrating another example pattern of an IaaS architecture, according to at least one embodiment. Service operators 1702 (e.g., service operators 1402 of FIG. 14) can be communicatively coupled to a secure host tenancy 1704 (e.g., the secure host tenancy 1404 of FIG. 14) that can include a virtual cloud network (VCN) 1706 (e.g., the VCN 1406 of FIG. 14) and a secure host subnet 1708 (e.g., the secure host subnet 1408 of FIG. 14). The VCN 1706 can include an LPG 1710 (e.g., the LPG 1410 of FIG. 14) that can be communicatively coupled to an SSH VCN 1712 (e.g., the SSH VCN 1412 of FIG. 14) via an LPG 1710 contained in the SSH VCN 1712. The SSH VCN 1712 can include an SSH subnet 1714 (e.g., the SSH subnet 1414 of FIG. 14), and the SSH VCN 1712 can be communicatively coupled to a control plane VCN 1716 (e.g., the control plane VCN 1416 of FIG. 14) via an LPG 1710 contained in the control plane VCN 1716 and to a data plane VCN 1718 (e.g., the data plane 1418 of FIG. 14) via an LPG 1710 contained in the data plane VCN 1718. The control plane VCN 1716 and the data plane VCN 1718 can be contained in a service tenancy 1719 (e.g., the service tenancy 1419 of FIG. 14).

The control plane VCN 1716 can include a control plane DMZ tier 1720 (e.g., the control plane DMZ tier 1420 of FIG. 14) that can include LB subnet(s) 1722 (e.g., LB subnet(s) 1422 of FIG. 14), a control plane app tier 1724 (e.g., the control plane app tier 1424 of FIG. 14) that can include app subnet(s) 1726 (e.g., app subnet(s) 1426 of FIG. 14), a control plane data tier 1728 (e.g., the control plane data tier 1428 of FIG. 14) that can include DB subnet(s) 1730 (e.g., DB subnet(s) 1530 of FIG. 15). The LB subnet(s) 1722 contained in the control plane DMZ tier 1720 can be communicatively coupled to the app subnet(s) 1726 contained in the control plane app tier 1724 and to an Internet gateway 1734 (e.g., the Internet gateway 1434 of FIG. 14) that can be contained in the control plane VCN 1716, and the app subnet(s) 1726 can be communicatively coupled to the DB subnet(s) 1730 contained in the control plane data tier 1728 and to a service gateway 1736 (e.g., the service gateway of FIG. 14) and a network address translation (NAT) gateway 1738 (e.g., the NAT gateway 1438 of FIG. 14). The control plane VCN 1716 can include the service gateway 1736 and the NAT gateway 1738.

The data plane VCN 1718 can include a data plane app tier 1746 (e.g., the data plane app tier 1446 of FIG. 14), a data plane DMZ tier 1748 (e.g., the data plane DMZ tier 1448 of FIG. 14), and a data plane data tier 1750 (e.g., the data plane data tier 1450 of FIG. 14). The data plane DMZ tier 1748 can include LB subnet(s) 1722 that can be communicatively coupled to trusted app subnet(s) 1760 (e.g., trusted app subnet(s) 1560 of FIG. 15) and untrusted app subnet(s) 1762 (e.g., untrusted app subnet(s) 1562 of FIG. 15) of the data plane app tier 1746 and the Internet gateway 1734 contained in the data plane VCN 1718. The trusted app subnet(s) 1760 can be communicatively coupled to the service gateway 1736 contained in the data plane VCN 1718, the NAT gateway 1738 contained in the data plane VCN 1718, and DB subnet(s) 1730 contained in the data plane data tier 1750. The untrusted app subnet(s) 1762 can be communicatively coupled to the service gateway 1736 contained in the data plane VCN 1718 and DB subnet(s) 1730 contained in the data plane data tier 1750. The data plane data tier 1750 can include DB subnet(s) 1730 that can be communicatively coupled to the service gateway 1736 contained in the data plane VCN 1718.

The untrusted app subnet(s) 1762 can include primary VNICs 1764(1)-(N) that can be communicatively coupled to tenant virtual machines (VMs) 1766(1)-(N) residing within the untrusted app subnet(s) 1762. Each tenant VM 1766(1)-(N) can run code in a respective container 1767(1)-(N), and be communicatively coupled to an app subnet 1726 that can be contained in a data plane app tier 1746 that can be contained in a container egress VCN 1768. Respective secondary VNICs 1772(1)-(N) can facilitate communication between the untrusted app subnet(s) 1762 contained in the data plane VCN 1718 and the app subnet contained in the container egress VCN 1768. The container egress VCN can include a NAT gateway 1738 that can be communicatively coupled to public Internet 1754 (e.g., public Internet 1454 of FIG. 14).

The Internet gateway 1734 contained in the control plane VCN 1716 and contained in the data plane VCN 1718 can be communicatively coupled to a metadata management service 1752 (e.g., the metadata management system 1452 of FIG. 14) that can be communicatively coupled to public Internet 1754. Public Internet 1754 can be communicatively coupled to the NAT gateway 1738 contained in the control plane VCN 1716 and contained in the data plane VCN 1718. The service gateway 1736 contained in the control plane VCN 1716 and contained in the data plane VCN 1718 can be communicatively coupled to cloud services 1756.

In some examples, the pattern illustrated by the architecture of block diagram 1700 of FIG. 17 may be considered an exception to the pattern illustrated by the architecture of block diagram 1500 of FIG. 15 and may be desirable for a customer of the IaaS provider if the IaaS provider cannot directly communicate with the customer (e.g., a disconnected region). The respective containers 1767(1)-(N) that are contained in the VMs 1766(1)-(N) for each customer can be accessed in real-time by the customer. The containers 1767(1)-(N) may be configured to make calls to respective secondary VNICs 1772(1)-(N) contained in app subnet(s) 1726 of the data plane app tier 1746 that can be contained in the container egress VCN 1768. The secondary VNICs 1772(1)-(N) can transmit the calls to the NAT gateway 1738 that may transmit the calls to public Internet 1754. In this example, the containers 1767(1)-(N) that can be accessed in real-time by the customer can be isolated from the control plane VCN 1716 and can be isolated from other entities contained in the data plane VCN 1718. The containers 1767(1)-(N) may also be isolated from resources from other customers.

In other examples, the customer can use the containers 1767(1)-(N) to call cloud services 1756. In this example, the customer may run code in the containers 1767(1)-(N) that requests a service from cloud services 1756. The containers 1767(1)-(N) can transmit this request to the secondary VNICs 1772(1)-(N) that can transmit the request to the NAT gateway that can transmit the request to public Internet 1754. Public Internet 1754 can transmit the request to LB subnet(s) 1722 contained in the control plane VCN 1716 via the Internet gateway 1734. In response to determining the request is valid, the LB subnet(s) can transmit the request to app subnet(s) 1726 that can transmit the request to cloud services 1756 via the service gateway 1736.

It should be appreciated that IaaS architectures 1400, 1500, 1600, 1700 depicted in the figures may have other components than those depicted. Further, the embodiments shown in the figures are only some examples of a cloud infrastructure system that may incorporate an embodiment of the disclosure. In some other embodiments, the IaaS systems may have more or fewer components than shown in the figures, may combine two or more components, or may have a different configuration or arrangement of components.

In certain embodiments, the IaaS systems described herein may include a suite of applications, middleware, and database service offerings that are delivered to a customer in a self-service, subscription-based, elastically scalable, reliable, highly available, and secure manner. An example of such an IaaS system is the Oracle Cloud Infrastructure (OCI) provided by the present assignee.

Figure 18:
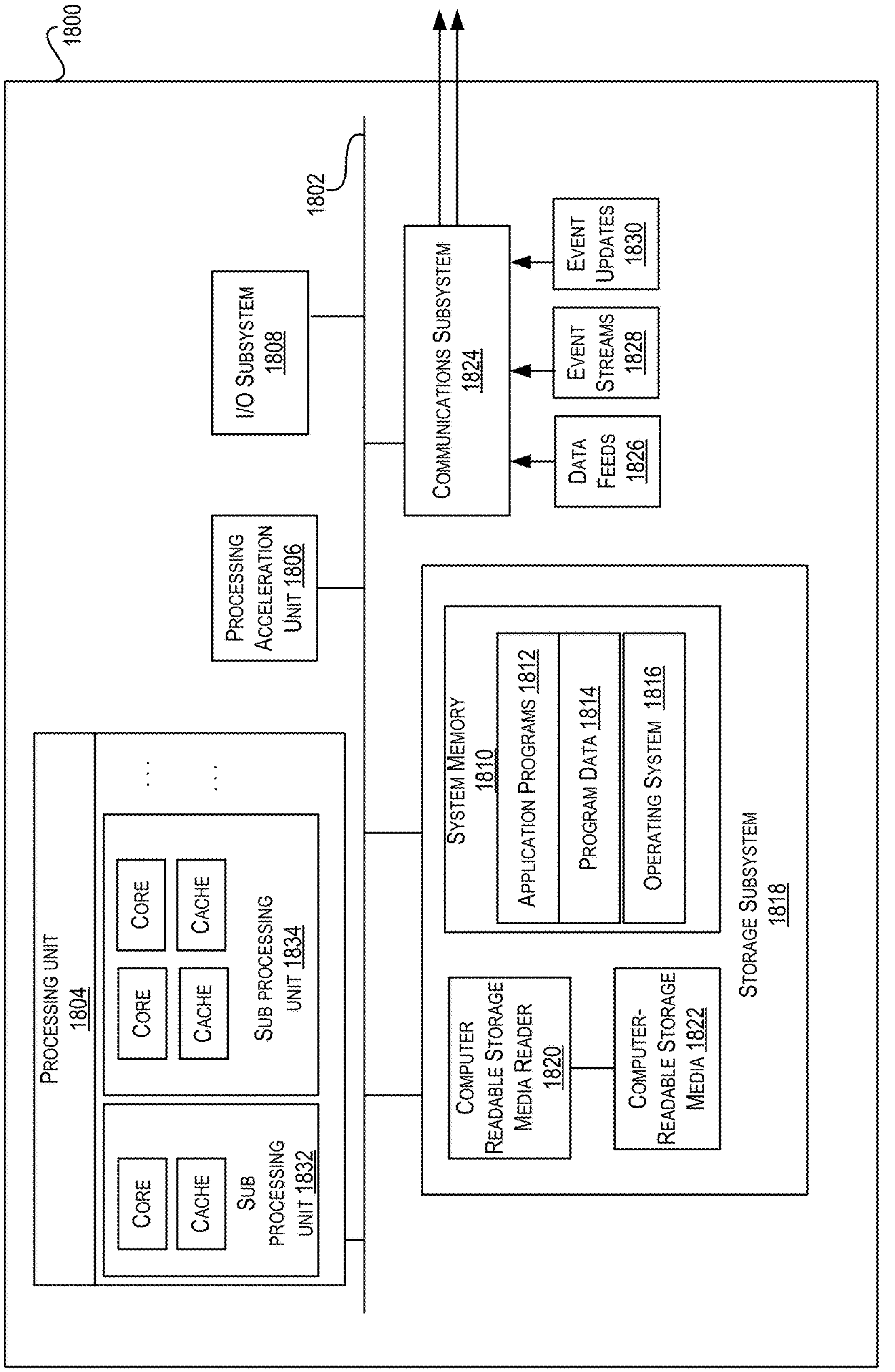
FIG. 18 is a block diagram illustrating an example computer system according to certain embodiments.

FIG. 18 illustrates an example computer system 1800, in which various embodiments may be implemented. The system 1800 may be used to implement any of the computer systems described above. As shown in the figure, computer system 1800 includes a processing unit 1804 that communicates with a number of peripheral subsystems via a bus subsystem 1802. These peripheral subsystems may include a processing acceleration unit 1806, an I/O subsystem 1808, a storage subsystem 1818 and a communications subsystem 1824. Storage subsystem 1818 includes tangible computer-readable storage media 1822 and a system memory 1810.

Bus subsystem 1802 provides a mechanism for letting the various components and subsystems of computer system 1800 communicate with each other as intended. Although bus subsystem 1802 is shown schematically as a single bus, alternative embodiments of the bus subsystem may utilize multiple buses. Bus subsystem 1802 may be any of several types of bus structures including a memory bus or memory controller, a peripheral bus, and a local bus using any of a variety of bus architectures. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 1804, which can be implemented as one or more integrated circuits (e.g., a conventional microprocessor or microcontroller), controls the operation of computer system 1800. One or more processors may be included in processing unit 1804. These processors may include single core or multicore processors. In certain embodiments, processing unit 1804 may be implemented as one or more independent processing units 1832 and/or 1834 with single or multicore processors included in each processing unit. In other embodiments, processing unit 1804 may also be implemented as a quad-core processing unit formed by integrating two dual-core processors into a single chip.

In various embodiments, processing unit 1804 can execute a variety of programs in response to program code and can maintain multiple concurrently executing programs or processes. At any given time, some, or all of the program code to be executed can be resident in processor(s) 1804 and/or in storage subsystem 1818. Through suitable programming, processor(s) 1804 can provide various functionalities described above. Computer system 1800 may additionally include a processing acceleration unit 1806, which can include a digital signal processor (DSP), a special-purpose processor, and/or the like.

I/O subsystem 1808 may include user interface input devices and user interface output devices. User interface input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may include, for example, motion sensing and/or gesture recognition devices such as the Microsoft Kinect® motion sensor that enables users to control and interact with an input device, such as the Microsoft Xbox® 360 game controller, through a natural user interface using gestures and spoken commands. User interface input devices may also include eye gesture recognition devices such as the Google Glass® blink detector that detects eye activity (e.g., 'blinking' while taking pictures and/or making a menu selection) from users and transforms the eye gestures as input into an input device (e.g., Google Glass®). Additionally, user interface input devices may include voice recognition sensing devices that enable users to interact with voice recognition systems (e.g., Siri® navigator), through voice commands.

User interface input devices may also include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, medical ultrasonography devices. User interface input devices may also include, for example, audio input devices such as MIDI keyboards, digital musical instruments and the like.

User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. In general, use of the term "output device" is intended to include all possible types of devices and mechanisms for outputting information from computer system 1800 to a user or other computer. For example, user interface output devices may include, without limitation, a variety of display devices that visually convey text, graphics, and audio/video information such as monitors, printers, speakers, headphones, automotive navigation systems, plotters, voice output devices, and modems.

Computer system 1800 may comprise a storage subsystem 1818 that provides a tangible non-transitory computer-readable storage medium for storing software and data constructs that provide the functionality of the embodiments described in this disclosure. The software can include programs, code modules, instructions, scripts, etc., that when executed by one or more cores or processors of processing unit 1804 provide the functionality described above. Storage subsystem 1818 may also provide a repository for storing data used in accordance with the present disclosure.

As depicted in the example in FIG. 18, storage subsystem 1818 can include various components including a system memory 1810, computer-readable storage media 1822, and a computer readable storage media reader 1820. System memory 1810 may store program instructions that are loadable and executable by processing unit 1804. System memory 1810 may also store data that is used during the execution of the instructions and/or data that is generated during the execution of the program instructions. Various different kinds of programs may be loaded into system memory 1810 including but not limited to client applications, Web browsers, mid-tier applications, relational database management systems (RDBMS), virtual machines, containers, etc.

System memory 1810 may also store an operating system 1816. Examples of operating system 1816 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® OS, and Palm® OS operating systems. In certain implementations where computer system 1800 executes one or more virtual machines, the virtual machines along with their guest operating systems (GOSs) may be loaded into system memory 1810 and executed by one or more processors or cores of processing unit 1804.

System memory 1810 can come in different configurations depending upon the type of computer system 1800. For example, system memory 1810 may be volatile memory (such as random access memory (RAM)) and/or non-volatile memory (such as read-only memory (ROM), flash memory, etc.) Different types of RAM configurations may be provided including a static random access memory (SRAM), a dynamic random access memory (DRAM), and others. In some implementations, system memory 1810 may include a basic input/output system (BIOS) containing basic routines that help to transfer information between elements within computer system 1800, such as during start-up.

Computer-readable storage media 1822 may represent remote, local, fixed, and/or removable storage devices plus storage media for temporarily and/or more permanently containing, storing, computer-readable information for use by computer system 1800 including instructions executable by processing unit 1804 of computer system 1800.

Computer-readable storage media 1822 can include any appropriate media known or used in the art, including storage media and communication media, such as but not limited to, volatile and non-volatile, removable, and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media.

By way of example, computer-readable storage media 1822 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 1822 may include, but is not limited to, Zip® drives, flash memory cards, universal serial bus (USB) flash drives, secure digital (SD) cards, DVD disks, digital video tape, and the like. Computer-readable storage media 1822 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 1800.

Machine-readable instructions executable by one or more processors or cores of processing unit 1804 may be stored on a non-transitory computer-readable storage medium. A non-transitory computer-readable storage medium can include physically tangible memory or storage devices that include volatile memory storage devices and/or non-volatile storage devices. Examples of non-transitory computer-readable storage medium include magnetic storage media (e.g., disk or tapes), optical storage media (e.g., DVDs, CDs), various types of RAM, ROM, or flash memory, hard drives, floppy drives, detachable memory drives (e.g., USB drives), or other type of storage device.

Communications subsystem 1824 provides an interface to other computer systems and networks. Communications subsystem 1824 serves as an interface for receiving data from and transmitting data to other systems from computer system 1800. For example, communications subsystem 1824 may enable computer system 1800 to connect to one or more devices via the Internet. In some embodiments communications subsystem 1824 can include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.12 family standards, or other mobile communication technologies, or any combination thereof), global positioning system (GPS) receiver components, and/or other components. In some embodiments communications subsystem 1824 can provide wired network connectivity (e.g., Ethernet) in addition to or instead of a wireless interface.

In some embodiments, communications subsystem 1824 may also receive input communication in the form of structured and/or unstructured data feeds 1826, event streams 1828, event updates 1830, and the like on behalf of one or more users who may use computer system 1800.

By way of example, communications subsystem 1824 may be configured to receive data feeds 1826 in real-time from users of social networks and/or other communication services such as Twitter® feeds, Facebook® updates, web feeds such as Rich Site Summary (RSS) feeds, and/or real-time updates from one or more third party information sources.

Additionally, communications subsystem 1824 may also be configured to receive data in the form of continuous data streams, which may include event streams 1828 of real-time events and/or event updates 1830, that may be continuous or unbounded in nature with no explicit end. Examples of applications that generate continuous data may include, for example, sensor data applications, financial tickers, network performance measuring tools (e.g., network monitoring and traffic management applications), clickstream analysis tools, automobile traffic monitoring, and the like.

Communications subsystem 1824 may also be configured to output the structured and/or unstructured data feeds 1826, event streams 1828, event updates 1830, and the like to one or more databases that may be in communication with one or more streaming data source computers coupled to computer system 1800.

Computer system 1800 can be one of various types, including a handheld portable device (e.g., an iPhone® cellular phone, an iPad® computing tablet, a PDA), a wearable device (e.g., a Google Glass® head mounted display), a PC, a workstation, a mainframe, a kiosk, a server rack, or any other data processing system.

Due to the ever-changing nature of computers and networks, the description of computer system 1800 depicted in the figure is intended only as a specific example. Many other configurations having more or fewer components than the system depicted in the figure are possible. For example, customized hardware might also be used and/or particular elements might be implemented in hardware, firmware, software (including applets), or a combination. Further, connection to other computing devices, such as network input/output devices, may be employed. Based on the disclosure and teachings provided herein, a person of ordinary skill in the art will appreciate other ways and/or methods to implement the various embodiments.

Although specific embodiments have been described, various modifications, alterations, alternative constructions, and equivalents are also encompassed within the scope of the disclosure. Embodiments are not restricted to operation within certain specific data processing environments but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or services are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

As used herein, when an action is "based on" something, this means the action is based at least in part on at least a part of the something. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method comprising:

receiving a first registration request message from a first client application executing on a first client device, the first registration request message including information that at least identifies the first client device and capabilities of the first client device;

receiving a second registration request message from a second client application executing on a second client device, the second registration request message including information that at least identifies the second client device and capabilities of the second client device;

pairing the first client application with the second client application upon registering the first client device and the second client device with a computing resource;

receiving, from the first client device in response to an end user interaction with the first client application, an identification of a state of the first client application and a task request message corresponding to a task to be performed by the computing resource;

synchronizing a state of the second client application with the state of the first client application;

determining a context associated with the task request message;

routing, based at least in part on the context associated with the task request message, the task request message to a selected task flow of a plurality of task flows associated with the computing resource, wherein the selected task flow is configured to dynamically select a set of configuration parameters to provide to the first client device, the second client device, or a combination of the first client device and the second client device based on a comparison of the context of the task request message to the capabilities of the first client device and the capabilities of the second client device, wherein the set of configuration parameters define a first technical format of a first graphical user interface optimized for the capabilities of the first client device, define a second technical format of a second graphical user interface optimized for the capabilities of the second client device, or a combination of the first technical format and the second technical format;

receiving a response message from the computing resource, the response message generated by the computing resource in response to the task being executed by processing steps of the task by the selected task flow, the response message defining a layout of a graphical user interface of a payload content based on the set of configuration parameters, wherein the layout is configured to automatically apply an effect of a user interaction with the first client device to the second client application, an effect of a user interaction with the second client device to the first client application, or a combination thereof; and providing the response message to one or both of the first client device and the second client device, wherein providing the response message to one or both of the first client device and the second client device causes the payload content of the response message to be displayed on display of the first client device via the first graphical user interface, a display of the second client device via the second graphical user interface, or a combination thereof, according to the layout.

2. The computer-implemented method of claim 1, wherein the payload content of the response message is simultaneously displayed on the display of the first client device and the display of the second client device, and a change in the state of the first client application or the second client application resulting from an interaction of the end user with the payload content is also applied to the other of the first client application and the second client application.

3. The computer-implemented method of claim 1, wherein the first client device and the second client device each subscribe to receive notifications from the computing resource, and the computing resource publishes a notification to the first client device and the second client device any time a client device is registered with or unregistered from the computing resource.

4. The computer-implemented method of claim 1, wherein the first client device is a handheld mobile computing device, the first client application is a mobile client application, the second client device is a desktop computing device, and the second client application is a desktop client application.

5. The computer-implemented method of claim 4, wherein the first registration request message received from the mobile computing device is generated in response to scanning, with a camera of the mobile computing device, a barcode or a quick response code displayed on the display of the second client device.

6. The computer-implemented method of claim 4, wherein:

the end user interaction with the mobile client application initiates a dictation operation during which speech of the end user is captured by a microphone of the mobile computing device;

the selected task flow receives the speech and transcribes the speech into text; and the text is included in the payload content of the response message.

7. The computer-implemented method of claim 4, wherein:

the end user interaction with the mobile client application includes a natural language utterance requesting medical information for a patient;

the selected task flow is associated with a generative artificial intelligence model that receives the natural language utterance, interprets the natural language utterance using one or more natural language processing techniques, and resultantly causes the selected task flow to retrieve the medical information;

the response message is generated by the generative artificial intelligence model; and the medical information is included in the payload content of the response message.

8. The computer-implemented method of claim 4, wherein:

the end user interaction with the mobile client application initiates an ambient recording operation during which the selected task flow of the computing resource is caused to listen to a conversation between the end user and a medical patient using a microphone of the mobile computing device;

the selected task flow generates a medical note based on the conversation; and the medical note is included in the payload content of the response message.

9. A system comprising:

one or more processing systems; and one or more computer readable media storing instructions which, when executed by the one or more processing systems, cause the system to perform operations comprising:

receiving a first registration request message from a first client application executing on a first client device, the first registration request message including information that at least identifies the first client device and capabilities of the first client device;

receiving a second registration request message from a second client application executing on a second client device, the second registration request message including information that at least identifies the second client device and capabilities of the second client device;

pairing the first client application with the second client application upon registering the first client device and the second client device with a computing resource;

receiving, from the first client device in response to an end user interaction with the first client application, an identification of a state of the first client application and a task request message corresponding to a task to be performed by the computing resource;

synchronizing a state of the second client application with the state of the first client application;

determining a context associated with the task request message;

routing, based at least in part on the context associated with the task request message, the task request message to a selected task flow of a plurality of task flows associated with the computing resource, wherein the selected task flow is configured to dynamically select a set of configuration parameters to provide to the first client device, the second client device, or a combination of the first client device and the second client device based on a comparison of the context of the task request message to the capabilities of the first client device and the capabilities of the second client device, wherein the set of configuration parameters define a first technical format of a first graphical user interface optimized for the capabilities of the first client device, define a second technical format of a second graphical user interface optimized for the capabilities of the second client device, or a combination of the first technical format and the second technical format;

receiving a response message from the computing resource, the response message generated by the computing resource in response to the task being executed by processing steps of the task by the selected task flow, the response message defining a layout of a graphical user interface of a payload content based on the set of configuration parameters, wherein the layout is configured to automatically apply an effect of a user interaction with the first client device to the second client application, an effect of a user interaction with the second client device to the first client application, or a combination thereof; and providing the response message to one or both of the first client device and the second client device, wherein providing the response message to one or both of the first client device and the second client device causes the payload content of the response message to be displayed on a display of the first client device via the first graphical user interface, a display of the second client device via the second graphical user interface, or a combination thereof, according to the layout.

10. The system of claim 9, wherein each of the first client application and the second client application supports one or more of touch, text, and voice interactions with the end user.

11. The system of claim 9, wherein:

the computing resource includes a unified events channel;

the first registration request message and the second registration request message are each configured to subscribe the first client device and the second client device to the unified events channel upon registration of the first client device and the second client device with the computing resource; and the unified events channel is configured to publish a notification to the first client device and the second client device any time a client device is registered with or unregistered from the unified events channel.

12. The system of claim 9, wherein the first client device is a handheld mobile computing device, the first client application is a mobile client application, the second client device is a desktop computing device, and the second client application is a desktop client application.

13. The system of claim 12, wherein the system includes a dictation capability, and the operations further comprise:

receiving speech of the end user captured by a microphone of the mobile computing device, the speech captured in response to initiation of a dictation operation by interaction of the end user with the mobile client application;

providing the speech to the selected task flow;

transcribing the speech into text; and including the text in the payload content of the response message.

14. The system of claim 12, wherein the system includes a digital assistant, and the operations further comprise:

receiving via a microphone of the mobile computing device, a natural language utterance from the end user, the natural language utterance requesting medical information for a patient;

providing the natural language utterance to a generative artificial intelligence model associated with the selected task flow and implemented as the digital assistant;

interpreting the natural language utterance by the generative artificial intelligence model using one or more natural language processing techniques, and resultantly causing the selected task flow to retrieve the medical information; and including the medical information in the payload content of the response message.

15. The system of claim 12, wherein the system includes an ambient recording capability, and the operations further comprise:

listening by the selected task flow, to a conversation between the end user and a medical patient using a microphone of the mobile computing device;

generating by the selected task flow, a medical note based on the conversation; and including the medical note in the payload content of the response message.

16. One or more non-transitory computer-readable media storing instructions which, when executed by one or more processors, cause a system to perform operations comprising:

receiving a first registration request message from a first client application executing on a first client device, the first registration request message including information that at least identifies the first client device and capabilities of the first client device;

receiving a second registration request message from a second client application executing on a second client device, the second registration request message including information that at least identifies the second client device and capabilities of the second client device;

pairing the first client application with the second client application upon registering the first client device and the second client device with a computing resource;

receiving, from the first client device in response to an end user interaction with the first client application, an identification of a state of the first client application and a task request message corresponding to a task to be performed by the computing resource;

synchronizing a state of the second client application with the state of the first client application;

determining a context associated with the task request message;

routing, based at least in part on the context associated with the task request message, the task request message to a selected task flow of a plurality of task flows associated with the computing resource, wherein the selected task flow is configured to dynamically select a set of configuration parameters to provide to the first client device, the second client device, or a combination of the first client device and the second client device based on a comparison of the context of the task request message to the capabilities of the first client device and the capabilities of the second client device, wherein the set of configuration parameters define a first technical format of a first graphical user interface optimized for the capabilities of the first client device, define a second technical format of a second graphical user interface optimized for the capabilities of the second client device, or a combination of the first technical format and the second technical format;

receiving a response message from the computing resource, the response message generated by the computing resource in response to the task being executed by processing steps of the task by the selected task flow, the response message defining a layout of a graphical user interface of a payload content based on the set of configuration parameters, wherein the layout is configured to automatically apply an effect of a user interaction with the first client device to the second client application, an effect of a user interaction with the second client device to the first client application, or a combination thereof; and providing the response message to one or both of the first client device and the second client device, wherein providing the response message to one or both of the first client device and the second client device causes the payload content of the response message to be displayed on a display of the first client device via the first graphical user interface, a display of the second client device via the second graphical user interface, or a combination thereof, according to the layout.

17. The one or more non-transitory computer-readable media of claim 16, wherein the first client device is a handheld mobile computing device, the first client application is a mobile client application, the second client device is a desktop computing device, and the second client application is a desktop client application.

18. The one or more non-transitory computer-readable media of claim 17, wherein the operations further comprise:

receiving speech of the end user captured by a microphone of the mobile computing device, the speech captured in response to initiation of a dictation operation by interaction of the end user with the mobile client application;

providing the speech to the selected task flow;

transcribing the speech into text; and including the text in the payload content of the response message.

19. The one or more non-transitory computer-readable media of claim 17, wherein the operations further comprise:

receiving via a microphone of the mobile computing device, a natural language utterance from the end user, the natural language utterance requesting medical information for a patient;

providing the natural language utterance to a generative artificial intelligence model associated with the selected task flow and implemented as a digital assistant;

interpreting the natural language utterance by the generative artificial intelligence model using one or more natural language processing techniques, and resultantly causing the selected task flow to retrieve the medical information; and including the medical information in the payload content of the response message.

20. The one or more non-transitory computer-readable media of claim 17, wherein the operations further comprise:

listening by the selected task flow, to a conversation between the end user and a medical patient using a microphone of the mobile computing device;

generating by the selected task flow, a medical note based on the conversation; and including the medical note in the payload content of the response message.

* * * * *